US007915297B2

(12) United States Patent
Cho et al.

(10) Patent No.: US 7,915,297 B2

(45) Date of Patent: Mar. 29, 2011

(54) ISOXAZOLE DERIVATIVES AND USE THEREOF

(75) Inventors: Jeong Woo Cho, Daejeon (KR); Sang Rak Choi, Daejeon (KR); Sun Gwan Hwang, Daejeon (KR); Kyung Chul Cho, Seoul (KR); Sung Jin Bae, Daejeon (KR); Tae Sung Koo, Daejeon (KR)

(73) Assignee: SK Holdings Co., Ltd., Seoul (KR)

(*) Notice: Subject to any disclaimer, the term of this patent is extended or adjusted under 35 U.S.C. 154(b) by 0 days.

(21) Appl. No.: 12/159,718

(22) PCT Filed: Dec. 28, 2006

(86) PCT No.: PCT/KR2006/005837

§ 371 (c)(1), (2), (4) Date: Oct. 23, 2008

(87) PCT Pub. No.: WO2007/078113

PCT Pub. Date: Jul. 12, 2007

(65) Prior Publication Data

US 2009/0131336 A1 May 21, 2009

(30) Foreign Application Priority Data

Dec. 30, 2005 (KR) ........................ 10-2005-0135247
Dec. 27, 2006 (KR) ........................ 10-2006-0135390

(51) Int. Cl.
*A61K 31/422* (2006.01)
*A61K 31/443* (2006.01)
*C07D 261/12* (2006.01)
*C07D 413/04* (2006.01)

(52) U.S. Cl. ..................... 514/340; 514/378; 546/272.1; 548/248

(58) Field of Classification Search ........................ None
See application file for complete search history.

(56) References Cited

U.S. PATENT DOCUMENTS

| | | | | |
|---|---|---|---|---|
| 3,455,837 | A | 7/1969 | Maeder | |
| 3,852,293 | A | 12/1974 | Ariyan et al. | |
| 5,201,932 | A * | 4/1993 | Maywald et al. | 504/271 |
| 5,374,605 | A | 12/1994 | Hallenbach et al. | |
| 2003/0139404 | A1 | 7/2003 | Haag et al. | |
| 2008/0090882 | A1 | 4/2008 | Dorsch et al. | |

FOREIGN PATENT DOCUMENTS

| | | | |
|---|---|---|---|
| DE | 2062373 | * | 12/1970 |
| EP | 0419944 | | 12/1990 |
| EP | 0726263 | | 10/1996 |
| GB | 1390402 | | 4/1975 |
| GB | 1492663 | | 11/1977 |
| JP | 08-027130 | | 1/1996 |
| JP | 2006-176443 A | * | 7/2006 |
| WO | WO 96/00218 | | 1/1996 |
| WO | WO03/000649 | | 1/2003 |
| WO | 03013517 | | 2/2003 |
| WO | WO 2008/046072 | * | 4/2008 |

OTHER PUBLICATIONS

Andersson et al. Investigation of central versus peripheral effects of estradiol in ovariectomized mice. Journal of Endocrinology (2005) 187, pp. 303-309.*

Hobar et al. "Prevention of Osteoporosis." eMedicineHealth: Pratical Guide to Health. Accessed May 20, 2009.*

Machine translation of JP 2006-176443A. Obtained Dec. 8, 2009 from AIPN website.*

Benincori et al. J. Chem. Soc. Perkin Trans. 1 (1993) pp. 675-680.*

Bennett et al., Regulation of osteoblastogenesis and bone mass by Wnt10b, Proc. Natl. Acad. Sci. U S A, Mar. 1, 2005;102(9):3324-9, Epub Feb. 22, 2005.

He et al., BMP signaling inhibits intestinal stem cell self-renewal through suppression of Wnt- bold beta -catenin signaling, Nature Genetics, Sep. 19, 2004, vol. 36, pp. 1117-1121.

Pae et al., Synthesis and in vitro activity of new oxazolidinone antibacterial agents having substituted isoxazoles, Bioorganic & Medicinal Chemistry Letters, vol. 9, Issue 18, Sep. 20, 1999, pp. 2679-2684.

Tamai et al., LDL Receptor-Related Proteins in Wnt Signal Transduction, Nature, Sep. 28, 2000; vol. 407 pp. 530-535.

Winston et al., A family of mammalian F-box proteins, Cur.r Biol. Oct. 11, 1999, 9:1180-1182.

Andreichov, Yu S., et al., Journal of Organic Chemistry of the USSR (English Translation). YOCYA9 23(10) 1895-1996 (1987).

Afridi, Sultan A., at al. Heterocyclic Rearrangements. Part XIC. Attempts to Activate Ring-Opening-Ring-closure Rearrangements with Carbon as the Central Atom. School of Chemical Sciences, pp. 315-320. (1976).

Yarovenko, V.N. et al., Synthesis of Oxamic Acids Thiohydrazides and Carbamoyl-1, 3, 4-thiadiazoles, Russian Journal of Organic Chemistry, vol. 39, No. 8, 2003, pp. 1133-1139.

Qian, Chang-Yi, et al., Synthesis of 2,3,5-Trisubstituted Furans by the Acid-Catalyzed Decomposition of 1,2-Dioxan-3-ols., J. Heterocyclic Chem., 31, 1219 (1994).

Yokooji, Aya, et al. Palladium-catalyzed direct arylation of thiazoles with aryl bromides., Tetrahedron 59 (2003) pp. 5685-5689.

International Preliminary Report and Written Opinion dated Jun. 5, 2007.

Westendorf, Jennifer J., et al., Wnt signaling in osteoblasts and bone diseases., Gene 341 (2004) 19-39.

Fargher, Robert George, et al., LXXXVII.-The Abnormal Behaviour of Glyoxaline-carbaxylic esters and anilides towards Diazonium salts., Wellcome Chemical Research Laboratories, pp. 1015-1020, ( 1920).

Milyutin, A.V., et al., Synthesis, Properties, and Biological Activity of 3-Pyridylamides of 4-Aryl-2-hydroxy-4-oxo-2-butenic (Aroylpyruvic) acids., Pharmaceutical Chemistry Journal, vol. 31, pp. 30-33, (1997).

* cited by examiner

*Primary Examiner* — Rebecca L Anderson
*Assistant Examiner* — Alicia L Otton

(57) ABSTRACT

Disclosed herein are isoxazole derivatives and uses thereof. Serving as agonists of Wnt, the isoxazole derivatives activate Wnt/β-catenin signaling and thus can be used in the treatment and prevention of diseases related to the signal transduction. Also, pharmaceutically acceptable salts of the isoxazole derivatives are disclosed.

3 Claims, 4 Drawing Sheets

<Gene structure for determining β-catenin activity>

<Cell based Wnt agonist screening system>

<Luciferase protein levels upon treatment of cell-based Wnt agonist screening system with LiCl(positive control)>

<Effects of Compounds on intracellular accumulation of β-catenin>

1. Control
2. LiCl, 20mM
3. Derivative (1),30μM
4. Derivative(1),60μM
5. Derivative(12),30μM
6. Derivative(12),60μM
7. Wnt3a <Effect of Derivative(1) on the ALP activity of ST2 cell line>

<Effect of Derivatives on the $Ca^{++}$ deposition within ST2 cell line>

ISOXAZOLE DERIVATIVES AND USE THEREOF

TECHNICAL FIELD

The present invention relates to isoxazole derivatives and uses thereof. More particularly, the present invention relates to isoxazole derivatives acting as agonists having effects of activating Wnt/β-catenin signal transmission, a method for preparing the isoxazole derivatives and uses thereof.

BACKGROUND ART

Wnt (pronounced "wint") proteins are a family of cysteine-rich, secretory glycoproteins of approximately 40 kDa, and are known to be involved in various cell developmental processes including cell polarity (Moon R T et al., Science, 2002; Reya T and Clevers H, Nature, 2005). In humans, 19 wnt proteins have been reported, and 10 frizzled proteins as Wnt receptors and 2 coreceptors (LPR 5 and 6) are known (He X C et al., Nat Genet, 2004; Tamai K et al, Mol Cell, 2004; Tamai K et al., Nature, 2000).

Typical Wnt signaling induces stabilization and accumulation of cytoplasmic 3-catenin through the regulation of protein kinase complex, translocation of β-catenin into the nucleus where it acts as a transcription activivator. This transcription activity is reported to be caused by transcription factors in the group of the Lefl/Tcf (Moon R T et al., Science, 2002; Reya T and Clevers H, Nature, 2005; Wodarz A and Nusse R, Annu Rev Cell Dev Biol., 1998).

In the absence of a Wnt signal, β-catenin is phosphorylated by GSK-3β complex (glycogen synthase kinase 3β), which is composed of the protein kinases, GSK-3β and casein kinase I (CKI), axin, Dsh (dishevelled) protein, and APC (Adenomatous Polyposis Coli). The phosphorylation of β-catenin leads to the production of the DpSGXXpS motif (where pS stands for phosphorylated serine and X for any amino acid), which is recognized by β-TrCP containing the F-box which is a kind of the E3/SCF ubiquitin ligase. After being ubiquitinated, β-catenin undergoes proteasomal degradation, thus Lefl/Tcf-mediated transcriptional activity is inhibited (Hart M et al., Curr Biol., 1999; Winston J T et al., Curr Biol., 1999).

Meanwhile, when Wnt proteins bind to the frizzled receptors and the coreceptor LRP5, the activity of the GSK-3β complex loses its ability to induce phosphorylation of β-canetin, resulting in the promotion of transcription of target genes by association with Lefl/Tcf proteins (Reya T and Clevers H, Nature, 2005; Tamai K et al., Mol Cell, 2004; Westendorf J J et al., Gene, 2004).

Mutation of the proteins involved in the Wnt signal transduction system is closely correlated with various human diseases such as abnormalities in development, hair follicle morphogenesis, stem cell differentiation and cell proliferation, and particularly, is also believed to be related to oncogenesis, such as colorectal cancer and leukemia (Taipale et al., Nature, 2001). In addition, it has been reported that the Wnt signal transduction system plays a crucial role in the differentiation and development of nerve cells for the central nervous system, suggesting a relationship between Wnt proteins and the incidence of various diseases of the central nervous system, including neurodegenerative diseases and depression. Particularly, it is also found that Wnt signaling is related to diseases resulting from the abnormality of nerve cells, such as brain damage, Parkinson's disease, stroke, epilepsy, Alzheimer's disease, depression, bipolar disorder, and schizophrenia. Thus, to treat these diseases, it requires to be substituted with healthy nerve cells which operate normally, and as an alternative, the control of Wnt signaling was suggested (Dieter-Chichung Lie et al., Nature 2005).

Further, according to the recent research, Wnt proteins have been found to be significantly involved in the differentiation of adult stem cells into adipocytes or osteoblasts. Firstly, it is found that persons with non functional LRP5, a Wnt coreceptor, undergo a abnormally significant decrease in bone density (Boyden L M et al., N Engl J Med., 2002; Gong Y et al., Cell, 2001). From studies with Wnt10b transgenic mice, which were manipulated to be highly expressed specifically in adipose and bone marrow cells, it was observed they were remarkably increased in bone density, whereas decreased in obesity and glucose intolerance by high adipose ingestion (Longo K A et al., J Biol. Chem., 2004; Bennett C N et al, Proc Natl Acad Sci USA, 2005). Also, in case of the overexpression of Wnt10b in adult stem cells, the level of osteoblast-specific markers is found to be increased (Bennett C N et al, Proc Natl Acad Sci USA, 2005). In contrast, Wnt10b-knockout mice were measured to have significantly decreased levels of osteoblasts and bone density.

Additionally, it is reported that β-catenin itself plays an essential role in postnatal bone acquisition through knockout mice model (Holmen et al., J Biol. Chem., 2005).

While Stably activated β-catenin acts to increase the expression of the bone-specific alkaline phosphatase, a marker of early-stage osteoblast differentiation, it does not effect on the expression of osteocalcin, a marker of late-stage osteoblast differentiation (Vinals F et al., FEBS Lett., 2002). Moreover, Lefl and β-catenin may inhibit Runx2-dependent transcriptional activation (Kahler R A and Westendorf J J, J Biol. Chem., 2003). While Wnt10b signaling transduced along the typical Wnt pathways, it has a signal mechanism, which is dependent on Wnt/GSK-3b but not dependent on β-catenin, in the regulation of the production of osteoblasts and adipocytes (Vinals F et al., FEBS Lett., 2002; Kahler R A and Westendorf J J, J Biol. Chem., 2003). Therefore, it has been suggested that there exist β-catenin-independent mechanisms.

On the basis of the significance of the above-mentioned Wnt signal transduction pathways, Wnt signaling molecules are considered as targets for drug screening to develop medications for curing Wnt-related diseases, such as breast cancer, colorectal cancer, metabolic bone diseases, obesity, etc. Extensive efforts have been made to find new regulators, either activators or inhibitors, and develop them into medications.

Recently, also, the Wnt signaling pathway has been reported to play an important role in the maintenance, differentiation and proliferation of stem cells (Reya T et al., Nature., 2003; Trowbridge J J et al., NatuerMed., 2006). Thus, extensive research has been directed to the development of promoter for tissue regeneration, control of hair loss, haematopoiesis, and stimulation of stem cell growth, maintenance and differentiation.

In modern times, bone diseases is increasing due to socioenvironmental and genetic factors, particularly due to increase of population of elderly persons. Generally, bone diseases occur and develop without special symptoms, and rapidly worsen with age. Although many drugs have been developed for the treatment of bone diseases thus far, most of them mainly aim to alleviate pain or to retard the decrease of bone density. They are not effective as a curative medication which aims for increasing the bone density of patients who suffer from osteoporosis. Some other drugs are usually in the form of injections and are reported to produce side effects upon long-term administration thereof.

Therefore, there is a need for novel drugs that effectively treat bone diseases without the problems mentioned above.

DISCLOSURE

Technical Problem

To solve the above problem, present inventors conducted intensive and thorough research, resulted in synthesis of isoxazole derivatives which is represented by the following Chemical Formula 1 and pharmaceutically useful salts thereof, can act as agonists of the Wnt/β-catenin signal transduction. And inventors found that the isoxazole derivatives are effective in osteoblastogenesis and useful for the prevention and treatment of various bone diseases, including osteoporosis.

Technical Solution

According to one aspect of the present invention for accomplishing the above object, it provides isoxazole derivatives and pharmaceutically useful salts thereof, which can activate wnt/β-catenin signaling.

According to another aspect of the present invention for accomplishing the above object, it provides methods for preparing isoxazole derivatives and pharmaceutically useful salts thereof, which activate wnt/β-catenin signaling.

According to still another aspect of the present invention for accomplishing the above object, it provides a composition comprising an isoxazole derivative as an active ingredient for activating wnt/β-catenin signaling and the use thereof in the treatment and prevention of bone diseases.

BEST MODE

Figure 1:
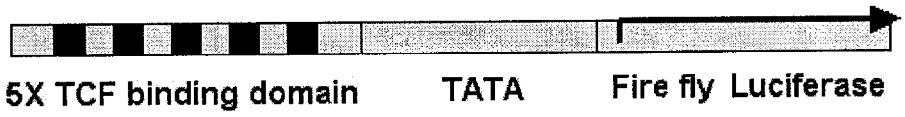
FIG. 1 is a diagram showing a gene structure designed to determine the effect of transcriptional activity of β-catenin.

A detailed description of the present invention starts with the definition of several terms used in the present invention as follows.

a) Alkyl group: refers to a linear or branched, saturated or unsaturated hydrocarbon containing 1 to 10 carbon atoms, wherein one or more hydrogen may be substituted with one or more substituent selected from a group consisting of acyl, amino, carboalkoxy, carboxy, carboxyamino, —O-carbamoyl (—O—(C═O)—NH2), cyano, halo, hydroxy, nitro, thio, alkyl, cycloalkyl, aryl, alkoxy, aryloxy, sulfoxy, guanido to the maximum possible number, irrespective of the order and kind thereof.

b) Cycloalkyl group: refers to a non-aromatic, monocyclic or polycyclic ring hydrocarbon compound, whether saturated or partially unsaturated, which consists of 3~12 ring constitutional members with 0~5 hetero atoms, such as oxygen, sulfur, nitrogen, etc., therein. It may 3-12-gon single ring compound or fused ring compound, wherein one or more hydrogen may be substituted with one or more substituent selected from a group consisting of acyl, amino, carboalkoxy, carboxy, carboxyamino, —O-carbamoyl (—O—(C═O)—$NH_2$), cyano, halo, hydroxy, nitro, thio, alkyl, cycloalkyl, aryl, alkoxy, aryloxy, sulfoxy, guanido to the maximum possible number, irrespective of the kind and order thereof.

Concrete examples of the cycloalkyl group include, but are not limited to, cyclopropyl, cyclobutyl, cyclopentyl, cyclohexyl, cycloheptyl, cyclooctyl, morpholinyl, homomorpholinyl, thiomorpholinyl, homothiomorpholinyl, thiomorpholinyl S-oxide, thiomorpholinyl S,S-dioxide, piperidinyl, homopiperidinyl, piperazinyl, homopiperazinyl, pyrrolidinyl, pyrrolinyl, tetrahydropyranyl, tetrahydrofuranyl, tetrahydrothienyl, oxazolidinonyl, dihydropyrazolyl, dihydropyrrolyl, dihydropyrazinyl, dihydropyridinyl, dihydropyrimidinyl, dihydrofuryl, and dihydropyranyl.

c) Aryl group: refers to a single or fused aromatic ring consisting of 5 to 15 ring members and 0 to 5 heteroatoms selected from oxygen, sulfur and nitrogen, wherein said rings may be unsubstituted or substituted with one or more substituents to the maximum number possible, said substituents being selected from the group consisting of acyl, amino, carboalkoxy, carboxy, carboxyamino, —O-carbamoyl, cyano, halo, hydroxy, nitro, thio, alkyl, cycloalkyl, aryl, alkoxy, aryloxy, sulfoxy and guanido.

Concrete example of the aryl group include, but are not limited to, phenyl, 1-naphtyl, 2-naphtyl, pyridinyl, pyrimidinyl, quinolinyl, benzothienyl, indolyl, pyrazinyl, isoindolyl, isoquinolyl, quinazolinyl, quinoxalinyl, phthalazinyl, imidazolinyl, isoxazolyl, pyrazolyl, oxazolyl, thiazolyl, indolizinyl, indazolyl, benzothiazolyl, benzimidazolyl, benzofuranyl, thienyl, pyrrolyl, oxadiazolyl, thiadiazolyl, triazolyl, tetrazolyl, oxazolopyridinyl, imidazopyridinyl, isothiazolyl, cinnolinyl, carbazolyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiopyranyl, benzopyranyl, benzothiopyranyl, coumarinyl, isocoumarinyl, chromonyl, chromanonyl, pyridinyl-N-oxide, tetrahydroquinolinyl-N-oxide, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl-N-oxide, pyrimidinyl-N-oxide, pyrazinyl-N-oxide, quinolinyl-N-oxide, indolyl-N-oxide, indolinyl-N-oxide, pyrazinyl-N-oxide, isoquinolyl-N-oxide, quinazolinyl-N-oxide, quinoxalinyl-N-oxide, phthalazinyl-N-oxide, imidazolinyl-N-oxide, isoxazolyl-N-oxide, oxazolyl-N-oxide, thiazolyl-N-oxide, indolizinyl-N-oxide, indazolyl-N-oxide, benzothiazolyl-N-oxide, benzimidazolyl-N-oxide, pyrrolyl-N-oxide, oxadiazolyl-N-oxide, thiadiazolyl-N-oxide, triazolyl-N-oxide, and tetrazolyl-N-oxide.

d) Halo: generally refers to fluoro, chloro, bromo and iodo.

For convenience of explanation, the terms used in the present invention will be used in the abbreviated forms defined below.

N,N-dimethyl formamide: DMF tetrahydrofuran: THF 1-(3-dimethyl aminopropyl)-3-ethylcarbodiimide: EDC 1-hydroxybenzotriazole hydrate: HOBt 1,1'-carbonyldiimidazole: CDI diphenylphosphoryl azide: DPPA triethylamine: TEA methyl: Me ethyl: Et Hereinafter, the present invention will be described in further detail.

In accordance with a first aspect, the present invention pertains to a novel isoxazole derivative, represented by the following chemical formula 1, which can activate Wnt/β-catenin signaling.

Chemical Formula 1

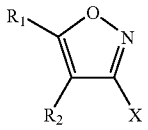

wherein, $R_1$ is hydrogen, an alkyl group, a cycloalkyl group, an alkyl group substituted with cycloalkyl group, an aryl group, an alkyl group substituted with aryl group, acyl, amino, carboalkoxy, carboxy, carboxyamino, —O-carbamoyl (—O—(C═O)—$NH_2$), cyano, halo, hydroxy, nitro, thio, alkoxy, aryloxy, sulfoxy, or guanido, and preferably an aryl group;

$R_2$ is hydrogen, an alkyl group, a cycloalkyl group, an alkyl group substituted with cycloalkyl group, an aryl group, an alkyl group substituted with aryl group, acyl, amino, carboalkoxy, carboxy, carboxyamino, —O-carbamoyl (—O—(C═O)—$NH_2$), cyano, halo, hydroxy, nitro, thio, alkoxy, aryloxy, sulfoxy, or guanido, and preferably hydrogen, $R_1$ and $R_2$ together may form a ring of an aryl group; and X is a substituent represented by the following Chemical Formulas 2 to 6.

Chemical Formula 2

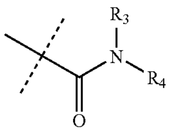

Chemical Formula 3

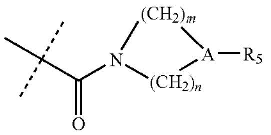

Chemical Formula 4

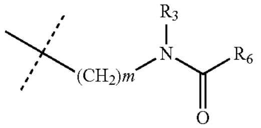

Chemical Formula 5

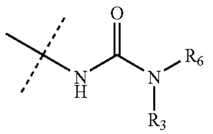

Chemical Formula 6

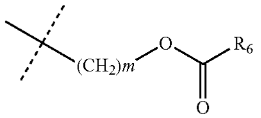

In Chemical Formulas 2 to 6, m is 0, 1 or 2, n is 0, 1 or 2,

A is C or N, $R_3$ is hydrogen, an alkyl group, a cycloalkyl group, an alkyl group substituted with cycloalkyl group, an aryl group or an alkyl group substituted with aryl group, and preferably hydrogen, $R_4$ is hydrogen, an alkyl group, a cycloalkyl group, an alkyl group substituted with cycloalkyl group, an aryl group, or an alkyl group substituted with aryl group, with preference for an alkyl group substituted with aryl group, or may be selected from a group consisting of compounds represented by the following Chemical Formulas 7 to 16, $R_5$ is hydrogen, an alkyl group, a cycloalkyl group, an alkyl group substituted with cycloalkyl group, an aryl group or an alkyl group substituted with aryl group, and preferably an aryl group, $R_6$ is hydrogen, an alkyl group, a cycloalkyl group, an alkyl group substituted with cycloalkyl group, an aryl group, an alkyl group substituted with aryl group, or a compound represented by the following Chemical Formula 17.

Chemical Formula 7

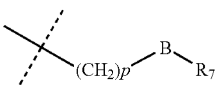

Chemical Formula 8

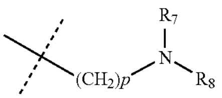

-continued

Chemical Formula 9

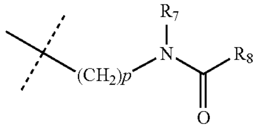

Chemical Formula 10

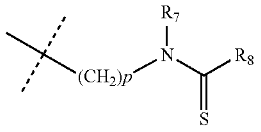

Chemical Formula 11

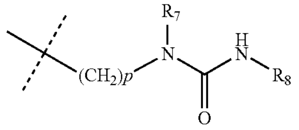

Chemical Formula 12

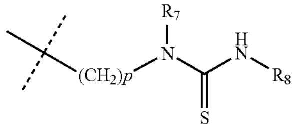

Chemical Formula 13

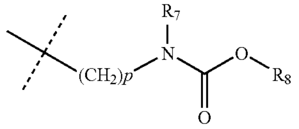

Chemical Formula 14

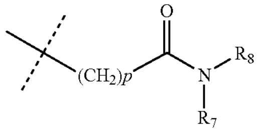

Chemical Formula 15

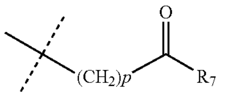

Chemical Formula 16

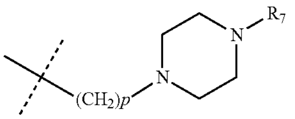

Chemical Formula 17

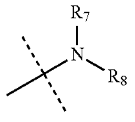

In Chemical Formulas 7 to 17, p is 1, 2, 3 or 4,

B is O, S, SO, S(=O)2, or $NR_8S(=O)_2$, $R_7$ is hydrogen, an alkyl group, a cycloalkyl group, an alkyl group substituted with cycloalkyl group, an aryl group, or an alkyl group substituted with aryl group, $R_8$ is hydrogen, an alkyl group, a cycloalkyl group, an alkyl group substituted with cycloalkyl group, an aryl group, or an alkyl group substituted with aryl group.

In addition to the compounds represented by Chemical Formula 1, pharmaceutically acceptable acid or base addition salts and stereochemical isomers thereof are in the range of the isoxazole derivatives of the present invention. As long as it maintains the activity of the parent compound in the subjects administered therewith out undesirable effects, any salt is within the scope of the present invention, and no particular limitation is imposed thereon. The salts may be inorganic or organic salts. Preferable are salts of acetic, nitric, aspartic, sulfonic, sulfuric, maleic, glutamic, formic, succinic, phosphoric, phthalic, tannic, tartaric, hydrobromic, propionic, benzenesulfonic, benzoic, stearic, esyl, lactic, bicarbonic, bisulfuric, bitartaric, oxalic, butyric, calcium edetate, camsylic, carbonic, chlorobenzoic, citric, edetic, toluenesulfonic, edisylic, esylic, fumaric, gluceptic, pamoic, gluconic, glycollylarsanilic, methylnitric, polygalactouronic, hexylresorcinoic, malonic, hydrabamic, hydrochloric, hydroiodic, hydroxynaphthoic, isethionic, lactobionic, mandelic, estolic, methylsulfuric, mucic, napsylic, muconic, p-nitromethanesulfonic, hexamic, pantothenic, monohyrogen phosphoric, dihyrogen phosphoric, salicylic, sulfamic, sulfanilic, methanesulfonic, or teoclic acid.

Also, the form of basic salt may include, for example, ammonium salt, alkali metal salts, alkaline earth metal salts such as lithium, sodium, potassium, magnesium and calcium salts, organic base salts, such as bezathine, N-methyl-D-glucamine, hydrabamine salts, and amino acids, such as arginine and lysine.

Meanwhile, the form of salt may be converted to free forms by treatment with suitable bases or acids.

The term "addition salt" as used herein means salts that include solvates which compounds of Chemical Formula 1 or salts thereof can form. The solvates may be exemplified by hydrates and alcoholates.

As used herein, the term "stereochemical isomers of compounds of Chemical Formula 1" refers to all possible forms that the compounds of Chemical Formula 1 can have. Unless specified or mentioned otherwise, the chemical names of the compounds of Chemical Formula 1 indicate mixtures of all possible stereochemical isomers, including all diastereomers and enantiomers of basic molecular structures.

Particularly, each chiral center may have either R or S-configuration, and substitutents on bivalent cyclic (partially) saturated radicals may have a cis- or trans-configuration. Compounds having double bonds may have E- or Z-stereochemistry, if present. All stereochemical isomers of the compounds represented by Chemical Formula 1 are intended to be included within the scope of the present invention.

According to the definition of Chemical Formula 1, a preferable isoxazole derivative according to the present invention may be a compound represented by any of the following Chemical Formulas 18 to 22.

Chemical Formula 18

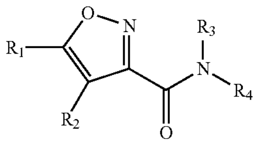

Chemical Formula 19

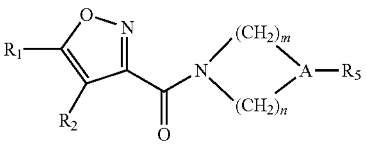

Chemical Formula 20

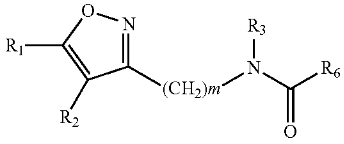

-continued

Chemical Formula 21

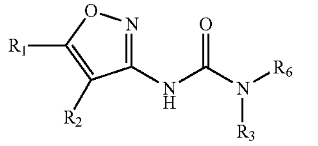

Chemical Formula 22

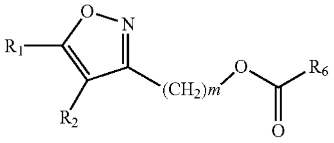

In Chemical Formulas 18 to 22, m, n, A, $R_1$, $R_2$, $R_3$, $R_4$, $R_5$ and $R_6$ are each the same as defined in Chemical Formula 1.

More preferable examples of the isoxazole derivatives according to the present invention include the following derivatives (1) to (254).

Derivative (1): 5-furan-2-yl-isoxazole-3-carboxylic acid (3-imidazol-1-yl-propyl)-amide Derivative (2): 5-furan-2-yl-isoxazole-3-carboxylic acid (2-hydroxy-phenyl)-amide Derivative (3): 5-furan-2-yl-isoxazole-3-carboxylic acid (2-amino-phenyl)-amide Derivative (4): 5-furan-2-yl-isoxazole-3-carboxylic acid benzylamide Derivative (5): 5-furan-2-yl-isoxazole-3-carboxylic acid phenethyl-amide Derivative (6): 5-furan-2-yl-isoxazole-3-carboxylic acid (3-phenyl-propyl)-amide Derivative (7): 5-furan-2-yl-isoxazole-3-carboxylic acid (pyridin-2-ylmethyl)-amide Derivative (8): 5-furan-2-yl-isoxazole-3-carboxylic acid (pyridin-3-ylmethyl)-amide Derivative (9): 5-furan-2-yl-isoxazole-3-carboxylic acid (pyridin-4-ylmethyl)-amide Derivative (10): 5-furan-2-yl-isoxazole-3-carboxylic acid (2-pyridin-2-yl-ethyl)-amide Derivative (11): 5-furan-2-yl-isoxazole-3-carboxylic acid (2-pyridin-3-yl-ethyl)-amide Derivative (12): 5-furan-2-yl-isoxazole-3-carboxylic acid (2-pyridin-4-yl-ethyl)-amide Derivative (13): 5-furan-2-yl-isoxazole-3-carboxylic acid (2-o-tolyl-ethyl)-amide Derivative (14): 5-furan-2-yl-isoxazole-3-carboxylic acid (2-m-tolyl-ethyl)-amide Derivative (15): 5-furan-2-yl-isoxazole-3-carboxylic acid (2-p-tolyl-ethyl)-amide Derivative (16): 5-furan-2-yl-isoxazole-3-carboxylic acid [2-(2-fluoro-phenyl)-ethyl]-amide Derivative (17): 5-furan-2-yl-isoxazole-3-carboxylic acid [2-(3-fluoro-phenyl)-ethyl]-amide Derivative (18): 5-furan-2-yl-isoxazole-3-carboxylic acid [2-(4-fluoro-phenyl)-ethyl]-amide Derivative (19): 5-furan-2-yl-isoxazole-3-carboxylic acid [2-(2-methoxy-phenyl)-ethyl]-amide Derivative (20): 5-furan-2-yl-isoxazole-3-carboxylic acid [2-(3-methoxy-phenyl)-ethyl]-amide Derivative (21): 5-furan-2-yl-isoxazole-3-carboxylic acid [2-(4-methoxy-phenyl)-ethyl]-amide Derivative (22): 5-furan-2-yl-isoxazole-3-carboxylic acid [2-(4-hydroxy-phenyl)-ethyl]-amide Derivative (23): 5-furan-2-yl-isoxazole-3-carboxylic acid [2-(3-hydroxy-phenyl)-ethyl]-amide Derivative (24): 5-furan-2-yl-isoxazole-3-carboxylic acid [2-(4-chloro-phenyl)-ethyl]-amide Derivative (25): 5-furan-2-yl-isoxazole-3-carboxylic acid [2-(4-bromo-phenyl)-ethyl]-amide Derivative (26): 5-furan-2-yl-isoxazole-3-carboxylic acid [2-(4-amino-phenyl)-ethyl]-amide Derivative (27): 5-furan-2-yl-isoxazole-3-carboxylic acid [2-(4-nitro-phenyl)-ethyl]-amide Derivative (28): 5-furan-2-yl-isoxazole-3-carboxylic acid [2-(3,4-dihydroxy-phenyl)-ethyl]-amide Derivative (29): 5-furan-2-yl-isoxazole-3-carboxylic acid (2-benzo[1,3]dioxol-5-yl-ethyl)-amide Derivative (30): 5-furan-2-yl-isoxazole-3-carboxylic acid [2-(3,4-dimethoxy-phenyl)-ethyl]-amide Derivative (31): 4-{2-[(5-furan-2-yl-isoxazole-3-carbonyl)-amino]-ethyl}-benzoic acid methyl ester Derivative (32): 4-{2-[(5-furan-2-yl-isoxazole-3-carbonyl)-amino]-ethyl}-benzoic acid Derivative (33): 5-furan-2-yl-isoxazole-3-carboxylic acid (2-imidazol-1-yl-ethyl)-amide Derivative (34): 5-furan-2-yl-isoxazole-3-carboxylic acid (4-imidazol-1-yl-butyl)-amide Derivative (35): 5-furan-2-yl-isoxazole-3-carboxylic acid [2-(2-methyl-imidazol-1-yl)-ethyl]-amide Derivative (36): 5-furan-2-yl-isoxazole-3-carboxylic acid [2-(5-methyl-imidazol-1-yl)-ethyl]-amide Derivative (37): 5-furan-2-yl-isoxazole-3-carboxylic acid [2-(4-methyl-imidazol-1-yl)-ethyl]-amide Derivative (38): 5-furan-2-yl-isoxazole-3-carboxylic acid (2-[1,2,4]triazol-1-yl-ethyl)-amide Derivative (39): 5-furan-2-yl-isoxazole-3-carboxylic acid (2-pyrazol-1-yl-ethyl)-amide Derivative (40): 5-furan-2-yl-isoxazole-3-carboxylic acid (2-[1,2,3]triazol-2-yl-ethyl)-amide Derivative (41): 5-furan-2-yl-isoxazole-3-carboxylic acid (2-[1,2,3]triazol-1-yl-ethyl)-amide Derivative (42): 5-furan-2-yl-isoxazole-3-carboxylic acid (2-tetrazol-2-yl-ethyl)-amide Derivative (43): 5-furan-2-yl-isoxazole-3-carboxylic acid (2-tetrazol-1-yl-ethyl)-amide Derivative (44): 5-furan-2-yl-isoxazole-3-carboxylic acid [3-(2-methyl-imidazol-1-yl)-propyl]-amide Derivative (45): 5-furan-2-yl-isoxazole-3-carboxylic acid [3-(2-ethyl-imidazol-1-yl)-propyl]-amide Derivative (46): 5-furan-2-yl-isoxazole-3-carboxylic acid [3-(2-isopropyl-imidazol-1-yl)-propyl]-amide Derivative (47): 5-furan-2-yl-isoxazole-3-carboxylic acid [3-(2-phenyl-imidazol-1-yl)-propyl]-amide Derivative (48): 5-furan-2-yl-isoxazole-3-carboxylic acid (3-pyrazol-1-yl-propyl)-amide Derivative (49): 5-furan-2-yl-isoxazole-3-carboxylic acid (3-[1,2,3]triazol-1-yl-propyl)-amide Derivative (50): 5-furan-2-yl-isoxazole-3-carboxylic acid (3-[1,2,3]triazol-2-yl-propyl)-amide Derivative (51): 5-furan-2-yl-isoxazole-3-carboxylic acid (3-[1,2,4]triazol-1-yl-propyl)-amide Derivative (52): 5-furan-2-yl-isoxazole-3-carboxylic acid (3-tetrazol-1-yl-propyl)-amide Derivative (53): 5-furan-2-yl-isoxazole-3-carboxylic acid (3-tetrazol-2-yl-propyl)-amide Derivative (54): 5-furan-2-yl-isoxazole-3-carboxylic acid [3-(2-nitro-imidazol-1-yl)-propyl]-amide Derivative (55): 5-furan-2-yl-isoxazole-3-carboxylic acid [3-(4-nitro-imidazol-1-yl)-propyl]-amide Derivative (56): 5-furan-2-yl-isoxazole-3-carboxylic acid [3-(4-methyl-imidazol-1-yl)-propyl]-amide Derivative (57): 5-furan-2-yl-isoxazole-3-carboxylic acid [3-(5-methyl-imidazol-1-yl)-propyl]amide Derivative (58): 1-{3-[(5-furan-2-yl-isoxazole-3-carbonyl)-amino]-propyl}-1H-imidazole-4-carboxylic acid methyl ester Derivative (59): 1-{3-[(5-furan-2-yl-isoxazole-3-carbonyl)-amino]-propyl}-1H-imidazole-4-carboxylic acid Derivative (60): 5-furan-2-yl-isoxazole-3-carboxylic acid [3-(4-bromo-imidazol-1-yl)-propyl]-amide Derivative (61): 5-furan-2-yl-isoxazole-3-carboxylic acid methyl-(2-pyridin-2-yl-ethyl)-amide Derivative (62): 5-furan-2-yl-isoxazole-3-carboxylic acid (3-imidazol-1-yl-propyl)-methyl-amide Derivative (63): 5-furan-2-yl-isoxazole-3-carboxylic acid ethyl-(3-imidazol-1-yl-propyl)-amide Derivative (64): 5-furan-2-yl-isoxazole-3-carboxylic acid benzyl-(3-imidazol-1-yl-propyl)-amide Derivative (65): 5-furan-2-yl-4-methyl-isoxazole-3-carboxylic acid (3-imidazol-1-yl-propyl)-amide Derivative (66): 4-ethyl-5-furan-2-yl-isoxazole-3-carboxylic acid (3-imidazol-1-yl-propyl)-amide Derivative (67): 4-benzyl-5-furan-2-yl-isoxazole-3-carboxylic acid (3-imidazol-1-yl-propyl)-amide Derivative (68): 5-phenyl-isoxazole-3-carboxylic acid (3-imidazol-1-yl-propyl)-amide Derivative (69): 5-phenyl-isoxazole-3-carboxylic acid (2-imidazol-1-yl-ethyl)-amide Derivative (70): 5-phenyl-isoxazole-3-carboxylic acid (2-pyridin-2-yl-ethyl)-amide Derivative (71): 5-phenyl-isoxazole-3-carboxylic acid (2-pyridin-3-yl-ethyl)-amide Derivative (72): 5-phenyl-isoxazole-3-carboxylic acid (2-pyridin-4-yl-ethyl)-amide Derivative (73): 5-phenyl-isoxazole-3-carboxylic acid [2-(4-hydroxy-phenyl)-ethyl]-amide Derivative (74): 5-phenyl-isoxazole-3-carboxylic acid [2-(4-amino-phenyl)-ethyl]-amide Derivative (75): 5-pyridin-2-yl-isoxazole-3-carboxylic acid (3-imidazol-1-yl-propyl)-amide Derivative (76): 5-pyridin-3-yl-isoxazole-3-carboxylic acid (3-imidazol-1-yl-propyl)-amide Derivative (77): 5-pyridin-4-yl-isoxazole-3-carboxylic acid (3-imidazol-1-yl-propyl)-amide Derivative (78): 5-o-tolyl-isoxazole-3-carboxylic acid (3-imidazol-1-yl-propyl)-amide Derivative (79): 5-m-tolyl-isoxazole-3-carboxylic acid (3-imidazol-1-yl-propyl)-amide Derivative (80): 5-p-tolyl-isoxazole-3-carboxylic acid (3-imidazol-1-yl-propyl)-amide Derivative (81): 5-(2-fluoro-phenyl)-isoxazole-3-carboxylic acid (3-imidazol-1-yl-propyl)-amide Derivative (82): 5-(3-fluoro-phenyl)-isoxazole-3-carboxylic acid (3-imidazol-1-yl-propyl)-amide Derivative (83): 5-(4-fluoro-phenyl)-isoxazole-3-carboxylic acid (3-imidazol-1-yl-propyl)-amide Derivative (84): 5-(4-fluoro-phenyl)-isoxazole-3-carboxylic acid (3-[1,2,4]triazol-1-yl-propyl)-amide Derivative (85): 5-(2-fluoro-phenyl)-isoxazole-3-carboxylic acid (2-imidazol-1-yl-ethyl)-amide Derivative (86): 5-(4-fluoro-phenyl)-isoxazole-3-carboxylic acid (2-imidazol-1-yl-ethyl)-amide Derivative (87): 5-(4-fluoro-phenyl)-isoxazole-3-carboxylic acid (2-pyrazol-1-yl-ethyl)-amide Derivative (88): 5-(4-fluoro-phenyl)-isoxazole-3-carboxylic acid (2-[1,2,4]triazol-1-yl-ethyl)-amide Derivative (89): 5-(4-fluoro-phenyl)-isoxazole-3-carboxylic acid (2-[1,2,3]triazol-2-yl-ethyl)-amide Derivative (90): 5-(4-fluoro-phenyl)-isoxazole-3-carboxylic acid (2-[1,2,3]triazol-1-yl-ethyl)-amide Derivative (91): 5-(4-fluoro-phenyl)-isoxazole-3-carboxylic acid (2-tetrazol-2-yl-ethyl)-amide Derivative (92): 5-(3-fluoro-phenyl)-isoxazole-3-carboxylic acid (2-pyridin-4-yl-ethyl)-amide Derivative (93): 5-(4-fluoro-phenyl)-isoxazole-3-carboxylic acid (2-pyridin-4-yl-ethyl)-amide Derivative (94): 5-(3-fluoro-phenyl)-isoxazole-3-carboxylic acid (2-pyridin-3-yl-ethyl)-amide Derivative (95): 5-(4-fluoro-phenyl)-isoxazole-3-carboxylic acid (2-pyridin-3-yl-ethyl)-amide Derivative (96): 5-(4-chloro-phenyl)-isoxazole-3-carboxylic acid (3-[1,2,4]triazol-1-yl-propyl)-amide Derivative (97): 5-(4-chloro-phenyl)-isoxazole-3-carboxylic acid (2-[1,2,4]triazol-1-yl-ethyl)-amide Derivative (98): 5-(4-chloro-phenyl)-isoxazole-3-carboxylic acid (3-imidazol-1-yl-propyl)-amide Derivative (99): 5-(2-methoxy-phenyl)-isoxazole-3-carboxylic acid (3-imidazol-1-yl-propyl)-amide Derivative (100): 5-(3-methoxy-phenyl)-isoxazole-3-carboxylic acid (3-imidazol-1-yl-propyl)-amide Derivative (101): 5-(4-methoxy-phenyl)-isoxazole-3-carboxylic acid (3-imidazol-1-yl-propyl)-amide Derivative (102): 5-(4-methoxy-phenyl)-isoxazole-3-carboxylic acid (2-pyridin-4-yl-ethyl)-amide Derivative (103): 5-(3-methoxy-phenyl)-isoxazole-3-carboxylic acid (2-pyridin-4-yl-ethyl)-amide Derivative (104): 5-(2-methoxy-phenyl)-isoxazole-3-carboxylic acid (2-pyridin-4-yl-ethyl)-amide Derivative (105): 5-(2-hydroxy-phenyl)-isoxazole-3-carboxylic acid (3-imidazol-1-yl-propyl)-amide Derivative (106): 5-(3-hydroxy-phenyl)-isoxazole-3-carboxylic acid (3-imidazol-1-yl-propyl)-amide Derivative (107): 5-(4-hydroxy-phenyl)-isoxazole-3-carboxylic acid (3-imidazol-1-yl-propyl)-amide Derivative (108): 5-(3-hydroxy-phenyl)-isoxazole-3-carboxylic acid (2-pyridin-4-yl-ethyl)-amide Derivative (109): 5-(4-hydroxy-phenyl)-isoxazole-3-carboxylic acid (2-pyridin-4-yl-ethyl)-amide Derivative (110): 5-(3-hydroxy-phenyl)-isoxazole-3-carboxylic acid (2-pyridin-3-yl-ethyl)-amide Derivative (111): 5-(4-hydroxy-phenyl)-isoxazole-3-carboxylic acid (2-pyridin-3-yl-ethyl)-amide Derivative (112): 5-(2-nitro-phenyl)-isoxazole-3-carboxylic acid (3-imidazol-1-yl-propyl)-amide Derivative (113): 5-(3-nitro-phenyl)-isoxazole-3-carboxylic acid (3-imidazol-1-yl-propyl)-amide Derivative (114): 5-(4-nitro-phenyl)-isoxazole-3-carboxylic acid (3-imidazol-1-yl-propyl)-amide Derivative (115): 5-(3-nitro-phenyl)-isoxazole-3-carboxylic acid (2-pyridin-4-yl-ethyl)-amide Derivative (116): 5-(4-nitro-phenyl)-isoxazole-3-carboxylic acid (2-pyridin-4-yl-ethyl)-amide Derivative (117): 5-(3-nitro-phenyl)-isoxazole-3-carboxylic acid (2-pyridin-3-yl-ethyl)-amide Derivative (118): 5-(4-nitro-phenyl)-isoxazole-3-carboxylic acid (2-pyridin-3-yl-ethyl)-amide Derivative (119): 5-(3-amino-phenyl)-isoxazole-3-carboxylic acid (3-imidazol-1-yl-propyl)-amide Derivative (120): 5-(4-amino-phenyl)-isoxazole-3-carboxylic acid (3-imidazol-1-yl-propyl)-amide Derivative (121): 5-(3-amino-phenyl)-isoxazole-3-carboxylic acid (2-pyridin-4-yl-ethyl)-amide Derivative (122): 5-(4-amino-phenyl)-isoxazole-3-carboxylic acid (2-pyridin-4-yl-ethyl)-amide Derivative (123): 5-(3-amino-phenyl)-isoxazole-3-carboxylic acid (2-pyridin-3-yl-ethyl)-amide Derivative (124): 5-(4-amino-phenyl)-isoxazole-3-carboxylic acid (2-pyridin-3-yl-ethyl)-amide Derivative (125): 5-(3-trifluoromethyl-phenyl)-isoxazole-3-carboxylic acid (3-imidazol-1-yl-propyl)-amide Derivative (126): 5-(4-trifluoromethyl-phenyl)-isoxazole-3-carboxylic acid (3-imidazol-1-yl-propyl)-amide Derivative (127): 5-(3-trifluoromethyl-phenyl)-isoxazole-3-carboxylic acid (2-pyridin-4-yl-ethyl)-amide Derivative (128): 5-(4-trifluoromethyl-phenyl)-isoxazole-3-carboxylic acid (2-pyridin-4-yl-ethyl)-amide Derivative (129): 5-(3-trifluoromethyl-phenyl)-isoxazole-3-carboxylic acid (2-pyridin-3-yl-ethyl)-amide Derivative (130): 5-(4-trifluoromethyl-phenyl)-isoxazole-3-carboxylic acid (2-pyridin-3-yl-ethyl)-amide Derivative (131): 5-thiophen-2-yl-isoxazole-3-carboxylic acid (3-imidazol-1-yl-propyl)-amide Derivative (132): 5-(4-fluoro-phenyl)-isoxazole-3-carboxylic acid (3-[1,2,4]-triazol-1-yl-propyl)-amide Derivative (133): 5-thiophen-2-yl-isoxazole-3-carboxylic acid (2-imidazol-1-yl-ethyl)-amide Derivative (134): 5-thiophen-2-yl-isoxazole-3-carboxylic acid (2-pyrazol-1-yl-ethyl)-amide Derivative (135): 5-thiophen-2-yl-isoxazole-3-carboxylic acid (2-[1,2,4]triazol-1-yl-ethyl)-amide Derivative (136): 5-thiophen-2-yl-isoxazole-3-carboxylic acid (2-[1,2,3]triazol-2-yl-ethyl)-amide Derivative (137): 5-thiophen-2-yl-isoxazole-3-carboxylic acid (2-[1,2,3]triazol-1-yl-ethyl)-amide Derivative (138): 5-thiophen-2-yl-isoxazole-3-carboxylic acid (2-pyridin-2-yl-ethyl)-amide Derivative (139): 5-thiophen-2-yl-isoxazole-3-carboxylic acid (2-pyridin-3-yl-ethyl)-amide Derivative (140): 5-thiophen-2-yl-isoxazole-3-carboxylic acid (2-pyridin-4-yl-ethyl)-amide Derivative (141): 5-thiophen-2-yl-isoxazole-3-carboxylic acid [2-(4-hydroxy-phenyl)-ethyl]-amide Derivative (142): 5-thiophen-2-yl-isoxazole-3-carboxylic acid [2-(4-amino-phenyl)-ethyl]-amide Derivative (143): 5-(5-bromo-thiophen-2-yl)-isoxazole-3-carboxylic acid (3-imidazol-1-yl-propyl)-amide Derivative (144): 5-(5-nitro-thiophen-2-yl)-isoxazole-3-carboxylic acid (3-imidazol-1-yl-propyl)-amide Derivative (145): 5-(4-methyl-thiophen-2-yl)-isoxazole-3-carboxylic acid (3-imidazol-1-yl-propyl)-amide Derivative (146): 5-(5-methyl-furan-2-yl)-isoxazole-3-carboxylic acid (3-imidazol-1-yl-propyl)-amide Derivative (147): 5-(5-nitro-furan-2-yl)-isoxazole-3-carboxylic acid (3-imidazol-1-yl-propyl)-amide Derivative (148): 5-(5-amino-furan-2-yl)-isoxazole-3-carboxylic acid (3-imidazol-1-yl-propyl)-amide Derivative (149): 5-(1-methyl-1H-pyrrol-2-yl)-isoxazole-3-carboxylic acid (3-imidazol-1-yl-propyl)-amide Derivative (132): 5-Thiophen-2-yl-isoxazole-3-carboxylic acid-(3-[1,2,4]-triazol-1-yl-propyl)-amide.

Derivative (151): 5-(1-methyl-1H-pyrrol-2-yl)-isoxazole-3-carboxylic acid (2-[1,2,4]triazol-1-yl-ethyl)-amide Derivative (152): 5-furan-3-yl-isoxazole-3-carboxylic acid (3-imidazol-1-yl-propyl)-amide Derivative (153): 5-furan-3-yl-isoxazole-3-carboxylic acid (3-[1,2,4]-triazol-1-yl-propyl)-amide Derivative (154): 5-furan-3-yl-isoxazole-3-carboxylic acid (2-[1,2,4]-triazol-1-yl-ethyl)-amide Derivative (155): 5-thiophen-3-yl-isoxazole-3-carboxylic acid (3-[1,2,4]-triazol-1-yl-propyl)-amide Derivative (156): 5-thiophen-3-yl-isoxazole-3-carboxylic acid (3-imidazol-1-yl-propyl)-amide Derivative (157): 5-thiophen-3-yl-isoxazole-3-carboxylic acid (2-imidazol-1-yl-ethyl)-amide Derivative (158): 5-thiophen-3-yl-isoxazole-3-carboxylic acid (2-[1,2,4]-triazol-1-yl-ethyl)-amide Derivative (159): 5-(1H-pyrrol-2-yl)-isoxazole-3-carboxylic acid (3-[1,2,4]triazol-1-yl-propyl)-amide Derivative (160): 5-(1H-pyrrol-2-yl)-isoxazole-3-carboxylic acid (3-imidazol-1-yl-propyl)-amide Derivative (161): 5-morpholin-4-yl-isoxazole-3-carboxylic acid (3-imidazol-1-yl-propyl)-amide Derivative (162): 5-morpholin-4-yl-isoxazole-3-carboxylic acid (3-[1,2,4]-triazol-1-yl-propyl)-amide Derivative (163): 5-morpholin-4-yl-isoxazole-3-carboxylic acid (2-[1,2,4]-triazol-1-yl-ethyl)-amide Derivative (164): 5-cyclohexyl-3-isoxazole-3-carboxylic acid (3-imidazol-1-yl-propyl)-amide Derivative (165): 5-cyclohexyl-3-isoxazole-3-carboxylic acid (3-[1,2,4]-triazol-1-yl-propyl)-amide Derivative (166): 5-cyclohexyl-3-isoxazole-3-carboxylic acid (2-[1,2,4]-triazol-1-yl-ethyl)-amide Derivative (167): 5-tert-butyl-3-isoxazole-3-carboxylic acid (3-imidazol-1-yl-propyl)-amide Derivative (168): 5-tert-butyl-3-isoxazole-3-carboxylic acid (3-[1,2,4]-triazol-1-yl-propyl)-amide Derivative (169): 5-benzofuran-2-yl-isoxazole-3-carboxylic acid (3-imidazol-1-yl-propyl)-amide Derivative (170): 5-benzofuran-2-yl-isoxazole-3-carboxylic acid (3-[1,2,4]triazol-1-yl-propyl)-amide Derivative (171): 5-benzofuran-2-yl-isoxazole-3-carboxylic acid (2-[1,2,4]triazol-1-yl-ethyl)-amide Derivative (172): benzo[d]isoxazole-3-carboxylic acid (2-pyridin-4-yl-ethyl)-amide Derivative (173): benzo[d]isoxazole-3-carboxylic acid (3-imidazol-1-yl-propyl)-amide Derivative (174): 5-furan-2-yl-isoxazole-3-carboxylic acid (2-piperidin-1-yl-ethyl)-amide Derivative (175): 5-furan-2-yl-isoxazole-3-carboxylic acid (2-morpholin-4-yl-ethyl)-amide Derivative (176): 5-furan-2-yl-isoxazole-3-carboxylic acid (2-piperazin-1-yl-ethyl)-amide Derivative (177): 5-furan-2-yl-isoxazole-3-carboxylic acid [2-(4-methyl-piperazin-1-yl)-ethyl]-amide Derivative (178): 5-furan-2-yl-isoxazole-3-carboxylic acid [2-(4-acetyl-piperazin-1-yl)-ethyl]-amide Derivative (179): 5-furan-2-yl-isoxazole-3-carboxylic acid {2-[4-(4-fluorophenyl)-piperazin-1-yl]-ethyl}-amide Derivative (180): 5-furan-2-yl-isoxazole-3-carboxylic acid {2-[4-(4-nitrophenyl)-piperazin-1-yl]-ethyl}-amide Derivative (181): 5-furan-2-yl-isoxazole-3-carboxylic acid {2-[4-(4-methoxyphenyl)-piperazin-1-yl]-ethyl}-amide Derivative (182): 5-furan-2-yl-isoxazole-3-carboxylic acid [2-(4-pyridin-2-yl-piperazin-1-yl)-ethyl]-amide Derivative (183): 5-furan-2-yl-isoxazole-3-carboxylic acid {2-[4-(4-methylphenyl)-piperazin-1-yl]-ethyl}-amide Derivative (184): 5-furan-2-yl-isoxazole-3-carboxylic acid {2-[4-(4-chlorophenyl)-piperazin-1-yl]-ethyl}-amide Derivative (185): 5-furan-2-yl-isoxazole-3-carboxylic acid {2-[4-(3-methoxyphenyl)-piperazin-1-yl]-ethyl}-amide Derivative (186): 5-furan-2-yl-isoxazole-3-carboxylic acid {2-[4-(3,4-dimethoxyphenyl)-piperazin-1-yl]-ethyl}-amide Derivative (187): 5-furan-2-yl-isoxazole-3-carboxylic acid {2-[4-(2,4-dimethoxyphenyl)-piperazin-1-yl]-ethyl}-amide Derivative (188): 5-furan-2-yl-isoxazole-3-carboxylic acid {2-[4-(3,5-dimethoxyphenyl)-piperazin-1-yl]-ethyl}-amide Derivative (189): 5-furan-2-yl-isoxazole-3-carboxylic acid {2-[4-(3-methoxy-pyridin-2-yl)-piperazin-1-yl]-ethyl}-amide Derivative (190): 5-furan-2-yl-isoxazole-3-carboxylic acid {2-[4-(3-methyl-pyridin-2-yl)-piperazin-1-yl]-ethyl}-amide Derivative (191): 5-furan-2-yl-isoxazole-3-carboxylic acid {2-[4-(3-trifluoromethyl-pyridin-2-yl)-piperazin-1-yl]-ethyl}-amide Derivative (192): 5-furan-2-yl-isoxazole-3-carboxylic acid [2-(4-pyrimidin-2-yl-piperazin-1-yl)-ethyl]-amide Derivative (193): 5-furan-2-yl-isoxazole-3-carboxylic acid {2-[4-(2-methoxyphenyl)-piperazin-1-yl]-ethyl}-amide Derivative (194): 5-furan-2-yl-isoxazole-3-carboxylic acid [2-(4-phenyl-piperazin-1-yl)-ethyl]-amide Derivative (195): 5-furan-2-yl-isoxazole-3-carboxylic acid (2-phenylamino-ethyl)-amide Derivative (196): 5-furan-2-yl-isoxazole-3-carboxylic acid (2-diphenylamino-ethyl)-amide Derivative (197): 5-furan-2-yl-isoxazole-3-carboxylic acid (2-benzylamino-ethyl)-amide Derivative (198): 5-furan-2-yl-isoxazole-3-carboxylic acid [2-(4-chloro-phenylamino)-ethyl]-amide Derivative (199): 5-furan-2-yl-isoxazole-3-carboxylic acid [2-(4-isopropyl-phenylamino)-ethyl]-amide Derivative (200): 5-furan-2-yl-isoxazole-3-carboxylic acid [2-(4-methoxy-phenylamino)-ethyl]-amide Derivative (201): 5-furan-2-yl-isoxazole-3-carboxylic acid (3-phenylamino-propyl)-amide Derivative (202): 5-furan-2-yl-isoxazole-3-carboxylic acid [2-(methyl-phenyl-amino)-ethyl]-amide Derivative (203): 5-furan-2-yl-isoxazole-3-carboxylic acid [3-(methyl-phenyl-amino)-propyl]-amide Derivative (204): 5-furan-2-yl-isoxazole-3-carboxylic acid [2-(pyridin-2-ylamino)-ethyl]-amide Derivative (205): 5-furan-2-yl-isoxazole-3-carboxylic acid (2-oxo-2-phenyl-ethyl)-amide Derivative (206): 5-thiophen-2-yl-isoxazole-3-carboxylic acid (3-oxo-3-phenyl-propyl)-amide Derivative (207): 5-furan-2-yl-isoxazole-3-carboxylic acid phenylcarbamoylmethyl-amide Derivative (208): 5-furan-2-yl-isoxazole-3-carboxylic acid (pyridin-2-ylcarbamoylmethyl)-amide Derivative (209): 5-thiophen-2-yl-isoxazole-3-carboxylic acid (2-phenylcarbamoyl-ethyl)-amide Derivative (210): 5-thiophen-2-yl-isoxazole-3-carboxylic acid (2-benzoylamino-ethyl)-amide Derivative (211): 5-thiophen-2-yl-isoxazole-3-carboxylic acid [2-(3-phenyl-urido)-ethyl]-amide Derivative (212): 5-thiophen-2-yl-isoxazole-3-carboxylic acid [2-(3-phenyl-thioureido)-ethyl]-amide Derivative (213): {2-[(5-thiophen-2-yl-isoxazole-3-carbonyl)-amino]-ethyl}-carbamic acid phenyl ester Derivative (214): 5-furan-2-yl-isoxazole-3-carboxylic acid (2-phenoxy-ethyl)-amide Derivative (215): 5-thiophen-2-yl-isoxazole-3-carboxylic acid (2-phenoxy-ethyl)-amide Derivative (216): 5-furan-2-yl-isoxazole-3-carboxylic acid [2-(pyridin-2-yloxy)-ethyl]-amide Derivative (217): 5-thiophen-2-yl-isoxazole-3-carboxylic acid [2-(pyridin-2-yloxy)-ethyl]-amide Derivative (218): 5-thiophen-2-yl-isoxazole-3-carboxylic acid (2-phenylsulfanyl-ethyl)-amide Derivative (219): 5-thiophen-2-yl-isoxazole-3-carboxylic acid (2-benzenesulfonyl-ethyl)-amide Derivative (220): 5-thiophen-2-yl-isoxazole-3-carboxylic acid (2-phenylsulfamoyl-ethyl)-amide Derivative (221): (4-pyridin-2-yl-piperazin-1-yl)-(5-thiophen-2-yl-isoxazol-3-yl)-methanone Derivative (222): (4-pyrimidin-2-yl-piperazin-1-yl)-(5-thiophen-2-yl-isoxazol-3-yl)-methanone Derivative (223): (4-pyrrolidin-1-yl-piperidin-1-yl)-(5-thiophen-2-yl-isoxazol-3-yl)-methanone Derivative (224): (5-furan-2-yl-isoxazol-3-yl)-(4-imidazol-1-yl-piperidin-1-yl)-methanone Derivative (225): N-(5-furan-2-yl-isoxazol-3-yl)-3-pyridin-2-yl-acrylamide Derivative (226): N-(5-furan-2-yl-isoxazol-3-yl)-3-pyridin-3-yl-acrylamide Derivative (227): N-(5-furan-2-yl-isoxazol-3-yl)-3-pyridin-4-yl-acrylamide Derivative (228): N-(5-furan-2-yl-isoxazol-3-yl)-3-pyridin-2-yl-propionamide Derivative (229): N-(5-furan-2-yl-isoxazol-3-yl)-3-pyridin-3-yl-propionamide Derivative (230): N-(5-furan-2-yl-isoxazol-3-yl)-3-pyridin-4-yl-propionamide Derivative (231): N-(5-furan-2-yl-isoxazol-3-yl)-2-pyridin-4-yl-acetamide Derivative (232): N-(5-furan-2-yl-isoxazol-3-yl)-3-phenyl-propionamide Derivative (233): N-(5-furan-2-yl-isoxazol-3-ylmethyl)-2-phenyl-acetamide Derivative (234): N-(5-furan-2-yl-isoxazol-3-ylmethyl)-2-pyridin-4-yl-acetamide Derivative (235): N-(5-furan-2-yl-isoxazol-3-ylmethyl)-3-pyridin-2-yl-acrylamide Derivative (236): N-(5-furan-2-yl-isoxazol-3-ylmethyl)-3-pyridin-3-yl-acrylamide Derivative (237): N-(5-furan-2-yl-isoxazol-3-ylmethyl)-3-pyridin-4-yl-acrylamide Derivative (238): N-(5-furan-2-yl-isoxazol-3-ylmethyl)-3-pyridin-2-yl-propionamide Derivative (239): N-(5-furan-2-yl-isoxazol-3-ylmethyl)-3-pyridin-3-yl-propionamide Derivative (240): N-(5-furan-2-yl-isoxazol-3-ylmethyl)-3-pyridin-4-yl-propionamide Derivative (241): 1-benzyl-3-(5-furan-2-yl-isoxazol-3-yl)-urea Derivative (242): 1-(5-furan-2-yl-isoxazol-3-yl)-3-pyridin-2-ylmethyl-urea Derivative (243): 1-(5-furan-2-yl-isoxazol-3-yl)-3-pyridin-3-ylmethyl-urea Derivative (244): 1-(5-furan-2-yl-isoxazol-3-yl)-3-pyridin-4-ylmethyl-urea Derivative (245): 1-(5-phenyl-isoxazol-3-yl)-3-pyridin-2-yl-methyl-urea Derivative (246): 1-(5-phenyl-isoxazol-3-yl)-3-pyridin-3-yl-methyl-urea Derivative (247): 1-(5-phenyl-isoxazol-3-yl)-3-pyridin-4-yl-methyl-urea Derivative (248): 1-pyridin-2-ylmethyl-3-(5-thiophen-2-yl-isoxazol-3-yl)-urea:

Derivative (249): 1-pyridin-3-ylmethyl-3-(5-thiophen-2-yl-isoxazol-3-yl)-urea

Derivative (250): 1-pyridin-4-ylmethyl-3-(5-thiophen-2-yl-isoxazol-3-yl)-urea

Derivative (251): imidazole-1-carboxylic acid 5-furan-2-yl-isoxazol-3-ylmethyl ester Derivative (252): 4-acetyl-piperazine-1-carboxylic acid 5-furan-2-yl-isoxazol-3-ylmethyl ester Derivative (253): 4-methyl-piperazine-1-carboxylic acid 5-furan-2-yl-isoxazol-3-ylmethyl ester Derivative (254): pyridin-4-ylmethyl-carbamic acid 5-furan-2-yl-isoxazol-3-ylmethyl ester Meanwhile, in accordance with another aspect, the present invention provides a method for preparing an isoxazole derivative represented by Chemical Formula 1.

It is recognized that on the basis of the method of the present invention, those skilled in the art may easily prepare isoxazole derivatives of Chemical Formula 1 using well-known compounds or readily obtainable compounds therefrom. Hence, the following explanations of the method are nothing but illustrative techniques in which process orders may be changed optionally, and thus are not intended to limit the present invention.

Firstly, general processes for synthesizing the substituent, the isoxazole derivatives of Chemical Formula 1, in which X is represented by Chemical Formula 2 or 3 (that is, the isoxazole derivatives of Chemical Formula 18 or 19) are depicted in the following Reaction Formula 1.

Reaction Formula 1

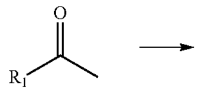

1

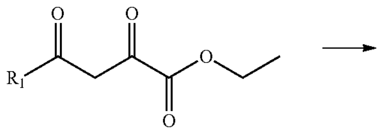

2

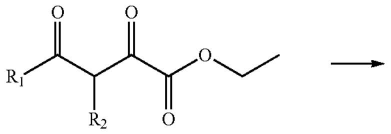

3

-continued

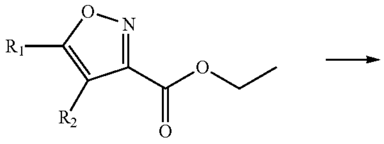

4

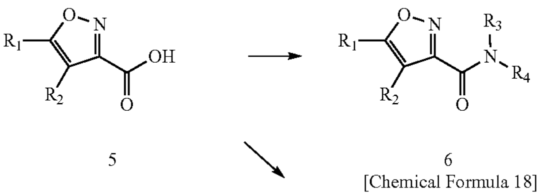

5

6

[Chemical Formula 18]

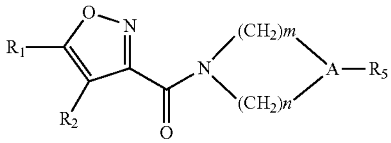

7

[Chemical Formula 19]

A starting material 1, commercially available, is treated, preferably with 1.0 M sodium ethoxide in absolute ethanol, and then reacted with diethyl oxalate to produce an intermediate 2. In DMF, the intermediate 2 is reacted with alkyl halide in the presence of sodium hydride to give an intermediate 3 having an alkyl group. Subsequently, the intermediate 3 produces an isoxazole intermediate 4 using hydroxylamine in absolute ethanol. This intermediate 4 is converted into a carboxylic acid intermediate 5, preferably using 1N lithium hydroxide in THF and methanol. Finally, the intermediate 5 is reacted with a desired amine to synthesize an isoxazole compound 6 (represented by Chemical Formula 18) or 7 (represented by Chemical Formula 19).

Next, General processes for synthesizing the substituent, the isoxazole derivatives of Chemical Formula 1, in which X is represented by Chemical Formula 4, 5 or 6, that is, the compounds of Chemical Formula 20, 21 or 22, are depicted in the following Reaction Formula 2.

Reaction Formula 2

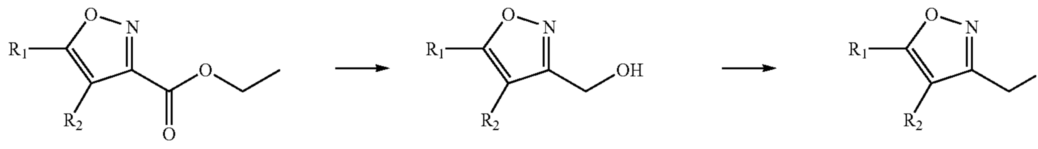

4 8 10

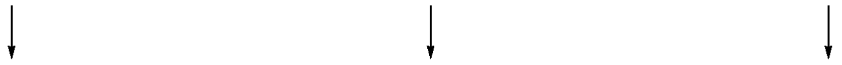

-continued

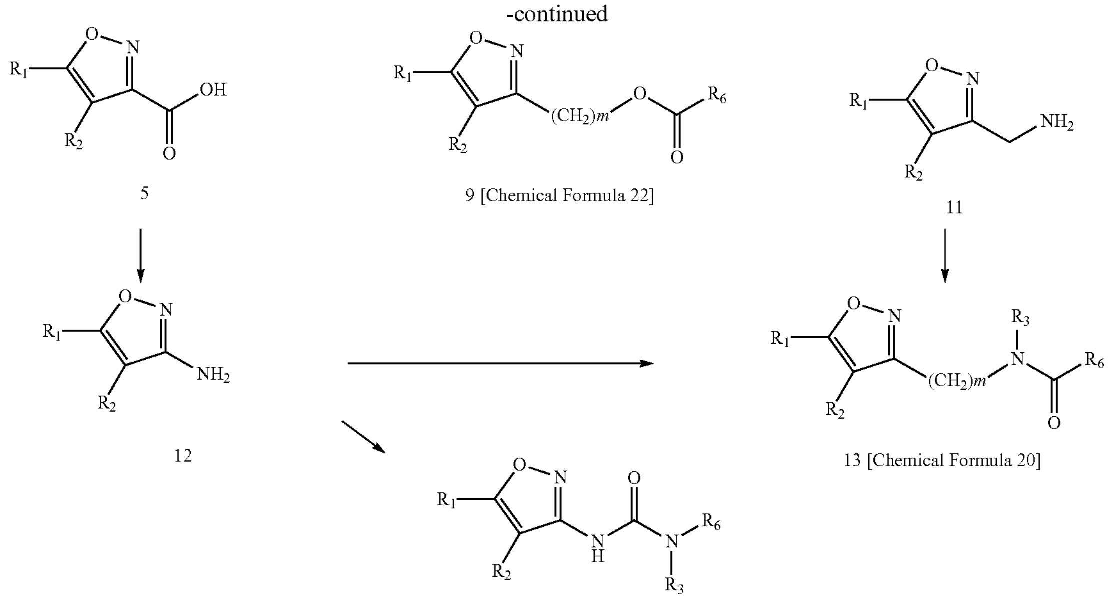

5

9 [Chemical Formula 22]

11

12

13 [Chemical Formula 20]

14 [Chemical Formula 21]

The intermediates 4 and 5 can be obtained as described in Reaction Formula 1. subsequently, Reaction of the intermediate 5 with DPPA results in an amine intermediate 12, which is then reacted with a desired carboxylic acid to synthesize a final isoxazole compound 13 (corresponding to Chemical Formula 20). In another reaction route, the intermediate 4 is converted into an alcohol intermediate 8 in the presence of sodiumborohydride in ethanol. This alcohol intermediate 8 is then treated with methanesulfonylchloride and triethyl amine, followed by reaction with sodium azide to obtain an intermediate 10. Afterwards, the intermediate 10 is hydrogenated in the presence of a palladium catalyst to give an amine intermediate 11, which is reacted with a desired carboxylic acid to afford a final isoxazole compound 13 (corresponding to Chemical Formula 20).

The intermediate 12 can be reacted with CDI and a desired amine to produce a final isoxazole compound 14 (corresponding to Chemical Formula 21).

In the meanwhile, the intermediate 8 can also be reacted with CDI and a desired amine to produce a final isoxazole compound 9 (corresponding to Chemical Formula 22).

As will be understood from the Experimental Examples, described later, the compounds of Chemical Formula 1 have the ability to activate Wnt/β-catenin signaling. In accordance with a further aspect, therefore, the present invention pertains to a composition capable of activating Wnt/β-catenin signaling, comprising a therapeutically effective amount of an isoxazole derivative represented by Chemical Formula 1 or a pharmaceutically acceptable salt thereof, and a pharmaceutically acceptable carrier.

For the preparation of the above pharmaceutical compound, a dosage can be formed by the isoxazole derivative of Chemical Formula 1, serving as an active ingredient, being mixed in a suitable ratio with a carrier selected depending on the dosage form.

That is, according to the administration routes, the active ingredient may be formulated into oral, parenteral, injection and transdermal agents. preferably Unit dosage forms are produced in terms of ease of administration and dosage uniformity.

An oral dosage form of the isoxazole derivatives may be prepared with conventional pharmaceutical carriers. For example, water, glycol, oil, and/or alcohol may be used as carriers in orally ingestible liquids, such as suspensions, syrups, and elixirs. As for solid orally ingested forms, such as powders, pills, capsules and tablets, they may be prepared with carriers, such as starch, sugar, caolin, lubricants, binders, and/or disintegrants. Taking ease of administration into consideration, tablets and capsules are the most convenient. Tablets and pills are preferably prepared as enteric coated preparations.

Usually, parenteral dosage forms comprise sterile water as a carrier, and optionally, other component such as a dissolution aid.

Injection preparations, such as aqueous or oil suspensions for sterile injection, may be prepared by using appropriate dispersing agents, wetting agents, or suspending agents in accordance with known techniques. Solvents which may be used include water, Ringers solution and isotonic NaCl solution. Sterile fixing oil is also usually used as a solvent or a suspension medium. Non-irritating fixing oils, including mono- or di-glycerides, may be used for this purpose. Also, fatty acids such as oleic acid are used in injection preparations.

For the transdermal preparations, appropriate penetration promoters and/or wetting agents may be used in combination with non-irritating additives. Anything may be used as an additive if it is useful for promoting the delivery of the active ingredient through the skin or for preparing a desired composition, with no particular limitations imposed thereon. The transdermal preparations may be administrated in various form of patches, creams, or ointments.

In the meantime, in order to prevent the rapid in vivo removal of the active ingredients according to the present invention, the compositions thereof may be formulated into prolonged release forms. In this regard, for example, implants, microencapsulated delivery systems, and biodegradable/biocompatible polymers may be used as carriers.

The term "therapeutically effective amount" as used herein means an amount of the active ingredient that is effective for alleviating or reducing symptoms of the diseases to be treated or for inhibiting or retarding the onset of clinical markers or symptoms of the diseases to be prevented. The therapeutically effective amount may be empirically determined by testing the corresponding compound against the disease in in vivo and in vitro model systems.

When the active ingredient according to the present invention, that is, an isoxazole derivative of Chemical Formula 1, is administered for a clinical purpose, the preferred total daily dose to be administered to a host, whether all at once or in multiple doses, is on the order of 0.1 mg to 10 mg per kg of body weight. However, the specific dosage level for specific patients may vary depending on the specific compound to be used, body weight, sex, health status, diet, time of administration, method of administration, rate of excretion, drug combination, and severity of disease.

Optionally, the isoxazole derivatives of Chemical Formula 1 may be formulated into prodrug forms.

The composition for activating Wnt/β-catenin signaling according to the present invention may further comprise other additives, which have no inhibitory effect on, or have a supplementary effect on, the activity of the active ingredients, and may be formulated in various forms.

In accordance with still a further aspect, the present invention provides a pharmaceutical composition comprising the isoxazole derivative of Chemical Formula 1 as an effective ingredient to activate Wnt/β-catenin signaling to regulate the differentiation of stem cells, whereby the composition is effective in the treatment and prevention of diseases relevant to Wnt/β-catenin signaling.

Examples of the diseases may include osteoporosis and osteoarthropathy.

MODE FOR INVENTION

A better understanding of the present invention may be obtained in light of the following examples which are set forth to illustrate, but are not to be construed to limit the present invention.

Preparation Example 1

Preparation of 5-Furan-2-yl-isoxazole-3-carboxylic acid (3-imidazol-1-yl-propyl)-amide 5-Furan-2-yl-isoxazole-3-carboxylic acid (3-imidazol-1-yl-propyl)-amide (Derivative 1) was prepared via the route depicted in the following Reaction Formula 3. This reaction route will be described in more detail according to process steps below.

Reaction Formula 3

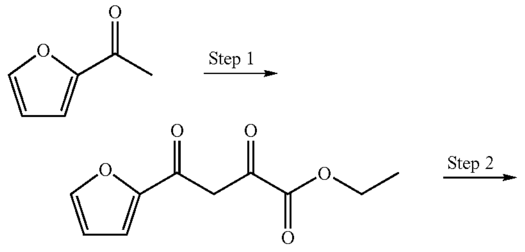

-continued

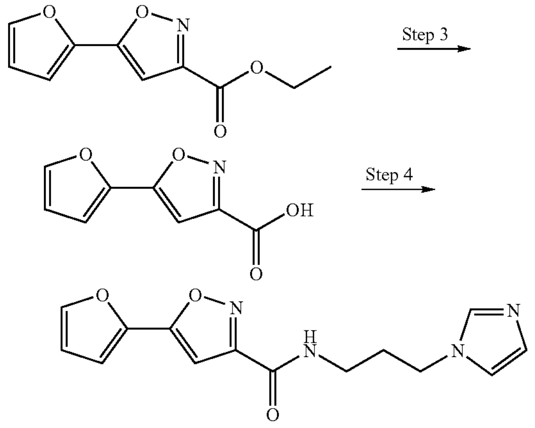

1) Step 1: Preparation of 4-Furan-2-yl-2,4-dioxo-butyl acid ethyl ester 2-acetylfuran was slowly added to a solution of sodium ethoxide (6.81 g) dissolved in absolute ethanol (200 mL) at 0° C. (5.01 mL). This solution was stirred at 0° C. for 2 hrs before oxalic acid diethyl ester (9.30 mL) was slowly added thereto. After stirring for 18 hrs, the reaction was terminated with 1N HCl. The resulting solution was concentrated under reduced pressure to remove the ethanol, followed by extraction with methylene chloride. The organic layer was dried over anhydrous sodium sulfate, filtered, and concentrated in vacuo to afford 10.0 g of 4-furan-2-yl-2,4-dioxo-butyric acid ethyl ester. This concentrate was used in the next step without further purification.

1H-NMR (acetone-$d_6$, 200 MHz), ppm(δ): 8.02~7.99 (m, 1H), 7.62~7.55 (m, 1H), 6.98~6.94 (m, 1H), 6.83~6.77 (m, 1H), 4.40 (q, 2H), 1.38 (t, 3H)

2) Step 2: Preparation of 5-furan-2-yl-isoxazole-3-carboxylic acid ethyl ester After a suspension of 10.0 g of 4-furan-2-yl-2,4-dioxo-butyric ethyl ester prepared above and hydroxylamine hydrochloride was stirred at 85° C. for 2 hrs, the solvent was removed under reduced pressure. The concentrate was dissolved in a mixture of methylene chloride and distilled water, followed by separating the organic layer. The organic layer was dried over anhydrous sodium sulfate, filtered through a silica gel layer, and concentrated in vacuo to produce a yield of 8.01 g of 5-furan-2-yl-isoxazole-3-carboxylic acid ethyl ester (Yield 77%). The concentrate was used in the next step without further purification.

1H-NMR (acetone-$d_6$, 200 MHz), ppm(δ): 7.90~7.86 (m, 1H), 7.20 (d, 1H), 7.00 (s, 1H), 6.77~6.73 (m, 1H), 4.45 (q, 2H), 1.41 (t, 3H)

3) Step 3: Preparation of 5-furan-2-yl-isoxazole-3-carboxylic acid 4.14 g of 5-furan-2-yl-isoxazole-3-carboxylic acid ethyl ester was dissolved in 130 mL of THF 130 mL and 25 mL of methanol before the slow addition of 80 mL of aqueous 1N lithium hydroxide. Stirring for 15 hrs was followed by the removal of THF and methanol under reduced pressure. The residue was acidified with 1N HCl to produce a precipitate which was then filtered, washed with distilled water and dried to produce 3.22 g of 5-furan-2-yl-isoxazole-3-carboxylic acid as a white solid (Yield: 90%).

1H-NMR (acetone-$d_6$, 200 MHz), ppm(δ): 7.90~7.86 (m, 1H), 7.19 (d, 1H), 7.00 (s, 1H), 6.77~6.73 (m, 1H)

4) Step 4: Preparation of 5-furan-2-yl-isoxazole-3-carboxylic acid (3-imidazol-1-yl-propyl)-amide (Derivative (1))

To a solution of 5-furan-2-yl-isoxazole-3-carboxylic acid (7 mg) and 3-imidazol-1-yl-propyl amine (0.005 mL) in DMF was added 8 mg of HOBt, 9 mg of EDC and 0.014 mL of TEA. After stirring at room temperature for 18 hrs, the reaction solution was concentrated in vacuo. The obtained concentrate was purified by preparative HPLC to afford 4 mg of 5-furan-2-yl-isoxazole-3-carboxylic acid (3-imidazol-1-yl-propyl)-amide (Yield: 35%).

1H-NMR (acetone-$d_6$, 200 MHz), ppm(δ): 8.16 (bs, 1H), 7.86~7.84 (m, 1H), 7.65~7.61 (m, 1H), 7.19~7.12 (m, 2H), 6.97~6.89 (m, 2H), 6.78~6.71 (m, 1H), 4.18 (t, 2H), 3.48 (q, 2H), 2.24~2.07 (m, 2H) Exact Mass (calc.): 286.11 LC-MS (ESI+) m/e (M+1)+: 287.

From suitable starting materials, the following Derivatives (2)~(224) were prepared in processes similar to those for the isoxazole derivative (1), and the results are given in Tables 1 to 29, below.

TABLE 1

| Cpd. No. | Structure | Results |
|---|---|---|
| 2 | 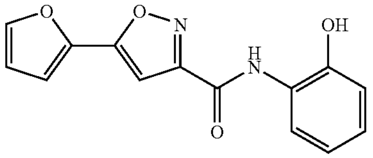 | $^1$H-NMR(DMSO-$d_6$, 200 MHz), ppm(δ): 9.75(bs, 1H), 8.04~7.90(m, 2H), 7.33~7.21(m, 2H), 7.08~6.72(m, 5H) Exact Mass (calc.): 270.06 LC-MS (ESI+) m/e $(M + 1)^+$: 271 |
| 3 | 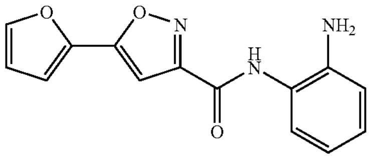 | $^1$H-NMR(DMSO-d6, 200 MHz), ppm(δ): 8.02~7.98(m, 1H), 7.75(bs, 1H), 7.34~7.16(m, 3H), 7.06~6.96(m, 1H), 6.65~6.54(m, 1H), 4.99(s, 2H) Exact Mass (calc.): 269.08 LC-MS (ESI+) m/e $(M + 1)^+$: 270 |
| 4 | 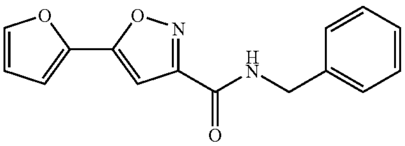 | $^1$H-NMR(acetone-$d_6$, 200 MHz), ppm(δ): 8.47(bs, 1H), 7.89~7.84(m, 1H), 7.47~7.24(m, 5H), 7.22~7.14(m, 1H), 6.96(s, 1H), 6.76~6.71(m, 1H), 4.64(d, 2H) Exact Mass (calc.): 268.08 LC-MS (ESI+) m/e $(M + 1)^+$: 269 |
| 5 | 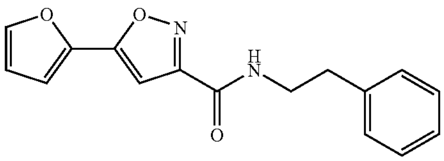 | $^1$H-NMR(acetone-$d_6$, 200 MHz), ppm(δ): 7.98(bs, 1H), 7.89~7.85(m, 1H), 7.39~7.13(m, 6H), 6.92(s, 1H), 6.77~6.71(m, 1H), 3.69(q, 2H), 2.99(t, 2H) Exact Mass (calc.): 282.10 LC-MS (ESI+) m/e $(M + 1)^+$: 283 |
| 6 | 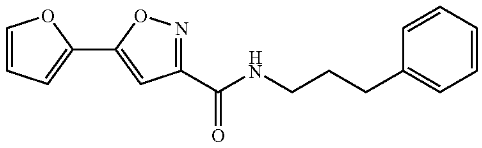 | $^1$H-NMR(acetone-$d_6$, 200 MHz), ppm(δ): 8.15~7.83(m, 2H), 7.35~7.10(m, 6H), 6.92(s, 1H), 6.77~6.70(m, 1H), 3.49(q, 2H), 2.78(t, 2H), 2.10~1.90(m, 2H) Exact Mass (calc.): 296.12 LC-MS (ESI+) m/e $(M + 1)^+$: 297 |
| 7 | 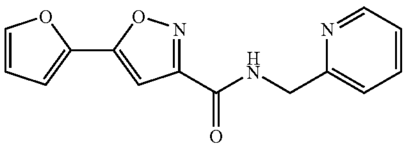 | $^1$H-NMR(acetone-$d_6$, 200 MHz), ppm(δ): 8.62~8.52(m, 2H), 7.90~7.75(m, 2H), 7.49~7.42(m, 1H), 7.36~7.26(m, 1H), 7.21~7.17(m, 1H), 6.98(s, 1H), 6.78~6.72(m, 1H), 4.75(d, 2H) Exact Mass(calc.): 269.08 LC-MS (ESI+) m/e $(M + 1)^+$: 270 |
| 8 | 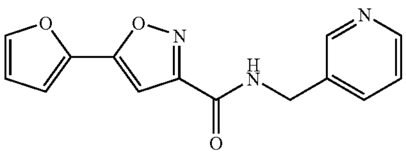 | $^1$H-NMR(acetone-$d_6$, 200 MHz), ppm(δ): 8.69~8.48(m, 3H), 7.89~7.80(m, 2H), 7.41~7.32(m, 1H), 7.19~7.15(m, 1H), 6.96(s, 1H), 6.76~6.71(m, 1H), 4.68(d, 2H) Exact Mass(calc.): 269.08 LC-MS (ESI+) m/e $(M + 1)^+$: 270 |

TABLE 2

| | | |
|---|---|---|
| 9 | 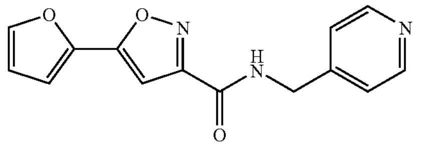 | $^1$H-NMR(acetone-$d_6$, 200 MHz), ppm(δ): 8.67(bs, 1H), 8.59~8.52(m, 2H), 7.90~7.86(m, 1H), 7.41~7.35(m, 2H), 7.20~7.15(m, 1H), 6.98(s, 1H), 6.75~6.70(m, 1H), 4.69(d, 2H) Exact Mass(calc.): 269.08 LC-MS (ESI+) m/e $(M + 1)^+$: 270 |
| 10 | 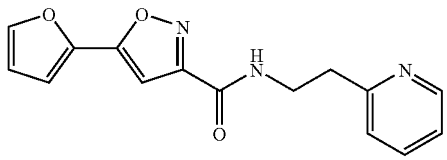 | $^1$H-NMR(acetone-$d_6$, 200 MHz), ppm(δ): 8.78~8.06(m, 2H), 8.00~7.53(m, 2H), 7.50~6.60(m, 5H), 3.83(q, 2H), 3.14(t, 2H) Exact Mass (calc.): 283.10 LC-MS (ESI+) m/e $(M + 1)^+$: 284 |
| 11 | 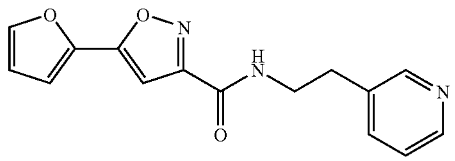 | $^1$H-NMR(acetone-$d_6$, 200 MHz), ppm(δ): 8.56~8.42(m, 2H), 8.09(bs, 1H), 7.88~7.84(m, 1H), 7.75~7.67(m, 1H), 7.35~7.26(m, 1H), 7.18~7.13(m, 1H), 6.91(s, 1H), 6.76~6.71(m, 1H), 3.73(q, 2H), 3.02(t, 2H) Exact Mass (calc.): 283.10 LC-MS (ESI+) m/e $(M + 1)^+$: 284 |
| 12 | 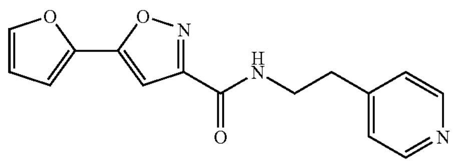 | $^1$H-NMR(acetone-$d_6$, 200 MHz), ppm(δ): 8.53~8.48(m, 2H), 8.05(bs, 1H), 7.88~7.83(m, 1H), 7.33~7.25(m, 2H), 7.17~7.14(m, 1H), 6.91(s, 1H), 6.75~6.70(m, 1H), 3.75(q, 2H), 3.02(t, 2H) Exact Mass (calc.): 283.10 LC-MS (ESI+) m/e $(M + 1)^+$: 284 |
| 13 | 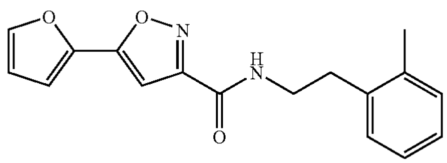 | Exact Mass (calc.): 296.12 LC-MS (ESI+) m/e $(M + 1)^+$: 297 |
| 14 | 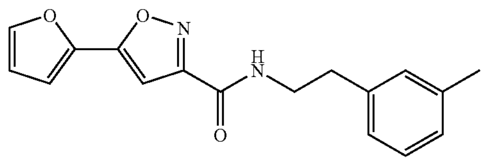 | Exact Mass (calc.): 296.12 LC-MS (ESI+) m/e $(M + 1)^+$: 297 |
| 15 | 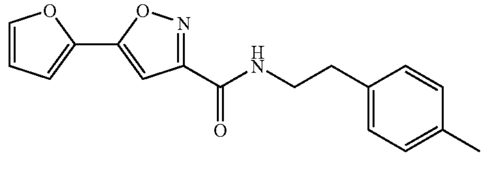 | $^1$H-NMR(acetone-$d_6$, 200 MHz), ppm(δ): 8.01~7.90(m, 1H), 7.88~7.85(m, 1H), 7.22~7.10(m, 5H), 6.92(s, 1H), 6.75~6.72(m, 1H), 3.65(q, 2H), 2.93(t, 2H), 2.31(s, 3H) Exact Mass (calc.): 296.12 LC-MS (ESI+) m/e $(M + 1)^+$: 297 |
| 16 | 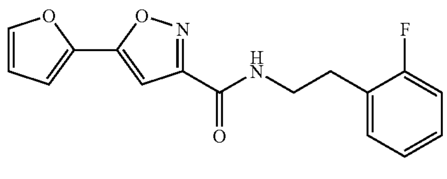 | $^1$H-NMR(acetone-$d_6$, 200 MHz), ppm(δ): 8.05(bs, 1H), 7.87~7.84(m, 1H), 7.43~7.23(m, 2H), 7.19~7.06(m, 3H), 6.74(s, 1H)), 6.75~6.71(m, 1H), 3.71(q, 2H), 3.04(t, 2H) Exact Mass (calc.): 300.09 LC-MS (ESI+) m/e $(M + 1)^+$: 301 |

TABLE 3

| | | |
|---|---|---|
| 17 | 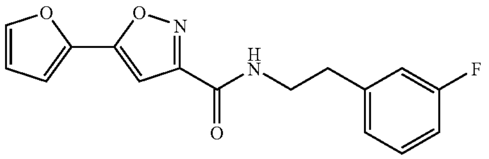 | $^{1}$H-NMR(acetone-$d_6$, 200 MHz), ppm(δ): 7.99(bs, 1H), 7.89~7.84(m, 1H), 7.43~7.30(m, 1H), 7.19~6.95(m, 4H), 6.91(s, 1H)), 6.77~6.70(m, 1H), 3.71(q, 2H), 3.04(t, 2H) Exact Mass (calc.): 300.09 LC-MS (ESI+) m/e $(M + 1)^+$: 301 |
| 18 | 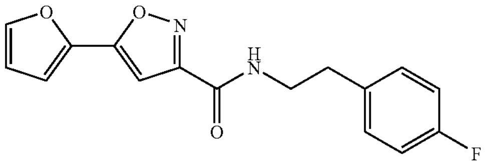 | $^{1}$H-NMR(acetone-$d_6$, 200 MHz), ppm(δ): 7.98(bs, 1H), 7.87~7.84(m, 1H), 7.41~7.28(m, 2H), 7.18~7.02(m, 3H), 6.91(s, 1H)), 6.75~6.70(m, 1H), 3.68(q, 2H), 2.98(t, 2H) Exact Mass (calc.): 300.09 LC-MS (ESI+) m/e $(M + 1)^+$: 301 |
| 19 | 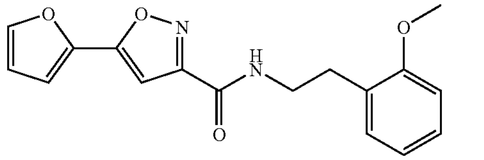 | Exact Mass (calc.): 312.11 LC-MS (ESI+) m/e $(M + 1)^+$: 313 |
| 20 | 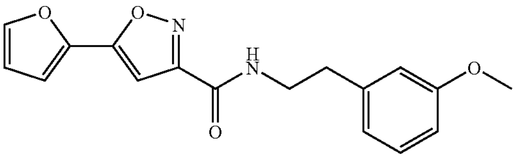 | $^{1}$H-NMR(acetone-$d_6$, 200 MHz), ppm(δ): 8.01~7.80(m, 2H), 7.29~7.14(m, 2H), 6.92~6.71(m, 5H), 3.80(s, 3H), 3.69(q, 2H), 2.96(t, 2H) Exact Mass (calc.): 312.11 LC-MS (ESI+) m/e $(M + 1)^+$: 313 |
| 21 | 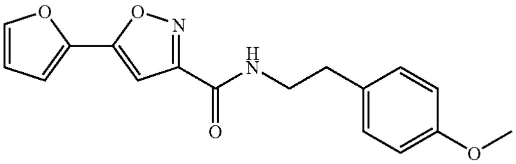 | $^{1}$H-NMR(acetone-$d_6$, 200 MHz), ppm(δ): 7.96~7.82(m, 2H), 7.26~7.14(m, 3H), 6.94~6.85(m, 3H), 6.75~6.71(m, 1H), 3.79(s, 3H), 3.64(q, 2H), 2.91(t, 2H) Exact Mass (calc.): 312.11 LC-MS (ESI+) m/e $(M + 1)^+$: 313 |
| 22 | 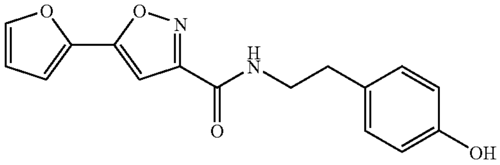 | $^{1}$H-NMR(acetone-$d_6$, 200 MHz), ppm(δ): 8.04~7.78(m, 2H), 7.18~7.08(m, 3H), 6.91(s, 1H), 6.84~6.72(m, 3H), 3.62(q, 2H), 2.87(t, 2H) Exact Mass (calc.): 298.10 LC-MS (ESI+) m/e $(M + 1)^+$: 299 |
| 23 | 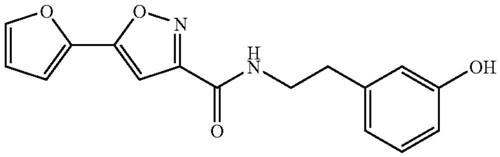 | 1H-NMR(acetone-$d_6$, 200 MHz), ppm(δ): 8.26(bs, 1H), 7.97(bs, 1H), 7.89~7.85(m, 1H), 7.21~7.11(m, 2H), 6.92(s, 1H), 6.82~6.65(m, 4H), 3.72~3.60(m, 2H), 2.94(t, J = 4.80, 2H) Exact Mass (calc.): 298.30 LC-MS (ESI+) m/e (M + 1)+: 299 |

TABLE 4

| | | |
|---|---|---|
| 24 | 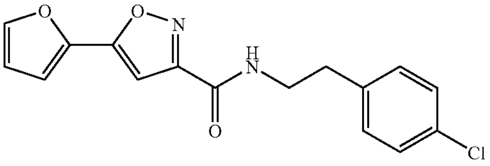 | $^{1}$H-NMR(acetone-$d_6$, 200 MHz), ppm(δ): 8.02(bs, 1H), 7.88~7.85(m, 1H), 7.36~7.26(m, 4H), 7.18~7.14(m, 1H), 6.91(s, 1H), 6.78~6.72(m, 1H), 3.68 (q, 2H), 2.99(t, 2H) Exact Mass (calc.): 316.06 LC-MS (ESI+) m/e $(M + 1)^+$: 317 |

TABLE 4-continued

| | | |
|---|---|---|
| 25 | 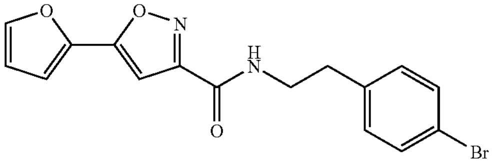 | Exact Mass (calc.): 360.01 LC-MS (ESI+) m/e $(M + 1)^+$: 361 |
| 26 | 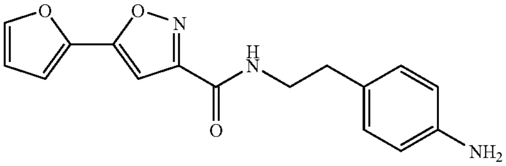 | $^1$H-NMR(acetone-$d_6$, 200 MHz), ppm(δ): 7.88~7.84(m, 2H), 7.17~7.13(m, 1H), 7.03~6.96(m, 2H), 6.91(s, 1H), 6.76~6.71(m, 1H), 6.67~6.60(m, 1H), 3.59(q, 2H), 2.80(t, 2H) Exact Mass (calc.): 297.11 LC-MS (ESI+) m/e $(M + 1)^+$: 298 |
| 27 | 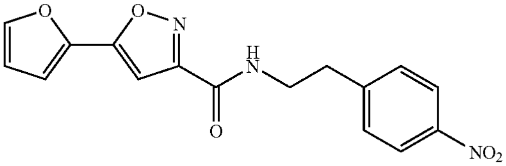 | $^1$H-NMR(acetone-$d_6$, 200 MHz), ppm(δ): 8.26~8.19(m, 1H), 8.08(bs, 1H), 7.88~7.84(m, 1H), 7.66~7.57(m, 2H), 7.18~7.14(m, 1H), 6.90(s, 1H), 6.76~6.72(m, 1H), 3.78(q, 2H), 3.17(t, 2H) Exact Mass (calc.): 327.09 LC-MS (ESI+) m/e $(M + 1)^+$: 328 |
| 28 | 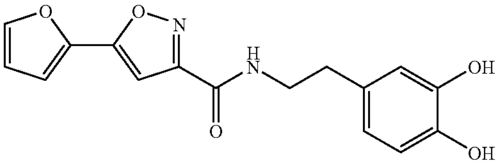 | $^1$H-NMR(acetone-$d_6$, 200 MHz), ppm(δ): 8.01~7.87(m, 4H), 7.18~7.14(m, 1H), 6.92(s, 1H), 6.81~6.58(m, 4H), 3.63(q, 2H), 2.82(t, 2H) Exact Mass (calc.): 314.09 LC-MS (ESI+) m/e $(M + 1)^+$: 315 |
| 29 | 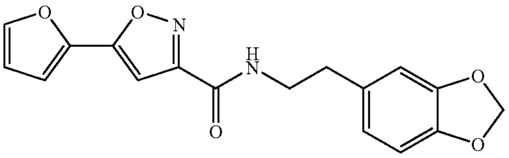 | $^1$H-NMR(acetone-$d_6$, 200 MHz), ppm(δ): 8.01~7.82(m, 2H), 7.18~7.14(m, 1H), 6.92(s, 1H), 6.86~6.71(m, 4H), 5.98(s, 2H), 3.65(q, 2H), 2.90(t, 2H) Exact Mass (calc.): 326.09 LC-MS (ESI+) m/e $(M + 1)^+$: 327: |
| 30 | 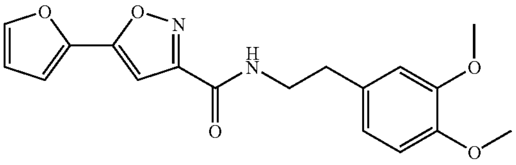 | $^1$H-NMR(acetone-$d_6$, 200 MHz), ppm(δ): 7.99~7.80(m, 2H), 7.18~7.14(m, 1H), 6.94~6.78(m, 4H), 6.74~6.71(m, 1H), 3.82(s, 3H), 3.79(s, 3H), 3.66(q, 2H), 2.91(t, 2H) Exact Mass (calc.): 342.12 LC-MS (ESI+) m/e $(M + 1)^+$: 343 |
| 31 | 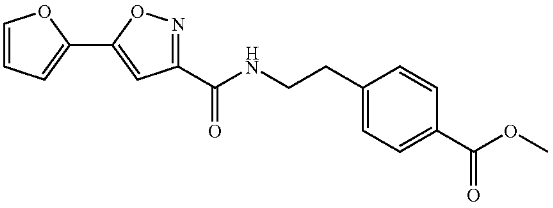 | Exact Mass (calc.): 340.11 LC-MS (ESI+) m/e $(M + 1)^+$: 341 |

TABLE 5

| | | |
|---|---|---|
| 32 | 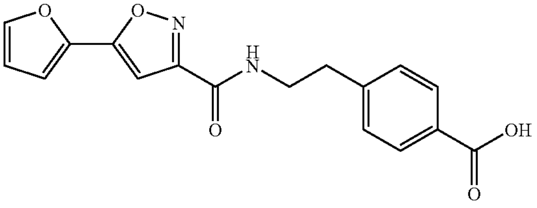 | Exact Mass (calc.): 326.09 LC-MS (ESI+) m/e $(M + 1)^+$: 327 |

TABLE 5-continued

| | | |
|---|---|---|
| 33 | 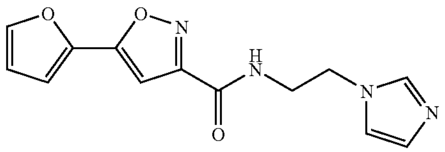 | $^1$H-NMR(acetone-$d_6$, 200 MHz), ppm(δ): 8.20(bs, 1H), 7.91~7.84(m, 1H), 7.63~7.54(m, 1H), 7.22~7.12(m, 2H), 6.98~6.88(m, 2H), 6.78~6.70(m, 1H), 4.34(t, 2H), 3.82(q, 2H) Exact Mass (calc.): 272.09 LC-MS (ESI+) m/e $(M + 1)^+$: 273 |
| 34 | 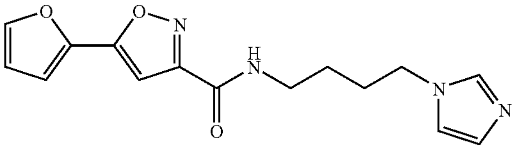 | $^1$H-NMR(acetone-$d_6$, 200 MHz), ppm(δ): 8.06(bs, 1H), 7.88~7.83(m, 1H), 7.62~7.55(m, 1H), 7.18~7.07(m, 2H), 6.80~6.89(m, 1H), 6.92(s, 1H), 6.77~6.70(m, 1H), 4.16(t, 2H), 3.46(q, 2H), 2.11~1.82(m, 2H), 1.79~1.58(m, 2H) Exact Mass (calc.): 300.12 LC-MS (ESI+) m/e $(M + 1)^+$: 301 |
| 35 | 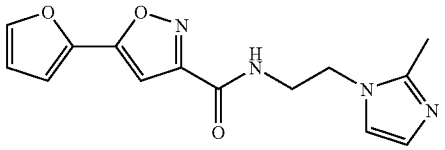 | $^1$H-NMR(acetone-$d_6$, 200 MHz), ppm(δ): 8.25(bs, 1H), 7.88~7.85(m, 1H), 7.18~7.16(m, 1H), 7.02~6.97(m, 1H), 6.93(s, 1H), 6.76~6.71(m, 2H), 4.21(t, 2H), 3.77(q, 2H), 2.34(s, 3H) Exact Mass (calc.): 286.11 LC-MS (ESI+) m/e $(M + 1)^+$: 287 |
| 36 | 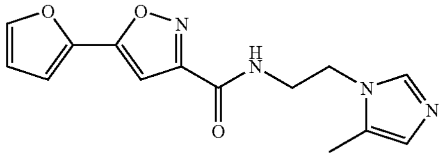 | $^1$H-NMR(acetone-$d_6$, 200 MHz), ppm(δ): 8.22(bs, 1H), 7.89~7.84(m, 1H), 7.45~7.38(m, 1H), 7.19~7.13(m, 1H), 6.93(s, 1H), 6.76~6.71(m, 1H), 6.65~6.61(m, 1H), 4.24(t, 2H), 3.74(q, 2H), 2.25(s, 3H) Exact Mass (calc.): 286.11 LC-MS (ESI+) m/e $(M + 1)^+$: 287 |
| 37 | 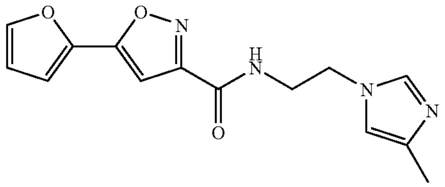 | $^1$H-NMR(acetone-$d_6$, 200 MHz), ppm(δ): 8.22(bs, 1H), 7.89~7.84(m, 1H), 7.45~7.38(m, 1H), 7.19~7.13(m, 1H), 6.93(s, 1H), 6.86~6.82(m, 1H), 6.76~6.71(m, 1H), 4.24(t, 2H), 3.74(q, 2H), 2.10(s, 3H) Exact Mass (calc.): 286.11 LC-MS (ESI+) m/e $(M + 1)^+$: 287 |

TABLE 6

| | | |
|---|---|---|
| 38 | 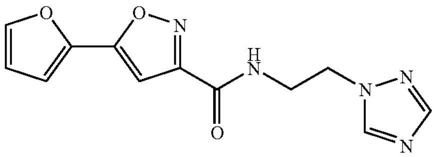 | $^1$H-NMR(acetone-$d_6$, 200 MHz), ppm(δ): 8.40(s, 1H), 8.20(bs, 1H), 7.91~7.83(m, 2H), 7.18~7.16(m, 1H), 6.92(s, 1H), 6.76~6.71(m, 1H), 4.54(t, 2H), 3.90(q, 2H) Exact Mass (calc.): 273.09 LC-MS (ESI+) m/e $(M + 1)^+$: 274 |
| 39 | 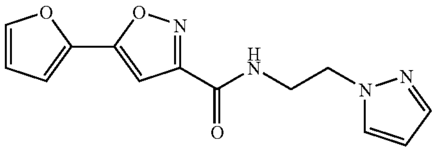 | $^1$H-NMR(acetone-$d_6$, 200 MHz), ppm(δ): 8.14(bs, 1H), 7.89~7.85(m, 1H), 7.71~7.66(m, 1H), 7.49~7.44(m, 1H), 7.19~7.14(m, 1H), 6.93(s, 1H), 6.76~6.72(m, 1H), 6.28~6.22(m, 1H), 4.45(t, J = 5.80, 2H), 3.92~3.81(m, 2H) Exact Mass (calc.): 272.26 LC-MS (ESI+) m/e (M + 1)+: 273 |
| 40 | 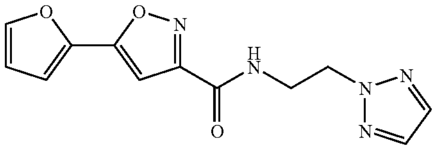 | $^1$H-NMR(acetone-$d_6$, 200 MHz), ppm(δ): 8.13(bs, 1H), 7.89~7.84(m, 1H), 7.71(s, 2H), 7.19~7.14(m, 1H), 6.92(s, 1H), 6.76~6.72(m, 1H), 4.74(t, J = 5.80, 2H), 4.01~3.90(m, 2H) Exact Mass (calc.): 273.25 LC-MS (ESI+) m/e (M + 1)+: 274 |
| 41 | 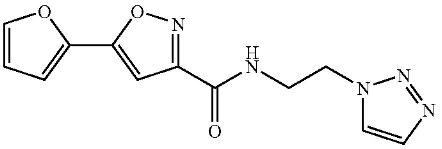 | $^1$H-NMR(acetone-$d_6$, 200 MHz), ppm(δ): 8.20(bs, 1H), 8.03s, 1H), 7.89~7.84(m, 1H), 7.67(s, 1H), 7.19~7.14(m, 1H), 6.92(s, 1H), 6.76~6.72(m, 1H), 4.74(t, J = 5.80, 2H), 4.01~3.91(m, 2H) Exact Mass (calc.): 273.25 LC-MS (ESI+) m/e (M + 1)+: 274 |

TABLE 6-continued

| | | |
|---|---|---|
| 42 | 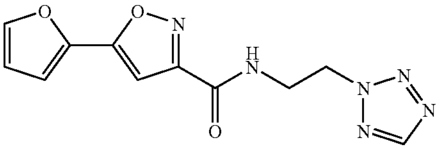 | $^{1}$H-NMR(acetone-$d_6$, 200 MHz), ppm(δ): 8.74(s, 1H), 8.24(bs, 1H), 7.89~7.85(m, 1H), 7.19~7.14(m, 1H), 6.91(s, 1H), 6.76~6.72(m, 1H), 5.02(t, J = 5.80, 2H), 4.25~3.99(m, 2H) Exact Mass (calc.): 274.24 LC-MS (ESI+) m/e (M + 1)+: 275 |
| 43 | 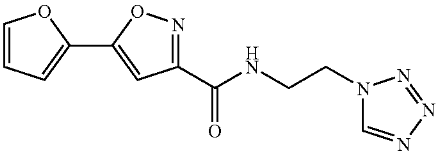 | $^{1}$H-NMR(DMSO-$d_6$, 200 MHz), ppm(δ): 9.41(s, 1H), 9.04(t, J = 5.40, 1H), 8.01~7.94(m, 1H), 7.38~7.23(m, 1H), 7.03(s, 1H), 6.78~6.72(m, 1H), 4.66(t, J = 5.40, 2H), 3.72(q, J = 5.40, 2H) Exact Mass (calc.): 274.24 LC-MS (ESI+) m/e (M + 1)+: 275 |

TABLE 7

| | | |
|---|---|---|
| 44 | 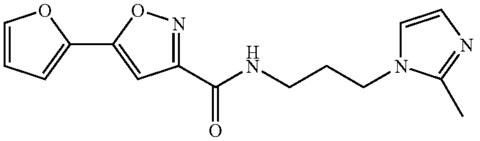 | $^{1}$H-NMR(acetone-$d_6$, 200 MHz), ppm(δ): 8.15(bs, 1H), 7.89~7.80(m, 1H), 7.19~7.14(m, 1H), 7.10~7.04(m, 1H), 6.94(s, 1H), 6.79~6.71(m, 2H), 4.06(t, J = 6.00, 2H), 3.57~3.43(m, 2H), 2.33(s, 3H), 2.19~2.07(m, 2H) Exact Mass (calc.): 300.32 LC-MS (ESI+) m/e (M + 1)+: 301 |
| 45 | 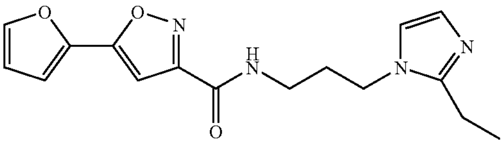 | Exact Mass (calc.): 314.14 LC-MS (ESI+) m/e $(M + 1)^+$: 315 |
| 46 | 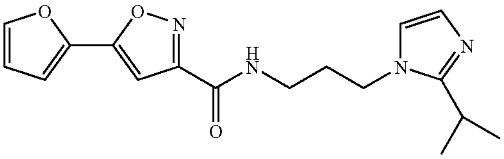 | Exact Mass (calc.): 328.15 LC-MS (ESI+) m/e $(M + 1)^+$: 329 |
| 47 | 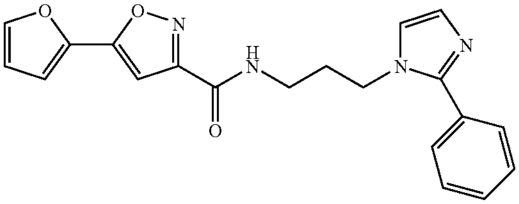 | Exact Mass (calc.): 362.14 LC-MS (ESI+) m/e $(M + 1)^+$: 363 |
| 48 | 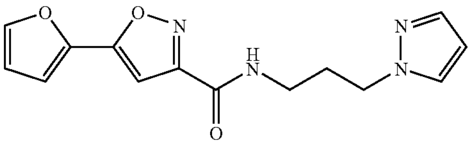 | $^{1}$H-NMR(acetone-$d_6$, 200 MHz), ppm(δ): 8.08(bs, 1H), 7.89~7.84(m, 1H), 7.74~7.67(m, 1H), 7.47~7.42(m, 1H), 7.19~7.14(m, 1H), 6.93(s, 1H), 6.76~6.71(m, 1H), 6.26~6.22(m, 1H), 4.30(t, J = 7.00, 2H), 3.52~3.40(m, 2H), 2.27~2.11(m, 2H) Exact Mass (calc.): 286.29 LC-MS (ESI+) m/e (M + 1)+: 287 |
| 49 | 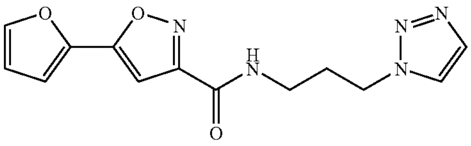 | $^{1}$H-NMR(DMSO-$d_6$, 200 MHz), ppm(δ): 8.92(bs, 1H), 8.16~8.12(m, 1H), 7.987~7.94(m, 1H), 7.71~7.67(m, 1H), 7.25~7.20(m, 1H), 7.04(s, 1H), 6.79~6.71(m, 1H), 4.41(t, J = 6.00, 2H), 3.27~3.21(m, 2H), 2.10~2.02(m, 2H) Exact Mass (calc.): 287.28 LC-MS (ESI+) m/e (M + 1)+: 288 |
| 50 | 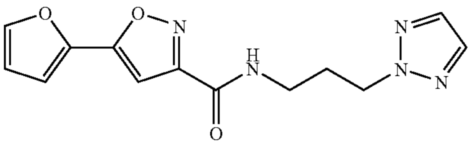 | $^{1}$H-NMR(DMSO-$d_6$, 200 MHz), ppm(δ): 9.00~8.95(m, 1H), 7.98(s, 1H), 7.77(s, 1H), 7.23(m, 1H), 7.04(s, 1H), 6.74(m, 1H), 4.47(t, 2H), 3.29~3.25(m, 2H), 2.20~2.05(m, 2H) Exact Mass (calc.): 287.10 LC-MS (ESI+) m/e (M + 1)+: 288 |

TABLE 7-continued

| | | |
|---|---|---|
| 51 | 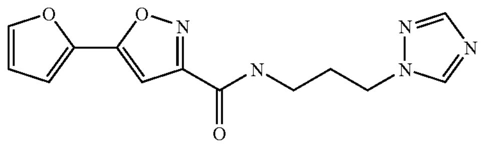 | $^1$H-NMR(DMSO-$d_6$, 200 MHz), ppm(δ): 9.00~8.95(m, 1H), 8.51(s, 1H), 7.97(m, 2H), 7.24(m, 1H), 7.06(s, 1H), 6.75(m, 1H), 4.23(t, 2H), 3.30~3.20(m, 2H), 2.10~2.04(m, 2H) Exact Mass (calc.): 287.10 LC-MS (ESI+) m/e (M + 1)+: 288 |

TABLE 8

| | | |
|---|---|---|
| 52 | 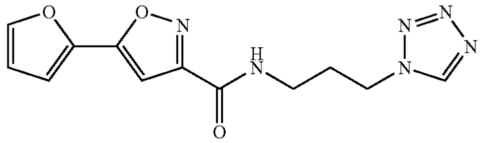 | $^1$H-NMR(DMSO-$d_6$, 200 MHz), ppm(δ): 9.39(s, 1 H), 9.00~8.95(m, 1 H), 7.97(s, 1 H), 7.23(m, 1 H), 7.05(s, 1 H), 6.74(m, 1 H), 4.50(t, 2 H), 3.29~3.25(m, 2 H), 2.15~2.08(m, 2 H) Exact Mass (calc.): 288.10 LC-MS (ESI+) m/e (M + 1)+: 289 |
| 53 | 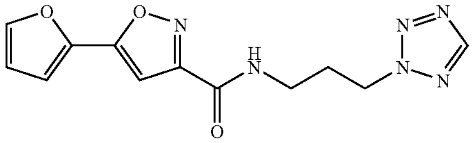 | $^1$H-NMR(DMSO-$d_6$, 200 MHz), ppm(δ): 8.96(m, 2 H), 7.97(s, 1 H), 7.24(s, 1 H), 7.06(s, 1 H), 6.80~6.70(m, 1 H), 4.80~4.64(m, 2 H), 3.29~3.25(m, 2 H), 2.22~2.05(m, 2 H) Exact Mass (calc.): 288.10 LC-MS (ESI+) m/e (M + 1)+: 289 |
| 54 | 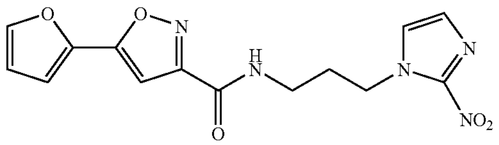 | Exact Mass (calc.): 331.09 LC-MS (ESI+) m/e $(M + 1)^+$: 332 |
| 55 | 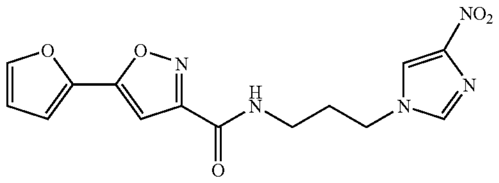 | Exact Mass (calc.): 331.09 LC-MS (ESI+) m/e $(M + 1)^+$: 332 |
| 56 | 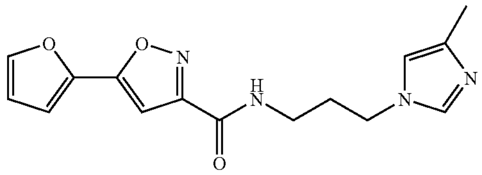 | $^1$H-NMR(acetone-$d_6$, 200 MHz), ppm(δ): 8.18(bs, 1 H), 7.89~7.84(m, 1 H), 7.19~7.14(m, 1 H), 7.09~7.04(m, 1 H), 6.94(s, 1 H), 6.79~6.71(m, 2 H), 4.06(t, J = 7.40, 2 H), 3.57~3.43(m, 2 H), 2.32(s, 3 H), 2.21~2.07(m, 2 H); Exact Mass (calc.): 300.32 LC-MS (ESI+) m/e (M + 1)+: 301 |
| 57 | 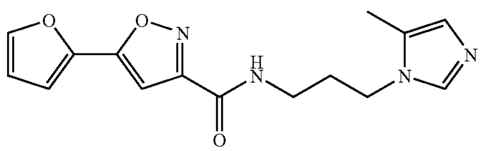 | Exact Mass (calc.): 300.12 LC-MS (ESI+) m/e $(M + 1)^+$: 301 |
| 58 | 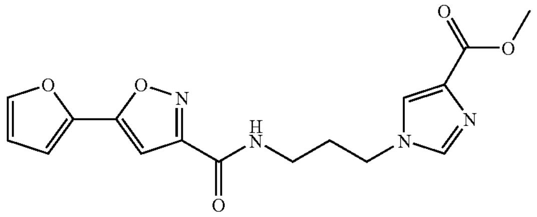 | Exact Mass (calc.): 344.11 LC-MS (ESI+) m/e $(M + 1)^+$: 345 |

TABLE 8-continued

| | | |
|---|---|---|
| 59 | 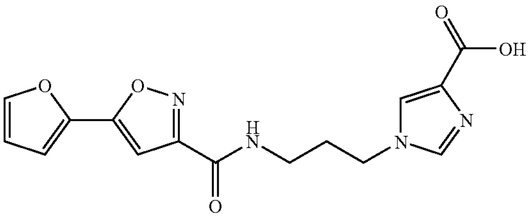 | Exact Mass (calc.): 330.10 LC-MS (ESI+) m/e $(M + 1)^+$: 331 |
| 60 | 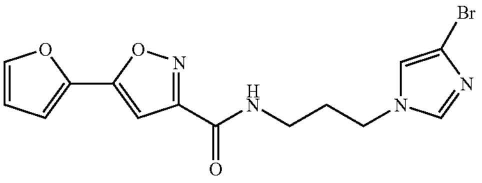 | Exact Mass (calc.): 364.02 LC-MS (ESI+) m/e $(M + 1)^+$: 365 |
| 61 | 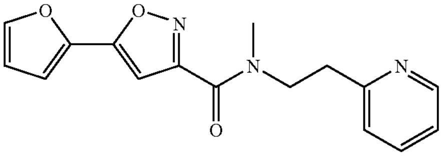 | $^1$H-NMR(acetone-$d_6$, 200 MHz), ppm(δ): 8.58~8.43(m, 1 H), 7.88~7.84(m, 1 H), 7.78~7.63(m, 1 H), 7.39~7.12(m, 3 H), 6.82~6.58(m, 2 H), 4.06~3.90(m, 2 H), 3.21~3.05(m, 5 H) Exact Mass (calc.): 297.11 LC-MS (ESI+) m/e $(M + 1)^+$: 298 |
| 62 | 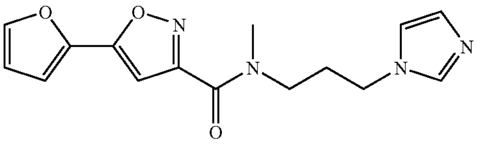 | Exact Mass (calc.): 300.12 LC-MS (ESI+) m/e $(M + 1)^+$: 301 |

TABLE 9

| | | |
|---|---|---|
| 63 | 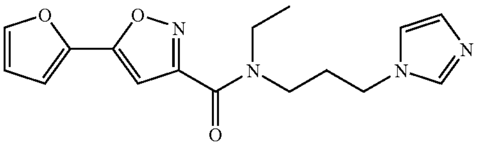 | Exact Mass (calc.): 314.14 LC-MS (ESI+) m/e $(M + 1)^+$: 315 |
| 64 | 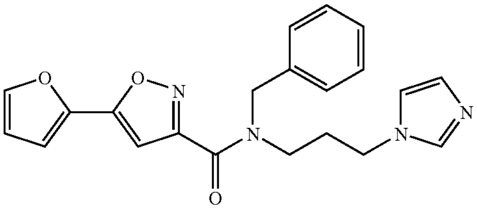 | Exact Mass (calc.): 376.15 LC-MS (ESI+) m/e $(M + 1)^+$: 377 |
| 65 | 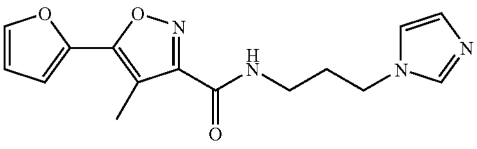 | $^1$H-NMR(acetone-$d_6$, 200 MHz), ppm(δ): 8.06(bs, 1 H), 7.88~7.85(m, 1 H), 7.64~7.60(m, 1 H), 7.19~7.17(m, 1 H), 7.06~7.02(m, 1 H), 6.95(s, 1 H), 6.75~6.69(m, 1 H), 4.18(t, 2 H), 3.47(q, 2 H), 2.45(s, 3 H), 2.24~2.01(m, 2 H) Exact Mass (calc.): 300.12 LC-MS (ESI+) m/e $(M + 1)^+$: 301 |
| 66 | 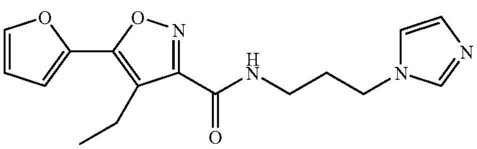 | Exact Mass (calc.): 314.14 LC-MS (ESI+) m/e $(M + 1)^+$: 315 |

TABLE 9-continued

| | | |
|---|---|---|
| 67 | 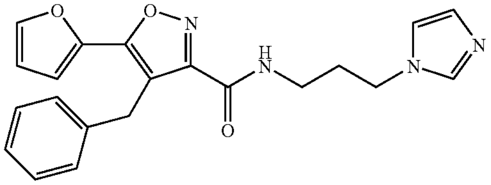 | Exact Mass (calc.): 376.15 LC-MS (ESI+) m/e $(M + 1)^+$: 377 |
| 68 | 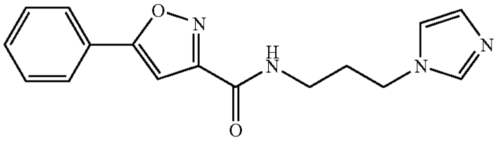 | $^1$H-NMR(acetone-$d_6$, 200 MHz), ppm(δ): 8.17(bs, 1 H), 8.01~7.92(m, 2 H), 7.69~7.53(m, 4 H), 7.24~7.17(m, 2 H), 7.01~6.73(m, 1 H), 4.19(t, 2 H), 3.47(q, 2 H), 2.24~2.06(m, 2 H) Exact Mass (calc.): 296.13 LC-MS (ESI+) m/e $(M + 1)^+$: 297 |
| 69 | 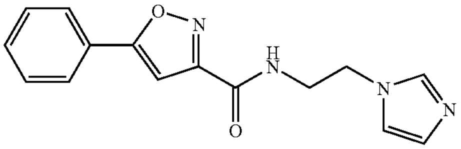 | NMR(acetone-d6, 200 MHz), ppm(δ): 8.15(bs, 1 H), 7.99~7.91(m, 2 H), 7.62~7.50(m, 4 H), 7.19~7.12(m, 2 H), 6.93~6.86(m, 1 H), 4.34(t, J = 5.80, 2 H), 3.87~3.77(m, 2 H) Exact Mass (calc.): 282.30 LC-MS (ESI+) m/e (M + 1)+: 283 |
| 70 | 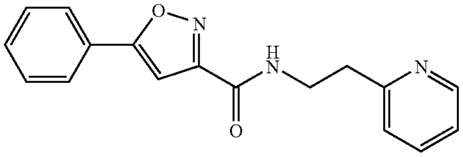 | Exact Mass (calc.): 293.12 LC-MS (ESI+) m/e $(M + 1)^+$: 294 |
| 71 | 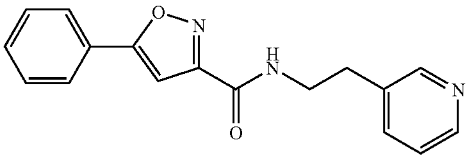 | $^1$H-NMR(acetone-$d_6$, 200 MHz) ppm(δ): 8.57~8.44(m, 2 H), 8.14~7.88(m, 3 H), 7.76~7.52(m, 4 H), 7.36~7.27(m, 2 H), 7.17(s, 1 H), 3.73(q, 2 H), 3.02(t, 2 H) Exact Mass (calc.): 293.13 LC-MS (ESI+) m/e $(M + 1)^+$: 294 |

TABLE 10

| | | |
|---|---|---|
| 72 | 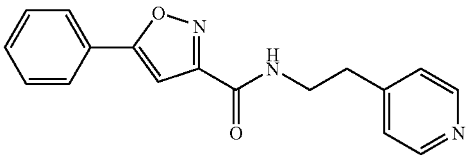 | $^1$H-NMR(acetone-$d_6$, 200 MHz), ppm(δ): 8.58~8.43(m, 2 H), 8.19~7.84(m, 3 H), 7.64~7.49(m, 3 H), 7.37~7.15(m, 2 H), 7.17(s, 1 H), 3.76(q, 2 H), 3.01(t, 2 H) Exact Mass (calc.): 293.12 LC-MS (ESI+) m/e $(M + 1)^+$: 294 |
| 73 | 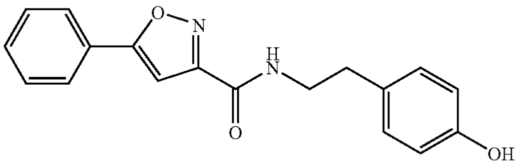 | $^1$H-NMR(acetone-$d_6$, 200 MHz), ppm(δ): 8.21(bs, 1 H), 8.10~7.88(m, 3 H), 7.63~7.51(m, 3 H), 7.19~7.08(m, 3 H), 6.86~6.77(m, 2 H), 3.63(q, 2 H), 2.92(t, 2 H) Exact Mass (calc.): 308.12 LC-MS (ESI+) m/e $(M + 1)^+$: 309 |
| 74 | 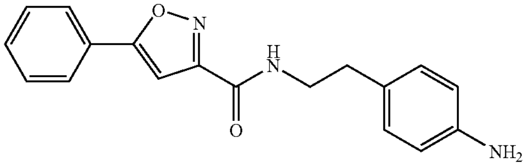 | Exact Mass (calc.): 307.13 LC-MS (ESI+) m/e $(M + 1)^+$: 308 |
| 75 | 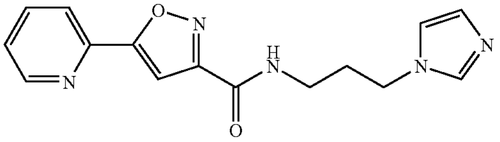 | Exact Mass (calc.): 297.12 LC-MS (ESI+) m/e $(M + 1)^+$: 398 |

TABLE 10-continued

| | | |
|---|---|---|
| 76 | 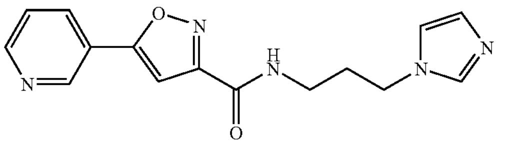 | Exact Mass (calc.): 297.12 LC-MS (ESI+) m/e $(M + 1)^+$: 398 |
| 77 | 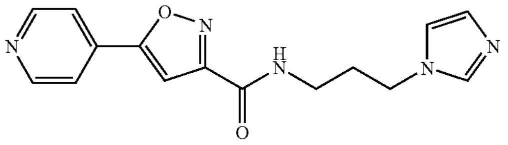 | Exact Mass (calc.): 297.12 LC-MS (ESI+) m/e $(M + 1)^+$: 298 |
| 78 | 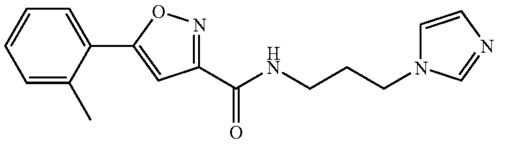 | $^1$H-NMR(acetone-$d_6$, 200 MHz), ppm(δ): 8.12(bs, 1 H), 7.83~7.76(m, 1 H), 7.66~7.62(m, 1 H), 7.48~7.36(m, 3 H), 7.22~7.18(m, 1 H), 7.01~6.93(m, 2 H), 4.19(t, 2 H), 3.50(q, 2 H), 2.56(s, 3 H), 2.25~2.13(m, 2 H) Exact Mass (calc.): 310.14 LC-MS (ESI+) m/e $(M + 1)^+$: 311 |
| 79 | 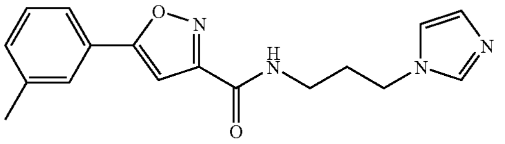 | $^1$H-NMR(acetone-$d_6$, 200 MHz), ppm(δ): 8.15(bs, 1 H), 7.82~7.62(m, 3 H), 7.52~7.34(m, 2 H), 7.23~7.15(m, 2 H), 6.98~6.74(m, 1 H), 4.19(t, 2 H), 3.49(q, 2 H), 2.45(s, 3 H), 2.43~2.05(m, 2 H) Exact Mass (calc.): 310.14 LC-MS (ESI+) m/e $(M + 1)^+$: 311 |
| 80 | 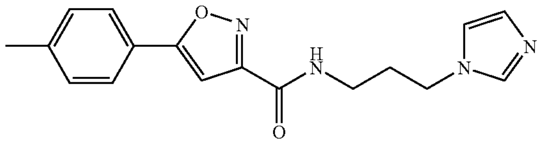 | $^1$H-NMR(acetone-$d_6$, 200 MHz), ppm(δ): 8.10(bs, 1 H), 7.88~7.81(m, 2 H), 7.66~7.62(m, 1 H), 7.45~7.36(m, 2 H), 7.22~7.17(m, 1 H), 7.11(s, 1 H), 6.95~6.40(m, 1 H), 4.18(t, 2 H), 3.48(q, 2 H), 2.43(s, 3 H), 2.25~2.03(m, 2 H) Exact Mass (calc.): 310.14 LC-MS (ESI+) m/e $(M + 1)^+$: 311 |

TABLE 11

| | | |
|---|---|---|
| 81 | 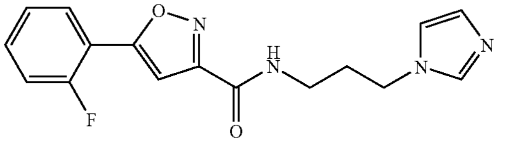 | $^1$H-NMR(acetone-$d_6$, 200 MHz), ppm(δ): 8.25~7.96(m, 2 H), 7.72~7.35(m, 4 H), 7.26~6.91(m, 3 H), 4.20(t, 2 H), 3.50(q, 2 H), 2.24~2.07(m, 2 H) Exact Mass (calc.): 314.12 LC-MS (ESI+) m/e $(M + 1)^+$: 315 |
| 82 | 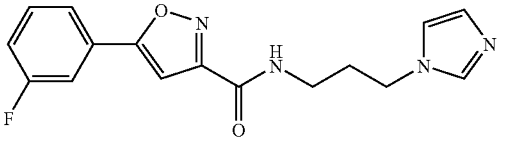 | $^1$H-NMR(acetone-$d_6$, 200 MHz), ppm(δ): 8.26~7.06(m, 1 H), 7.9~7.54(m, 4 H), 7.44~7.12(m, 3 H), $^1$H-NMR(acetone-$d_6$, 200 MHz), ppm(δ): 7.06~6.76(m, 1 H), 4.20(t, 2 H), 3.50(q, 2 H), 2.24~2.07(m, 2 H) Exact Mass (calc.): 314.12 LC-MS (ESI+) m/e $(M + 1)^+$: 31 |
| 83 | 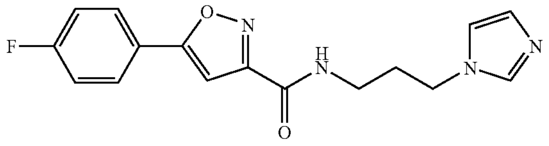 | $^1$H-NMR(acetone-$d_6$, 200 MHz), ppm(δ): 8.21~7.95(m, 2 H), 7.67~7.58(m, 1 H), 7.44~7.28(m, 2 H), 7.24~7.12(m, 1 H), 6.94(s, 1 H), 4.17(t, 2 H), 3.48(q, 2 H), 2.23~2.06(m, 2 H) Exact Mass (calc.): 314.12 LC-MS (ESI+) m/e $(M + 1)^+$: 315 |
| 84 | 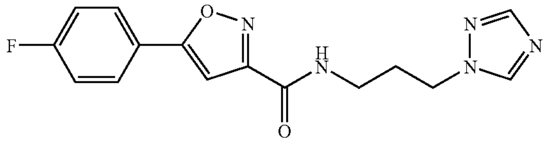 | $^1$H-NMR(DMSO-$d_6$, 200 MHz), ppm(δ): 8.97~8.92(m, 1 H), 8.51(s, 1 H), 8.02~7.95(m, 3 H), 7.43~7.34(m, 3 H), 4.21(t, 2 H), 3.29~.322(m, 2 H), 2.02(m, 2 H) Exact Mass (calc.): 315.11 LC-MS (ESI+) m/e (M + 1)+: 316 |

TABLE 11-continued

| | | |
|---|---|---|
| 85 | 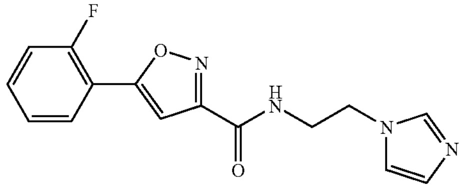 | $^1$H-NMR(acetone-$d_6$, 200 MHz), ppm(δ): 8.26(bs, 1 H), 8.07~7.96(m, 1 H), 7.72~7.35(m, 4 H), 7.19~7.04(m, 2 H), 6.92(s, 1 H), 4.35(t, J = 6.00, 2 H), 3.88~3.76(m, 2 H) Exact Mass (calc.): 300.29 LC-MS (ESI+) m/e (M + 1)+: 301 |
| 86 | 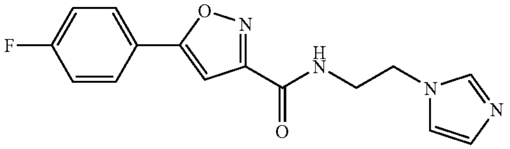 | $^1$H-NMR(acetone-$d_6$, 200 MHz), ppm(δ): 8.15(bs, 1 H), 8.09~7.96(m, 2 H), 7.57(s, 1 H), 7.44~7.30(m, 2 H), 7.19~7.08(m, 2 H), 6.92(s, 1 H), 4.34(t, J = 5.80, 2 H), 3.88~3.75(m, 2 H) Exact Mass (calc.): 300.29 LC-MS (ESI+) m/e (M + 1)+: 301 |
| 87 | 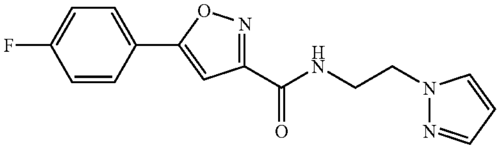 | $^1$H-NMR(DMSO-$d_6$, 200 MHz), ppm(δ): 8.95(m, 1 H), 7.99(m, 2 H), 7.70(s, 1 H), 7.44~7.34(m, 4 H), 6.22(m, 1 H), 4.31(t, 2 H), 3.65(m, 2 H) Exact Mass (calc.): 300.10 LC-MS (ESI+) m/e (M + 1)+: 301 |

TABLE 12

| | | |
|---|---|---|
| 88 | 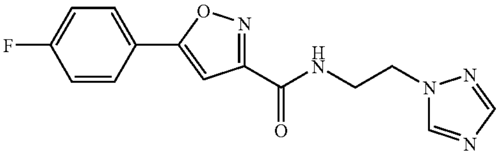 | $^1$H-NMR(DMSO-$d_6$, 200 MHz), ppm(δ): 8.43(m, 1 H), 8.20(br, 1 H), 8.06~7.99(m, 2 H), 7.91(m, 1 H), 7.41~7.33(2 H, m), 7.17(m, 1 H), 4.55(m, 2 H), 3.93(m, 2 H) Exact Mass (calc.): 301.10 LC-MS (ESI+) m/e (M + 1)+: 302 |
| 89 | 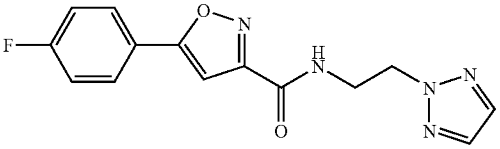 | $^1$H-NMR(DMSO-$d_6$, 200 MHz), ppm(δ): 8.95(br, 1 H), 8.05~7.95(m, 2 H), 7.78(s, 2 H), 7.50~7.34(m, 3 H), 4.61(t, 2 H), 3.78~3.62(m, 2 H) Exact Mass (calc.): 301.10 LC-MS (ESI+) m/e (M + 1)+: 302 |
| 90 | 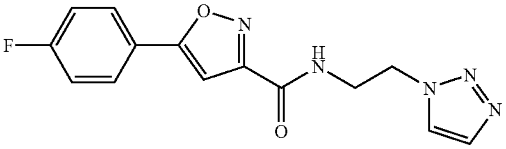 | $^1$H-NMR(DMSO-$d_6$, 200 MHz), ppm(δ): 8.95(m, 1 H), 8.11(s, 1 H), 8.00~7.96(m, 2 H), 7.71(s, 1 H), 7.45~7.34(m, 3 H), 4.59(t, 2 H), 3.78~3.62(m, 2 H) Exact Mass (calc.): 301.10 LC-MS (ESI+) m/e (M + 1)+: 302 |
| 91 | 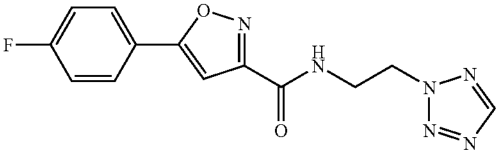 | $^1$H-NMR(DMSO-$d_6$, 200 MHz), ppm(δ): 8.96(m, 2 H), 8.02~7.94(m, 2 H), 7.45~7.33(m, 3 H), 4.90(t, 2 H), 3.85~3.73(m, 2 H) Exact Mass (calc.): 302.09 LC-MS (ESI+) m/e (M + 1)+: 303 |
| 92 | 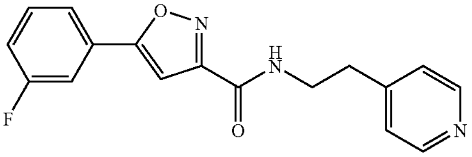 | Exact Mass (calc.): 311.11 LC-MS (ESI+) m/e $(M + 1)^+$: 312 |
| 93 | 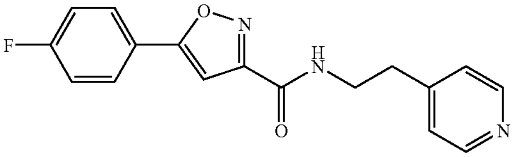 | Exact Mass (calc.): 311.11 LC-MS (ESI+) m/e $(M + 1)^+$: 312 |

TABLE 12-continued

| | | |
|---|---|---|
| 94 | 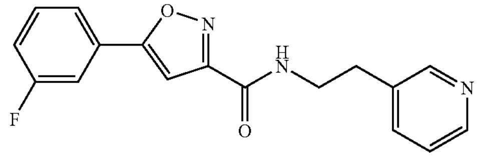 | Exact Mass (calc.): 311.11 LC-MS (ESI+) m/e $(M + 1)^+$: 312 |
| 95 | 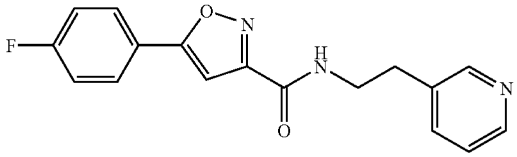 | Exact Mass (calc.): 311.11 LC-MS (ESI+) m/e $(M + 1)^+$: 312 |
| 96 | 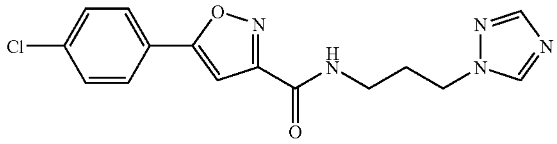 | $^1$H-NMR(DMSO-$d_6$, 200 MHz), ppm(δ): 8.90(m, 1 H), 8.49(s, 1 H), 7.95~7.91(m, 3 H), 7.62~7.58(m, 2 H), 7.39(s, 1 H), 4.20(t, 2 H), 3.29~3.25(m, 2 H), 2.05~1.98(m, 2 H) Exact Mass (calc.): 331.08 LC-MS (ESI+) m/e (M + 1)+: 332 |
| 97 | 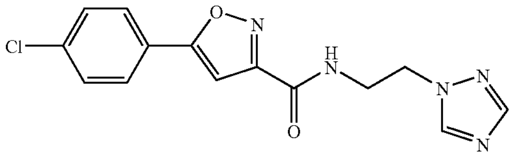 | $^1$H-NMR(DMSO-$d_6$, 200 MHz), ppm(δ): 8.95~8.84(m, 1 H), 8.46(s, 1 H), 7.95~7.91(m, 3 H), 7.62~7.58(m, 2 H), 7.36(s, 1 H), 4.36(m, 2 H), 3.66(m, 2 H) Exact Mass (calc.): 317.07 LC-MS (ESI+) m/e (M + 1)+: 318 |

TABLE 13

| | | |
|---|---|---|
| 98 | 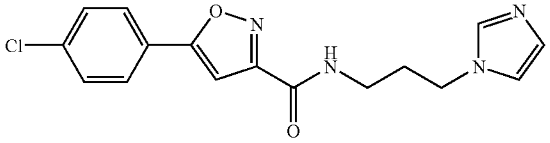 | $^1$H-NMR(DMSO-$d_6$, 500 MHz), ppm(δ): 9.00(t, 1 H), 7.97(m, 2 H), 7.66(m, 2 H), 7.44(s, 1 H), 7.22(s, 1 H), 6.90(s, 1 H) 4.03(t, 2 H), 3.31(q, 2 H), 2.00(q, 2 H) Exact Mass (calc.): 330.09 LC-MS (ESI+) m/e (M + 1)+: 331 |
| 99 | 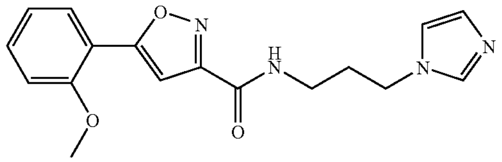 | $^1$H-NMR(acetone-$d_6$, 200 MHz), ppm(δ): 8.27~7.81(m, 2 H), 7.77~7.42(m, 2 H), 7.40~6.82(m, 5 H), 4.11(t, 2 H), 4.05(s, 3 H), 3.48(q, 2 H), 2.23~2.02(m, 2 H) Exact Mass (calc.): 326.14 LC-MS (ESI+) m/e $(M + 1)^+$: 327 |
| 100 | 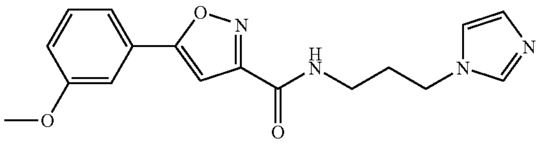 | $^1$H-NMR(acetone-$d_6$, 200 MHz), ppm(δ): 8.23(bs, 1 H), 7.79~6.89(m, 8 H), 4.24(t, 2 H), 3.91(s, 3 H), 3.47(q, 2 H), 2.39~2.12(m, 2 H) Exact Mass (calc.): 326.14 LC-MS (ESI+) m/e $(M + 1)^+$: 327 |
| 101 | 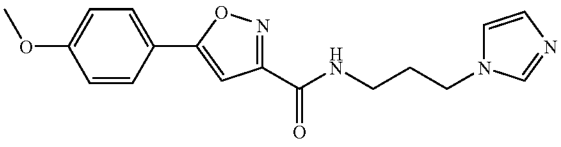 | $^1$H-NMR(acetone-$d_6$, 200 MHz), ppm(δ): 8.32~7.42(m, 4 H), 7.38~6.90(m, 5 H), 4.19(t, 2 H), 3.96(s, 3 H), 3.46(q, 2 H), 2.39~2.02(m, 2 H) Exact Mass (calc.): 326.14 LC-MS (ESI+) m/e $(M + 1)^+$: 327 |
| 102 | 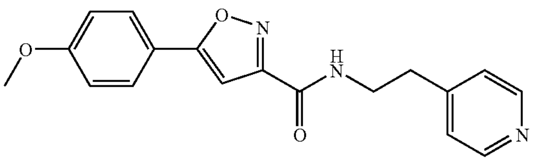 | $^1$H-NMR(acetone-$d_6$, 200 MHz), ppm(δ): 8.52~8.44(m, 2 H), 7.89~7.79(m, 2 H), 7.39~7.33(m, 2 H), 7.15~7.05(m, 3 H), 6.99(s, 1 H), 3.88(s, 3 H), 3.76~3.67(m, 2 H), 3.02(t, J = 7.40, 2 H) Exact Mass (calc.): 323.35 LC-MS (ESI+) m/e (M + 1)+: 324 |

TABLE 13-continued

| | | |
|---|---|---|
| 103 | 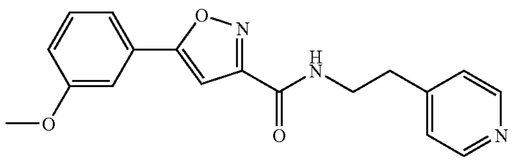 | $^1$H-NMR($CDCl_3$, 200 MHz), ppm(δ): 8.59~8.53(m, 2 H), 7.47~7.17(m, 6 H), 7.08~6.99(m, 1 H), 6.97(s, 1 H), 3.89(s, 3 H), 3.83~3.71(m, 2 H), 2.98(t, J = 6.80, 2 H)<br>Exact Mass (calc.): 323.35 LC-MS (ESI+) m/e (M + 1)+: 324 |
| 104 | 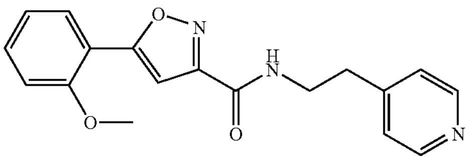 | $^1$H-NMR($CDCl_3$, 200 MHz), ppm(δ): 8.56(d, J = 5.80, 2 H), 7.95(d, J = 7.40 1 H), 7.46~7.40 (m, 1 H), 7.29~6.95(m, 6 H), 3.98(s, 3 H), 3.83~3.71(m, 2 H), 2.98(t, J = 6.80, 2 H)<br>Exact Mass (calc.): 323.35 LC-MS (ESI+) m/e (M + 1)+: 324 |
| 105 | 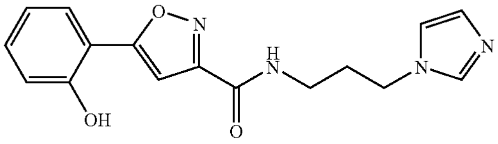 | Exact Mass (calc.): 312.12 LC-MS (ESI+) m/e $(M + 1)^+$: 313 |

TABLE 14

| | | |
|---|---|---|
| 106 | 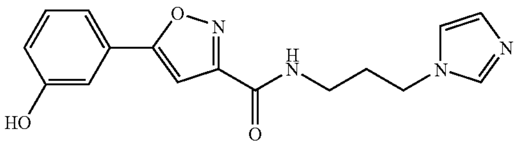 | Exact Mass (calc.): 312.12 LC-MS (ESI+) m/e $(M + 1)^+$: 313 |
| 107 | 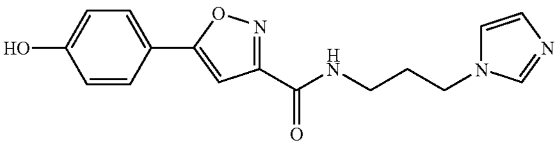 | Exact Mass (calc.): 312.12 LC-MS (ESI+) m/e $(M + 1)^+$: 313 |
| 108 | 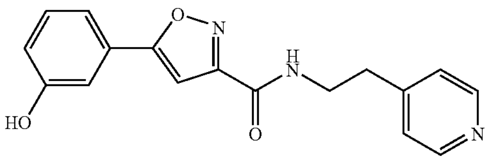 | Exact Mass (calc.): 309.11 LC-MS (ESI+) m/e $(M + 1)^+$: 310 |
| 109 | 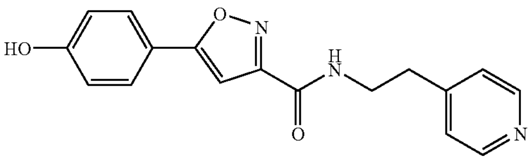 | Exact Mass (calc.): 309.11 LC-MS (ESI+) m/e $(M + 1)^+$: 310 |
| 110 | 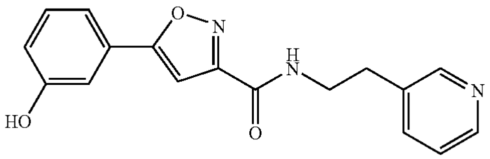 | Exact Mass (calc.): 309.11 LC-MS (ESI+) m/e $(M + 1)^+$: 310 |
| 111 | 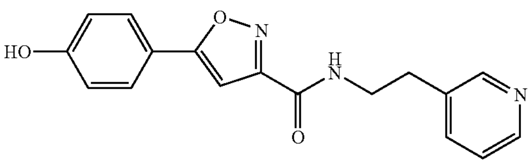 | Exact Mass (calc.): 309.11 LC-MS (ESI+) m/e $(M + 1)^+$: 310 |

TABLE 14-continued

| | | |
|---|---|---|
| 112 | 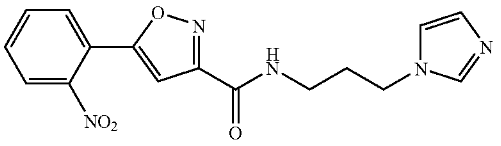 | Exact Mass (calc.): 341.11 LC-MS (ESI+) m/e $(M + 1)^+$: 342 |
| 113 | 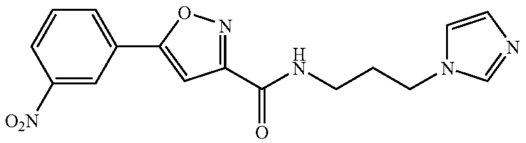 | $^1H$-NMR(acetone-$d_6$, 200 MHz), ppm(δ): 8.19~8.96(m, 2 H), 7.85~7.54(m, 5 H), 7.19(s, 1 H), 6.96~6.88(m, 1 H), 4.21(t, 2 H), 3.42(q, 2 H), 2.21~2.06(m, 2 H) Exact Mass (calc.): 341.11 LC-MS (ESI+) m/e $(M + 1)^+$: 342 |
| 114 | 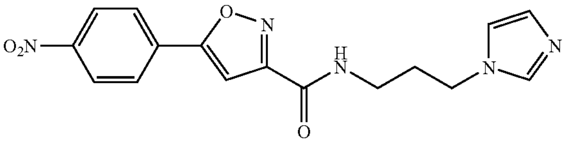 | $^1H$-NMR(acetone-$d_6$, 200 MHz), ppm(δ): 8.50~8.05(m, 5 H), 7.66~7.45(m, 2 H), 7.21~7.17(m, 1 H), 6.94(s, 1 H), 4.19(t, 2 H), 3.49(q, 2 H), 2.22~2.00(m, 2 H) Exact Mass (calc.): 341.11 LC-MS (ESI+) m/e $(M + 1)^+$: 342 |
| 115 | 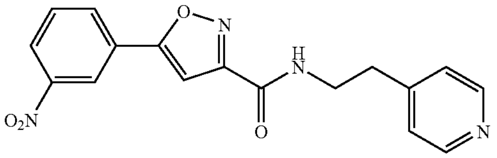 | Exact Mass (calc.): 338.10 LC-MS (ESI+) m/e $(M + 1)^+$: 339 |
| 116 | 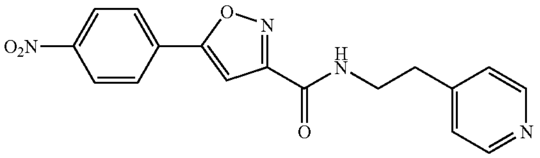 | Exact Mass (calc.): 338.10 LC-MS (ESI+) m/e $(M + 1)^+$: 339 |
| 117 | 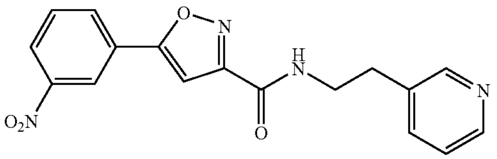 | Exact Mass (calc.): 338.10 LC-MS (ESI+) m/e $(M + 1)^+$: 339 |
| 118 | 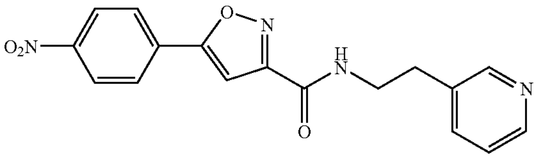 | Exact Mass (calc.): 338.10 LC-MS (ESI+) m/e $(M + 1)^+$: 339 |
| 119 | 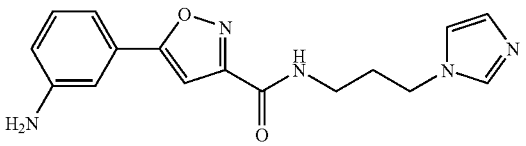 | $^1H$-NMR(acetone-$d_6$, 200 MHz), ppm(δ): 7.76~7.65(m, 1 H), 7.55~6.95(m, 6 H), 6.78~6.56(m, 2 H), 4.15(t, 2 H), 3.23(q, 2 H), 2.35~2.20(m, 2 H) Exact Mass (calc.): 311.14 LC-MS (ESI+) m/e $(M + 1)^+$: 312 |

TABLE 15

| | | |
|---|---|---|
| 120 | 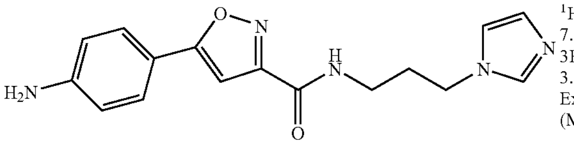 | $^1H$-NMR(acetone-$d_6$, 200 MHz), ppm(δ): 7.64~7.56(m, 1H), 7.35~7.26(m, 1H), 7.18~7.02(m, 3H), 6.92(s, 1H), 6.74~6.56(m, 3H), 4.09(t, 2H), 3.21(q, 2H), 2.22~1.99(m, 2H) Exact Mass (calc.): 311.14 LC-MS (ESI+) m/e $(M + 1)^+$: 312 |

TABLE 15-continued
| | | |
|---|---|---|
| 121 | 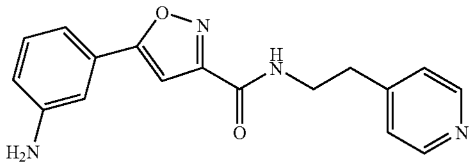 | Exact Mass (calc.): 308.13 LC-MS (ESI+) m/e $(M + 1)^+$: 309 |
| 122 | 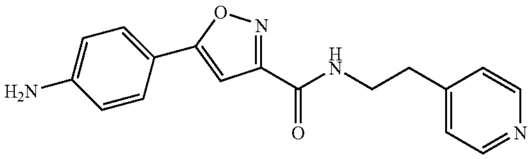 | Exact Mass (calc.): 308.13 LC-MS (ESI+) m/e $(M + 1)^+$: 309 |
| 123 | 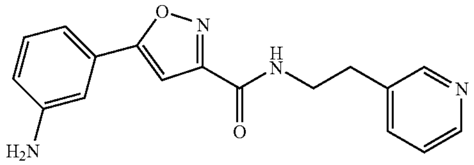 | Exact Mass (calc.): 308.13 LC-MS (ESI+) m/e $(M + 1)^+$: 309 |
| 124 | 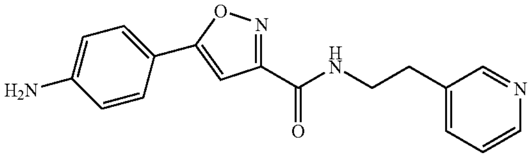 | Exact Mass (calc.): 308.13 LC-MS (ESI+) m/e $(M + 1)^+$: 309 |
| 125 | 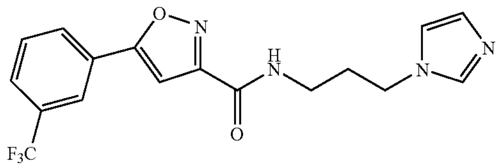 | Exact Mass (calc.): 364.11 LC-MS (ESI+) m/e $(M + 1)^+$: 365 |
| 126 | 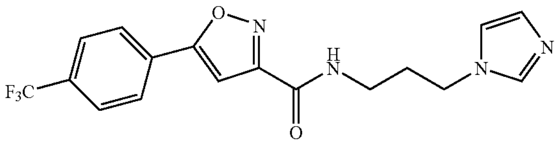 | Exact Mass (calc.): 364.11 LC-MS (ESI+) m/e $(M + 1)^+$: 365 |
| 127 | 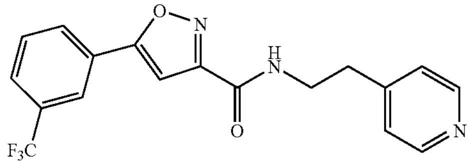 | Exact Mass (calc.): 361.10 LC-MS (ESI+) m/e $(M + 1)^+$: 362 |
| 128 | 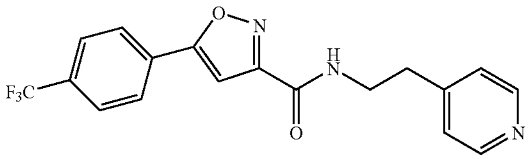 | Exact Mass (calc.): 361.10 LC-MS (ESI+) m/e $(M + 1)^+$: 362 |
| 129 | 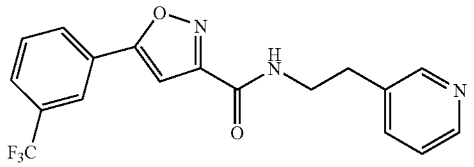 | Exact Mass (calc.): 361.10 LC-MS (ESI+) m/e $(M + 1)^+$: 362 |

TABLE 15-continued

| | | |
|---|---|---|
| 130 | 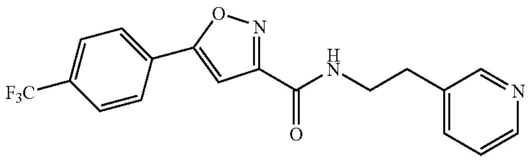 | Exact Mass (calc.): 361.10 LC-MS (ESI+) m/e $(M + 1)^+$: 362 |
| 131 | 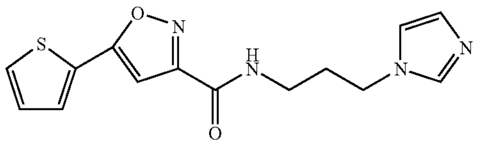 | $^1$H-NMR(acetone-$d_6$, 200 MHz), ppm(δ): 8.13(bs, 1H), 7.84~7.66(m, 2H), 7.66~7.61(m, 1H), 7.32~7.26(m, 1H), 7.21~7.18(m, 1H), 7.03(s, 1H), 6.77~6.72(m, 1H), 4.18(t, 2H), 3.48(q, 2H), 2.24~2.06(m, 2H) Exact Mass (calc.): 302.08 LC-MS (ESI+) m/e $(M + 1)^+$: 303 |
| 132 | 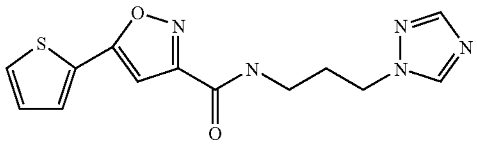 | $^1$H-NMR(DMSO-$d_6$, 200 Mhz), ppm(δ): 8.91(m, 1H), 8.52(s, 1H), 7.97(s, 1H), 7.83(m, 1H), 7.79(m, 1H), 7.29~7.25(m, 1H), 7.19(s, 1H), 4.23(t 2H), 3.29~3.23 (m, 2H), 2.07~2.00(m, 2H) Exact Mass (calc.): 303.08 LC-MS (ESI+) m/e (M + 1)+: 304 |

TABLE 16

| | | |
|---|---|---|
| 133 | 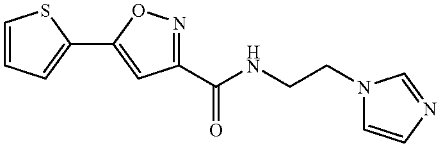 | $^1$H-NMR(acetone-$d_6$, 200 MHz), ppm(δ): 8.15(bs, 1 H), 7.86~7.76(m, 2 H), 7.57(s, 1 H), 7.32~7.25(m, 1 H), 7.16~7.12(m, 1 H), 7.01(s, 1 H), 6.93·6.89(m, 1 H), 4.33(t, J = 5.80, 2 H), 3.88~3.76(m, 2 H) Exact Mass (calc.): 288.33 LC-MS (ESI+) m/e (M + 1)+: 289 |
| 134 | 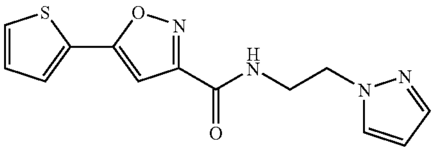 | $^1$H-NMR(acetone-$d_6$, 200 MHz), ppm(δ): 8.10(bs, 1 H), 7.86~7.76(m, 2 H), 7.72~7.66(m, 1 H), 7.49~7.46(m, 1 H), 7.33~7.26(m, 1 H), 7.02(s, 1 H), 6.27~6.23(m, 1 H), 4.44(t, J = 5.80, 2 H), 3.92~3.81(m, 2 H) Exact Mass (calc.): 288.33 LC-MS (ESI+) m/e (M + 1)+: 289 |
| 135 | 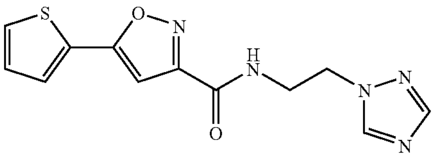 | $^1$H-NMR(acetone-$d_6$, 200 MHz), ppm(δ): 8.40(bs, 1 H), 8.18(bs, 1 H), 7.90(s, 1 H), 7.84~7.76(m, 2 H), 7.32~7.26(m, 1 H), 7.01(s, 1 H), 4.54(t, J = 5.40, 2 H), 3.96~3.83(m, 2 H) Exact Mass (calc.): 289.32 LC-MS (ESI+) m/e (M + 1)+: 290 |
| 136 | 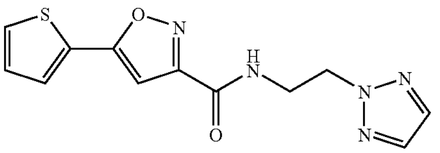 | $^1$H-NMR(acetone-$d_6$, 200 MHz), ppm(δ): 8.10(bs, 1 H), 7.85~7.76(m, 2 H), 7.71(s, 2 H), 7.32~7.26(m, 1 H), 7.02(s, 1 H), 4.74(t, J = 5.80, 2 H), 4.04~3.90(m, 2 H) Exact Mass (calc.): 289.32 LC-MS (ESI+) m/e (M + 1)+: 290 |
| 137 | 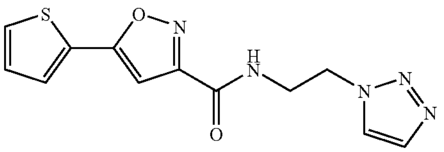 | $^1$H-NMR(acetone-$d_6$, 200 MHz), ppm(δ): 8.19(bs, 1 H), 8.03(s, 1 H), 7.84~7.76(m, 2 H), 7.67(s, 1 H), 7.32~7.26(m, 1 H), 7.01(s, 1 H), 4.74(t, J = 5.40, 2 H), 4.01~3.88(m, 2 H) Exact Mass (calc.): 289.32 LC-MS (ESI+) m/e (M + 1)+: 290 |
| 138 | 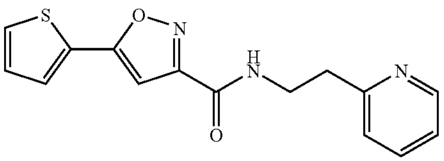 | Exact Mass (calc.): 299.07 LC-MS (ESI+) m/e $(M + 1)^+$: 300 |

TABLE 16-continued

| | | |
|---|---|---|
| 139 | 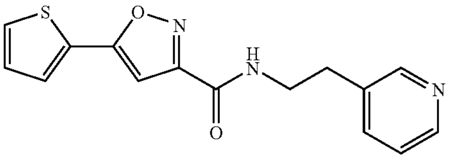 | $^1$H-NMR(acetone-$d_6$, 200 MHz), ppm(δ): 8.53~8.42(m, 2 H), 8.07(bs, 1 H), 7.83~7.68(m, 3 H), 7.35~7.25(m, 2 H), 7.00(s, 1 H), 3.73(q, 2 H), 3.01(t, 2 H) Exact Mass (calc.): 299.07 LC-MS (ESI+) m/e $(M + 1)^+$: 300 |

TABLE 17

| | | |
|---|---|---|
| 140 | 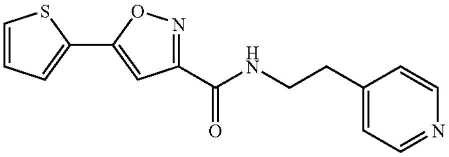 | $^1$H-NMR(acetone-$d_6$, 200 MHz), ppm(δ): 8.53~8.43(m, 2 H), 8.08(bs, 1 H), 7.84~7.53(m, 2 H), 7.38~7.11(m, 3 H), 7.01(s, 1 H), 3.74(q, 2 H), 3.02(t, 2 H) Exact Mass (calc.): 299.07 LC-MS (ESI+) m/e $(M + 1)^+$: 300 |
| 141 | 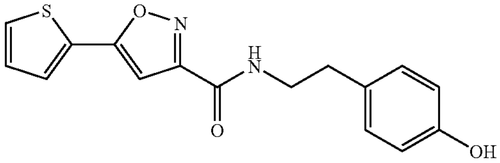 | $^1$H-NMR(acetone-$d_6$, 200 MHz), ppm(δ): 8.21(bs, 1 H), 7.91(bs, 1 H), 7.82~7.76(m, 2 H), 7.31~7.26(m, 1 H), 7.15~7.11(m, 2 H), 7.01(s, 1 H), 6.84~6.78(m, 2 H), 3.62(q, 2 H), 2.87(t, 2 H) Exact Mass (calc.): 314.07 LC-MS (ESI+) m/e $(M + 1)^+$: 315 |
| 142 | 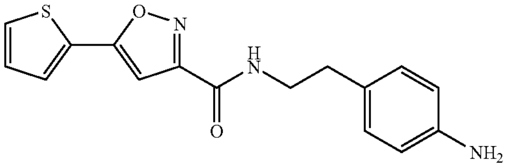 | Exact Mass (calc.): 313.09 LC-MS (ESI+) m/e $(M + 1)^+$: 314 |
| 143 | 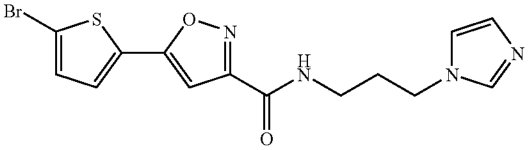 | $^1$H-NMR(acetone-$d_6$, 200 MHz), ppm(δ): 8.15(bs, 1 H), 7.90~7.72(m, 1 H), 7.65~7.58(m, 1 H), 7.39~7.21(m, 21 H), 7.16~7.01(m, 2 H), 4.23(t, 2 H), 3.46(q, 2 H), 2.27~2.12(m, 2 H) Exact Mass (calc.): 379.99 LC-MS (ESI+) m/e $(M + 1)^+$: 381 |
| 144 | 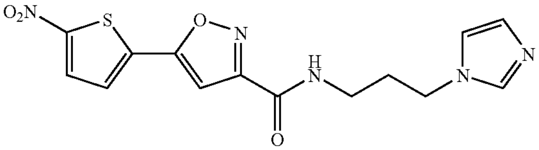 | Exact Mass (calc.): 347.07 LC-MS (ESI+) m/e $(M + 1)^+$: 348 |
| 145 | 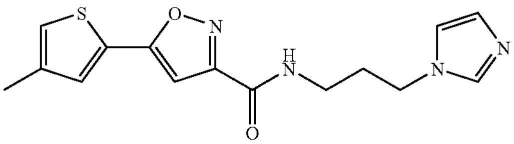 | Exact Mass (calc.): 316.10 LC-MS (ESI+) m/e $(M + 1)^+$: 317 |
| 146 | 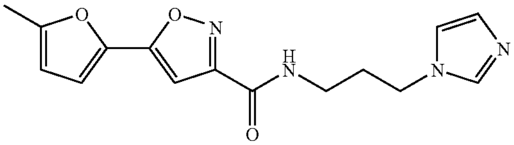 | Exact Mass (calc.): 300.12 LC-MS (ESI+) m/e $(M + 1)^+$: 301 |
| 147 | 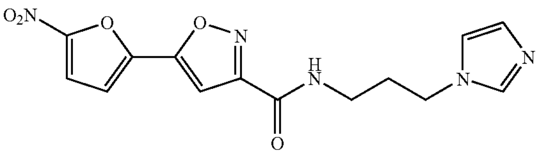 | Exact Mass (calc.): 331.09 LC-MS (ESI+) m/e $(M + 1)^+$: 332 |

TABLE 17-continued

| | | |
|---|---|---|
| 148 | 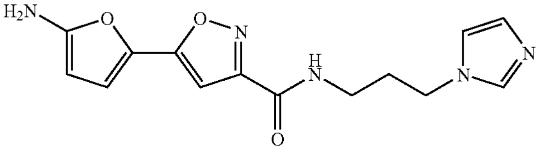 | Exact Mass (calc.): 301.12 LC-MS (ESI+) m/e $(M + 1)^+$: 302 |
| 149 | 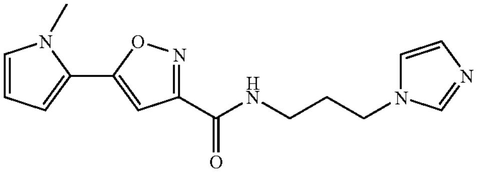 | $^1$H-NMR(DMSO-$d_6$, 500 MHz), ppm(δ): 8.86(t, 1 H), 7.66(s, 1 H), 7.22(s, 1 H), 7.08(m, 1 H), 6.90(m, 2 H), 6.75(m, 1 H), 6.18(m, 1 H), 4.03(t, 2 H), 3.85(s, 3 H), 3.23(q, 2 H), 1.96(m, 2 H) Exact Mass (calc.): 299.14 LC-MS (ESI+) m/e (M + 1)+: 300 |

TABLE 18

| | | |
|---|---|---|
| 150 | 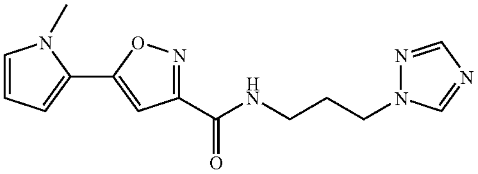 | $^1$H-NMR(Acetone-$d_6$, 500 MHz), ppm(δ): 8.41(s, 1 H), 8.00(br, 1 H), 7.88(s, 1 H), 6.99(m, 1 H), 6.75(m, 2 H), 6.18(m, 1 H), 4.36(t, 2 H), 3.92(s, 3 H), 3.47(q, 2 H), 2.22(m, 2 H) Exact Mass (calc.): 300.13 LC-MS (ESI+) m/e (M + 1)+: 301 |
| 151 | 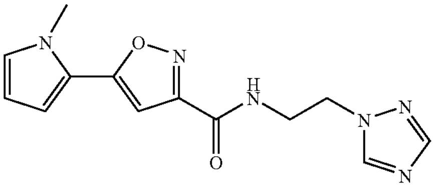 | $^1$H-NMR(DMSO-$d_6$, 500 MHz), ppm(δ): 8.87(m, 1 H), 8.48(s, 1 H), 7.97(s, 1 H), 7.07(m, 1 H), 6.90(s, 1 H), 6.73(m, 1 H), 6.16(m, 1 H), 4.37(t, 2 H), 3.83(s, 3 H), 3.66(m, 2 H) Exact Mass (calc.): 286.12 LC-MS (ESI+) m/e (M + 1)+: 287 |
| 152 | 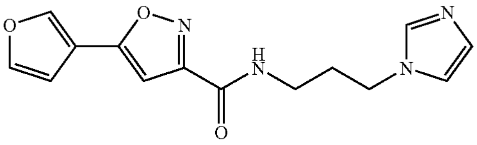 | $^1$H-NMR(DMSO-$d_6$, 500 MHz), ppm(δ): 8.89(m, 1 H), 8.45(s, 1 H), 7.90(m, 1 H), 7.66(m, 1 H), 7.21(s, 1 H), 7.10(s, 1 H), 7.03(m, 1 H), 6.90(s, 1 H), 4.02(t, 2 H), 3.24(q, 2 H), 1.97(quintet, 2 H) Exact Mass (calc.): 286.11 LC-MS (ESI+) m/e (M + 1)+: 287 |
| 153 | 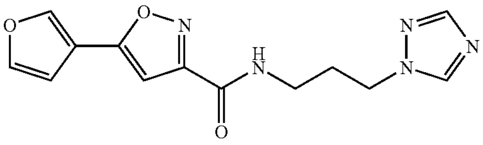 | $^1$H-NMR(DMSO-$d_6$, 500 MHz), ppm(δ): 8.91(m, 1 H), 8.54(s, 1 H), 8.46(s, 1 H), 7.98(s, 1 H), 7.90(m, 1 H), 7.10(s, 1 H), 7.03(m, 1 H), 4.24(t, 2 H), 3.26(q, 2 H), 2.05(m, 2 H) Exact Mass (calc.): 287.10 LC-MS (ESI+) m/e (M + 1)+: 288 |
| 154 | 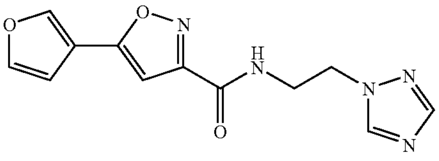 | $^1$H-NMR(DMSO-$d_6$, 500 MHz), ppm(δ): 8.91(m, 1 H), 8.49(s, 1 H), 8.45(s, 1 H), 7.97(s, 1 H), 7.90(m, 1 H), 7.07(s, 1 H), 7.03(m, 1 H), 4.34(t, 2 H), 3.67(q, 2 H) Exact Mass (calc.): 273.09 LC-MS (ESI+) m/e (M + 1)+: 274 |
| 155 | 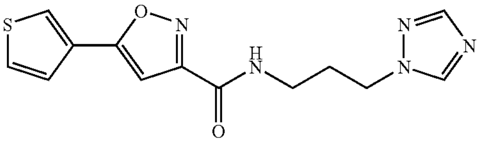 | $^1$H-NMR(DMSO-$d_6$, 500 MHz), ppm(δ): 8.90(m, 1 H), 8.54(s, 1 H), 8.27(m, 1 H), 7.98(s, 1 H), 7.79(m, 1 H), 7.64(m, 1 H), 7.20(s, 1 H), 4.23(t, 2 H), 3.24(q, 2 H), 2.06(m, 2 H) Exact Mass (calc.): 303.08 LC-MS (ESI+) m/e (M + 1)+: 304 |
| 156 | 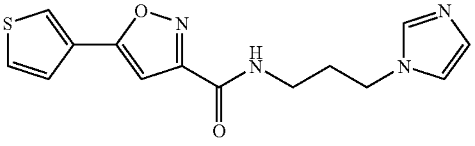 | $^1$H-NMR($CDCl_3$, 200 MHz), ppm(δ): 7.80(dd, 1 H), 7.54(s, 1 H), 7.38~7.45(m, 3 H), 7.07(s, 1 H), 6.97(s, 1 H), 6.81(s, 1 H), 4.05(t, 2 H), 3.47(q, 2 H), 2.13(td, 2 H) Exact Mass (calc.): 302.08 LC-MS (ESI+) m/e (M + 1)+: 303 |

TABLE 19

| | | |
|---|---|---|
| 157 | 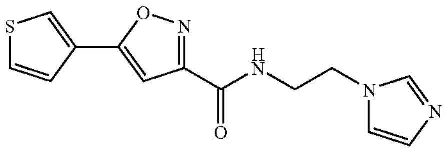 | $^1$H-NMR($CDCl_3$, 200 MHz), ppm(δ): 7.83(s, 1 H), 7.51(s, 1 H), 7.43(bs, 2 H), 7.31(bs, 1 H), 7.09(s, 1 H), 6.97(s, 1 H), 6.81(s, 1 H), 4.23(t, 2 H), 3.79(q, 2 H) Exact Mass (calc.): 288.07 LC-MS (ESI+) m/e (M + 1)+: 289 |
| 158 | 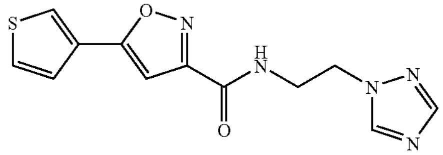 | $^1$H-NMR(DMSO-$d_6$, 500 MHz), ppm(δ): 8.92(m, 1 H), 8.50(s, 1 H), 8.26(m, 1 H), 7.98(s, 1 H), 7.78(m, 1 H), 7.64(m, 1 H), 7.18(s, 1 H), 4.39(t, 2 H), 3.67(q, 2 H) Exact Mass (calc.): 289.06 LC-MS (ESI+) m/e (M + 1)+: 290 |
| 159 | 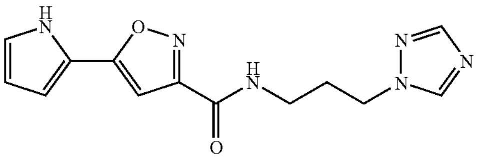 | $^1$H-NMR(DMSO-$d_6$, 500 MHz), ppm(δ): 8.85(m, 1 H), 8.54(s, 1 H), 7.98(s, 1 H), 7.08(m, 1 H), 6.84(s, 1 H), 6.75(m, 1 H), 6.23(m, 1 H), 4.22(t, 2 H), 3.26(q, 2 H), 2.05(m, 2 H) Exact Mass (calc.): 286.12 LC-MS (ESI+) m/e (M + 1)+: 287 |
| 160 | 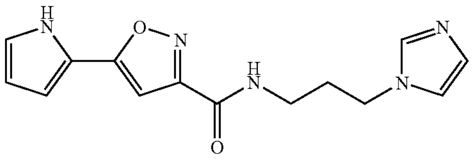 | $^1$H-NMR(DMSO-$d_6$, 500 MHz), ppm(δ): 8.85(m, 1 H), 7.66(s, 1 H), 7.22(s, 1 H), 7.08(m, 1 H), 6.90(s, 1 H), 6.75(s, 1 H), 6.74(m, 1 H), 6.23(m, 1 H), 4.00(t, 2 H), 3.22(q, 2 H), 1.95(m, 2 H) Exact Mass (calc.): 285.12 LC-MS (ESI+) m/e (M + 1)+: 286 |
| 161 | 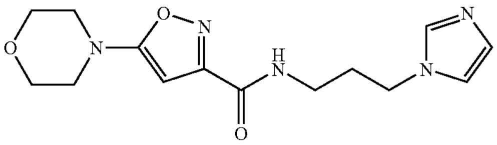 | $^1$H-NMR(Acetone-$d_6$, 200 MHz), ppm(δ): 7.75(br, 1 H), 7.62(s, 1 H), 7.17(m, 1 H), 6.93(1 H), 5.55(s, 1 H), 4.14(t, 2 H), 3.78(m, 4 H), 3.43~3.36(m, 6 H), 2.11(m, 2 H) Exact Mass (calc.): 305.15 LC-MS (ESI+) m/e (M + 1)+: 306 |
| 162 | 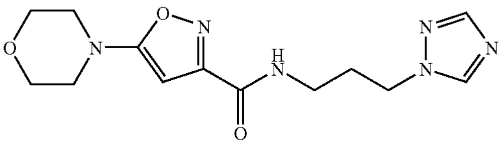 | $^1$H-NMR(DMSO-$d_6$, 200 MHz), ppm(δ): 8.60(m, 1 H), 8.52(s, 1 H), 7.97(s, 1 H), 5.65(s, 1 H), 4.19(t, 2 H), 3.69(m, 4 H), 3.19(m, 2 H), 2.00(m, 2 H) Exact Mass (calc.): 306.14 LC-MS (ESI+) m/e (M + 1)+: 307 |
| 163 | 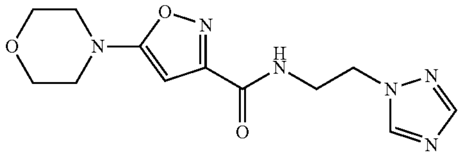 | $^1$H-NMR(DMSO-$d_6$, 200 MHz), ppm(δ): 8.61(m, 1 H), 8.45(s, 1 H), 7.96(s, 1 H), 5.62(s, 1 H), 4.35(m, 2 H), 3.69(m, 4 H), 3.61(m, 2 H) Exact Mass (calc.): 292.13 LC-MS (ESI+) m/e (M + 1)+: 293 |

TABLE 20

| | | |
|---|---|---|
| 164 | 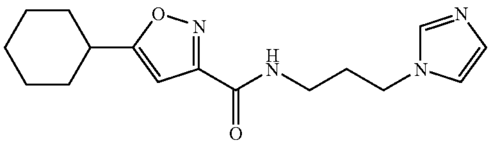 | $^1$H-NMR(DMSO-$d_6$, 200 MHz), ppm(δ): 8.90(m, 1 H), 7.68(s, 1 H), 7.22(s, 1 H), 6.91(s, 1 H), 6.54(s, 1 H), 4.00(t, 2 H), 3.20(m, 2 H), 2.95(m, 1 H), 2.00~1.20(m, 10 H) Exact Mass (calc.): 302.17 LC-MS (ESI+) m/e (M + 1)+: 303 |
| 165 | 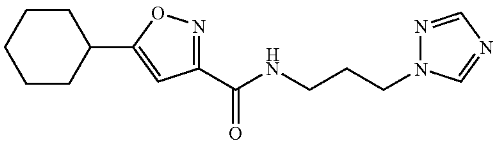 | $^1$H-NMR(DMSO-$d_6$, 200 MHz), ppm(δ): 8.80(m, 1 H), 8.53(s, 1 H), 7.98(s, 1 H), 6.54(s, 1 H), 4.22(t, 2 H), 3.20(m, 2 H), 2.86(m, 1 H), 2.05~1.21(m, 10 H) Exact Mass (calc.): 303.17 LC-MS (ESI+) m/e (M + 1)+: 304 |

TABLE 20-continued

| | | |
|---|---|---|
| 166 | 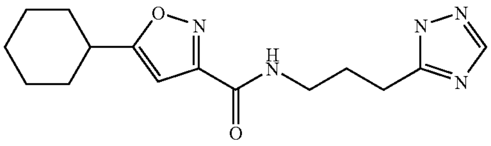 | $^{1}$H-NMR(DMSO-$d_6$, 200 MHz), ppm(δ): 8.90(m, 1 H), 8.48(s, 1 H), 7.97(s, 1 H), 6.51(s, 1 H), 4.40(t, 2 H), 3.89(m, 2 H), 2.86(m, 1 H), 2.05~1.21(m, 10 H) Exact Mass (calc.): 289.15 LC-MS (ESI+) m/e (M + 1)+: 290 |
| 167 | 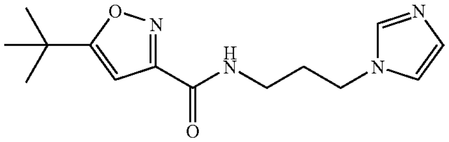 | $^{1}$H-NMR(DMSO-$d_6$, 200 MHz), ppm(δ): 8.80(m, 1 H), 7.64(s, 1 H), 7.20(s, 1 H), 6.88(s, 1 H), 6.54(s, 1 H), 4.00(t, 2 H), 3.18(m, 2 H), 1.93(m, 2 H), 1.30(s, 9 H) Exact Mass (calc.): 276.16 LC-MS (ESI+) m/e (M + 1)+: 277 |
| 168 | 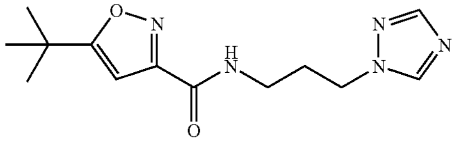 | $^{1}$H-NMR(Acetone-$d_6$, 500 MHz), ppm(δ): 8.39(s, 1 H), 7.90(br, 1 H), 7.87(s, 1 H), 6.43(s, 1 H), 4.34(t, 2 H), 3.43(m, 2 H), 2.19(m, 2 H), 1.37(s, 9 H) Exact Mass (calc.): 277.15 LC-MS (ESI+) m/e (M + 1)+: 278 |
| 169 | 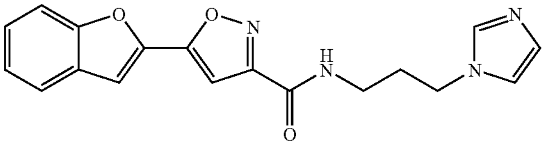 | $^{1}$H-NMR(DMSO-$d_6$, 500 MHz), ppm(δ): 9.01(m, 1 H), 7.80(d, 1 H), 7.78(m, 2 H), 7.74(s, 1 H), 7.49(m, 1 H), 7.35(m, 3 H), 7.21(s, 1 H), 6.89(s, 1 H), 4.02(t, sH), 3.25(q, 2 H), 1.97(q, 2 H) Exact Mass (calc.): 336.12 LC-MS (ESI+) m/e (M + 1)+: 337 |
| 170 | 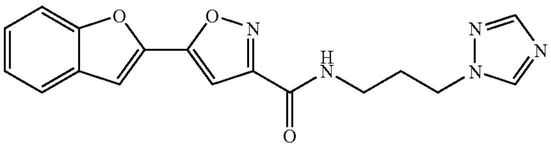 | $^{1}$H-NMR(DMSO-$d_6$, 500 MHz), ppm(δ): 9.03(t, 1 H), 8.55(s, 1 H), 7.99(s, 1 H), 7.81(d, 1 H), 7.80(m, 2 H), 7.50(t, 1 H), 7.36(m, 2 H), 4.24(t, 2 H), 3.27(q, 2 H), 2.06(q, 2 H) Exact Mass (calc.): 337.12 LC-MS (ESI+) m/e (M + 1)+: 338 |

TABLE 21

| | | |
|---|---|---|
| 171 | 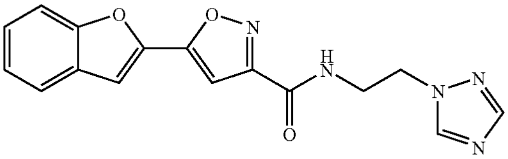 | $^{1}$H-NMR(DMSO-$d_6$, 500 MHz), ppm(δ): 9.04(t, 1 H), 8.50(s, 1 H), 7.98(s, 1 H), 7.80(d, 1 H), 7.78(m, 2 H), 7.48(t, 1 H), 7.37(m, 1 H), 7.31(s, 1 H), 4.39(t, 2 H), 3.68(q, 2 H) Exact Mass (calc.): 323.10 LC-MS (ESI+) m/e (M + 1)+: 324 |
| 172 | 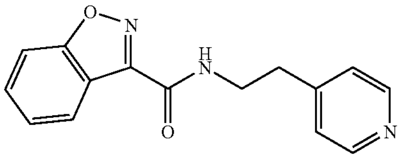 | $^{1}$H-NMR(acetone-$d_6$, 200 MHz), ppm((): 8.15~7.84(m, 3 H), 7.66~7.49(m, 3 H), 7.35~7.15(m, 3 H), 3.75(q, 2 H), 3.05(t, 2 H) Exact Mass (calc.): 267.10 LC-MS (ESI+) m/e (M + 1)+: 268 |
| 173 | ‖ EMBED ChemDraw.Document.6. 0 ¶ 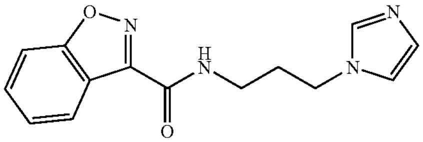 | $^{1}$H-NMR(acetone-$d_6$, 200 MHz), ppm(δ): 8.17(bs, 1 H), 8.01~7.92(m, 2 H), 7.69~7.17(m, 4 H), 7.01~6.73(m, 1 H), 4.21(t, 2 H), 3.45(q, 2 H), 2.20~2.05(m, 2 H) Exact Mass (calc.): 270.11 LC-MS (ESI+) m/e $(M + 1)^+$: 271 |
| 174 | 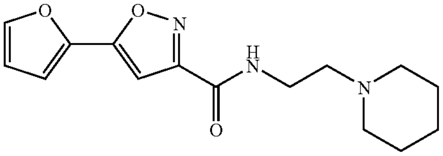 | $^{1}$H-NMR(acetone-$d_6$, 200 MHz), ppm(δ): 7.90~7.75(m, 2 H), 7.24~7.15(m, 1 H), 6.92(s, 1 H), 6.76~6.72(m, 1 H), 3.75~3.52(m, 6 H), 2.68~2.42(m, 6 H) Exact Mass (calc.): 289.14 LC-MS (ESI+) m/e $(M + 1)^+$: 290 |

TABLE 21-continued

| | | |
|---|---|---|
| 175 | 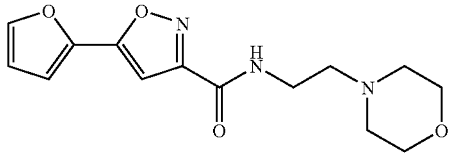 | $^1$H-NMR(acetone-$d_6$, 200 MHz), ppm(δ): 7.90~7.75(m, 2 H), 7.24~7.15(m, 1 H), 6.92(s, 1 H), 6.76~6.72(m, 1 H), 3.61~3.45(m, 2 H), 2.62~2.42(m, 6 H), 1.65~1.39(m, 6 H) Exact Mass (calc.): 291.12 LC-MS (ESI+) m/e $(M + 1)^+$: 292 |
| 176 | 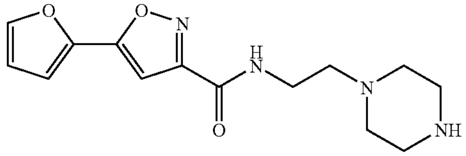 | $^1$H-NMR($CDCl_3$, 200 MHz), ppm(δ): 7.59(s, 1 H), 7.31(bs, 1 H), 6.96(d, 1 H), 6.80(d, 1 H), 6.57(q, 1 H), 3.84~3.95(m, 2 H), 3.60(q, 1 H), 3.39(t, 1 H), 2.85(s, 1 H), 2.57~2.70(m, 3 H), 2.38(6, 1 H) Exact Mass (calc.): 290.14 LC-MS (ESI+) m/e (M + 1)+: 291 |
| 177 | 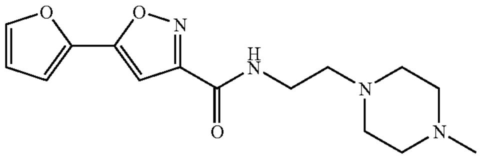 | $^1$H-NMR($CDCl_3$, 200 MHz), ppm(δ): 7.58(s, 1 H), 7.35(bs, 1 H), 6.95(d, 1 H), 6.86(s, 1 H), 6.59(q, 1 H), 3.76(q, 1 H), 3.51~3.65(m, 3 H), 2.48~2.55(m, 8 H), 2.32(s, 3 H) Exact Mass (calc.): 304.15 LC-MS (ESI+) m/e (M + 1)+: 305 |

TABLE 22

| | | |
|---|---|---|
| 178 | 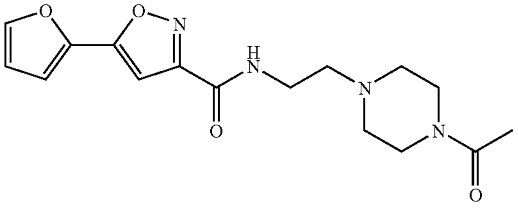 | $^1$H-NMR($CDCl_3$, 200 MHz), ppm(δ): 7.58(s, 1 H), 7.32(bs, 1 H), 6.95(q, 1 H), 6.86(s, 1 H), 6.56(t, 1 H), 3.85(t, 1 H), 3.48~3.68(m, 5 H), 2.62(t, 2 H), 2.50(q, 4 H), 2.10(s, 3 H) Exact Mass (calc.): 332.15 LC-MS (ESI+) m/e (M + 1)+: 333 |
| 179 | 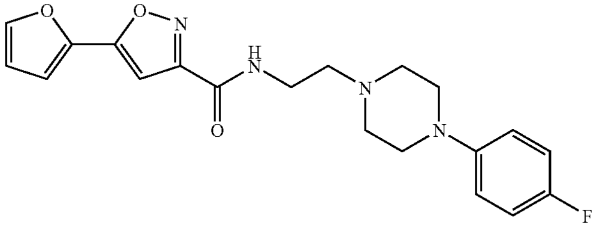 | $^1$H-NMR($CDCl_3$, 200 MHz), ppm(δ): 7.59(s, 1 H), 7.36(bs, 1 H), 6.88~6.98(m, 5 H), 6.57(q, 1 H), 3.62(q, 2 H), 3.16(t, 4 H), 2.68~2.71(m, 6 H) Exact Mass (calc.): 384.16 LC-MS (ESI+) m/e (M + 1)+: 385 |
| 180 | 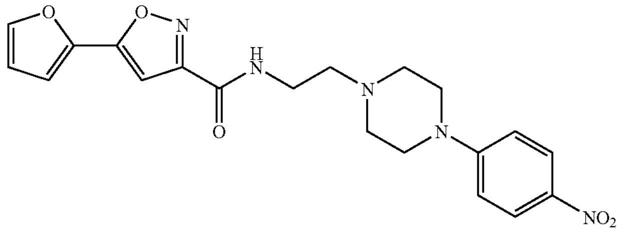 | $^1$H-NMR($CDCl_3$, 200 MHz), ppm(δ): 8.17(s, 1 H), 8.12(s, 1 H), 7.59(d, 1 H), 7.34(bs, 1 H), 6.96(d, 1 H), 6.88(d, 2 H), 6.82(s, 1 H), 6.08(q, 1 H), 3.63(q, 2 H), 3.47(t, 4 H), 2.68(t, 6 H) Exact Mass (calc.): 411.15 LC-MS (ESI+) m/e (M + 1)+: 412 |
| 181 | 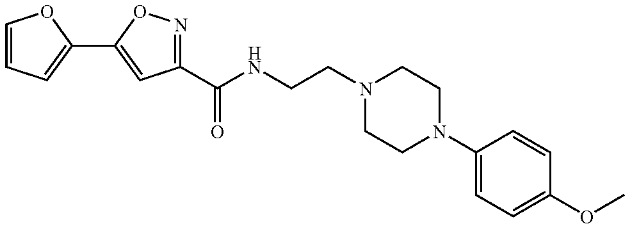 | $^1$H-NMR($CDCl_3$, 200 MHz), ppm(δ): 7.59(s, 1 H), 7.38(bs, 1 H), 6.96(d, 1 H), 6.89(d, 3 H), 6.83(s, 1 H), 6.57(q, 1 H), 3.79(s, 3 H), 3.61(q, 2 H), 3.14(t, 4 H), 2.65~2.71(m, 6 H) Exact Mass (calc.): 396.18 LC-MS (ESI+) m/e (M + 1)+: 397 |

TABLE 22-continued

| | | |
|---|---|---|
| 182 | 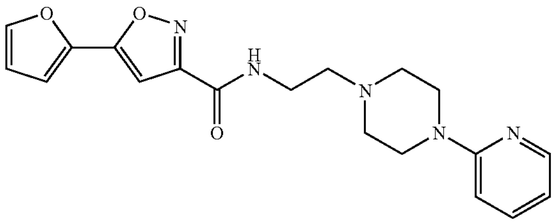 | $^{1}$H-NMR($CDCl_3$, 200 MHz), ppm(δ): 8.20(d, 1 H), 7.58(s, 1 H), 7.49(t, 1 H), 7.44(bs, 1 H), 6.95(d, 1 H), 6.87(s, 1 H), 6.61~6.68(m, 2 H), 6.56(q, 1 H), 3.56~3.66(m, 6 H), 2.61~2.69(m, 6 H) Exact Mass (calc.): 367.16 LC-MS (ESI+) m/e (M + 1)+: 368 |
| 183 | 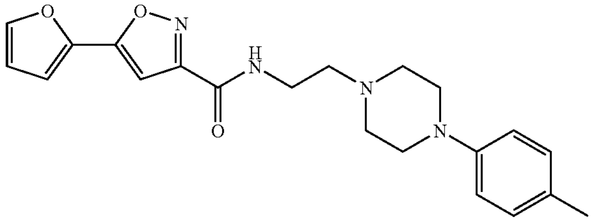 | 1H-NMR($CDCl_3$, 200 MHz), ppm(δ): 7.58(d, 1 H), 7.39(bs, 1 H), 7.03(d, 2 H), 6.97(d, 1 H), 6.88(s, 1 H), 6.85(d, 2 H), 6.56(q, 1 H), 3.61(q, 2 H), 3.17~3.21(m, 4 H), 2.64~2.71(m, 6 H) Exact Mass (calc.): 380.18 LC-MS (ESI+) m/e (M + 1)+: 318 |

TABLE 23

| | | |
|---|---|---|
| 184 | 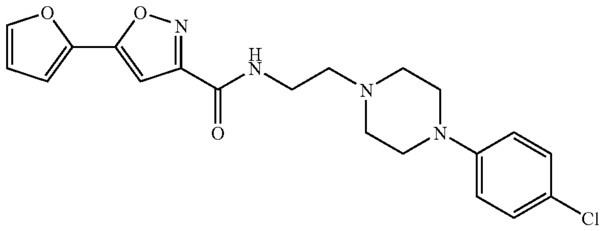 | $^{1}$H-NMR($CDCl_3$, 200 MHz), ppm(δ): 7.58(s, 1 H), 7.37(bs, 1 H), 7.20~7.24(m, 2 H), 6.96(d, 1 H), 6.88(s, 1 H), 6.83(s, 1 H), 6.56(q, 1 H), 3.61(q, 2 H), 3.18~3.23(m, 4 H), 2.66~2.71(m, 6 H) Exact Mass (calc.): 400.13 LC-MS (ESI+) m/e (M + 1)+: 401 |
| 185 | 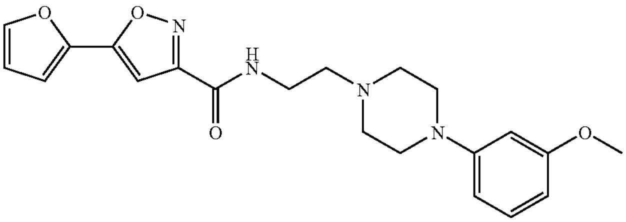 | 1H-NMR($CDCl_3$, 200 MHz), ppm(δ): 7.58(s, 1 H), 7.39(bs, 1 H), 7.18(t, 1 H), 6.95(d, 1 H), 6.87(s, 1 H), 6.53~6.57(m, 2 H), 6.47(d, 1 H), 6.41(s, 1 H), 3.80(d, 3 H), 3.61(q, 2 H), 3.21~3.26(m, 4 H), 2.64~2.69(m, 6 H) Exact Mass (calc.): 396.18 LC-MS (ESI+) m/e (M + 1)+: 397 |
| 186 | 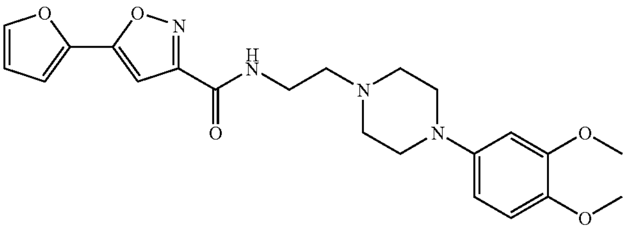 | $^{1}$H-NMR($CDCl_3$, 200 MHz), ppm(δ): 7.58(s, 1 H), 7.(bs, 1 H), 6.96(d, 1 H), 6.91(s, 1 H), 6.87(s, 1 H), 6.57(q, 1 H), 6.41~6.48(m, 2 H), 3.85(s, 3 H), 3.79(s, 3 H), 3.60(q, 2 H), 3.05(bs, 4 H), 2.65~2.71(m, 6 H) Exact Mass (calc.): 426.19 LC-MS (ESI+) m/e (M + 1)+: 427 |
| 187 | 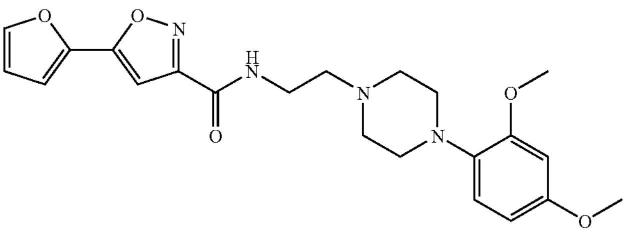 | $^{1}$H-NMR($CDCl_3$, 200 MHz), ppm(δ): 7.59(s, 1 H), 7.40(bs, 1 H), 6.96(d, 1 H), 6.91(s, 1 H), 6.87(s, 1 H), 6.57(q, 1 H), 6.41~6.48(m, 2 H), 3.85(s, 3 H), 3.79(s, 3 H), 3.60(q, 2 H), 3.05(bs, 4 H), 2.65~2.71(m, 6 H) Exact Mass (calc.): 426.19 LC-MS (ESI+) m/e (M + 1)+: 427 |

TABLE 23-continued

| | | |
|---|---|---|
| 188 | 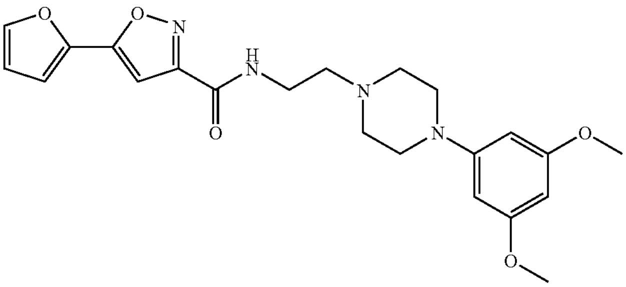 | $^1$H-NMR($CDCl_3$, 200 MHz), ppm(δ): 7.58(d, 1 H), 7.35(bs, 1 H), 6.95(q, 1 H), 6.87(d, 1 H), 6.57(q, 1 H), 6.11(q, 2 H), 6.04(q, 1 H), 3.79(s, 6 H), 3.61(q, 2 H), 3.23(t, 4 H), 2.64~2.69(m, 6 H)<br>Exact Mass (calc.): 426.19 LC-MS (ESI+) m/e (M + 1)+: 427 |
| 189 | 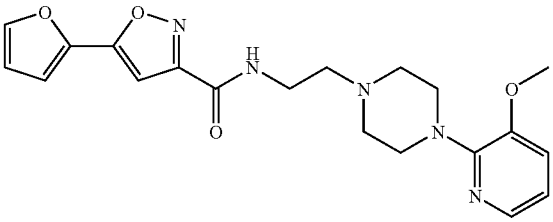 | $^1$H-NMR($CDCl_3$, 200 MHz), ppm(δ): 7.86(dd, 1 H), 7.55(d, 1 H), 7.46(bs, 1 H), 7.00(q, 1 H), 6.93(d, 1 H), 6.79~6.87(m, 2 H), 6.53(d, 1 H), 6.79~6.87(m, 2 H), 6.53(q, 1 H), 3.83(s, 3 H), 3.59(q, 2 H), 3.41~3.43(m, 4 H), 2.63~2.72(m, 6 H)<br>Exact Mass (calc.): 397.18 LC-MS (ESI+) m/e (M + 1)+: 398 |

TABLE 24

| | | |
|---|---|---|
| 190 | 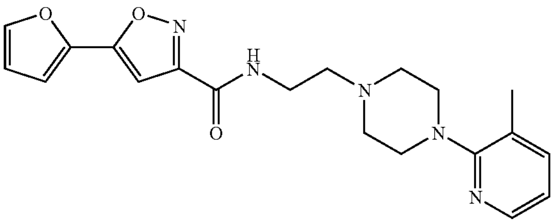 | $^1$H-NMR($CDCl_3$, 200 MHz), ppm(δ): 8.16(dd, 1 H), 7.75(d, 1 H), 7.38~7.42(m, 2 H), 6.95(d, 1 H), 6.82~6.86(m, 2 H), 6.55(q, 1 H), 3.61(q, 2 H), 3.21(t, 4 H), 2.65~2.70(m, 6 H), 2.27(s, 3 H)<br>Exact Mass (calc.): 381.81 LC-MS (ESI+) m/e (M + 1)+: 382 |
| 191 | 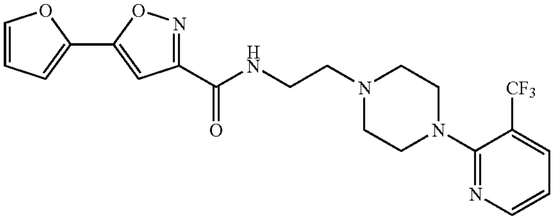 | $^1$H-NMR($CDCl_3$, 200 MHz), ppm(δ): 8.42(d, 1 H), 7.86(dd, 1 H), 7.58(d, 1 H), 7.41(bs, 1 H), 6.94~7.01(m, 2 H), 6.86(d, 1 H), 6.56(q, 1 H), 3.60(t, 2 H), 3.35(t, 4 H), 2.64~2.70(m, 6 H)<br>Exact Mass (calc.): 435.15 LC-MS (ESI+) m/e (M + 1)+: 436 |
| 192 | 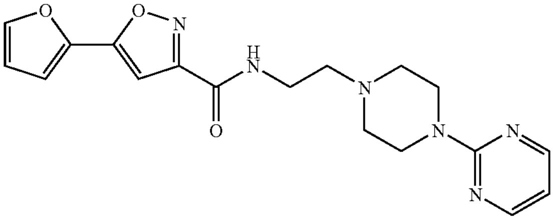 | $^1$H-NMR($CDCl_3$, 200 MHz), ppm(δ): 8.31(dd, 2 H), 7.59(d, 1 H), 7.40(bs, 1 H), 6.96(d, 1 H), 6.88(s, 1 H), 6.57(q, 1 H), 6.50(t, 1 H), 3.87(t, 4 H), 3.62(q, 2 H), 2.66(t, 2 h), 2.58(t, 4 H)<br>Exact Mass (calc.): 368.16 LC-MS (ESI+) m/e (M + 1)+: 369 |
| 193 | 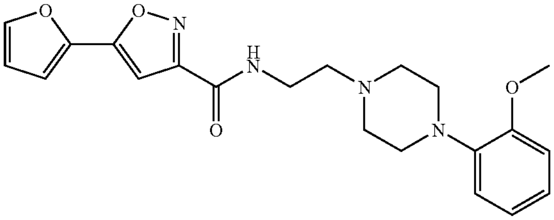 | $^1$H-NMR($CDCl_3$, 200 MHz), ppm(δ): 7.59(s, 1 H), 7.38(bs, 1 H), 6.84~7.06(m, 6 H), 6.56(q, 1 H), 3.88(s, 3 H), 3.63(q, 2 H), 3.17(bs, 4 H), 2.69~2.78(m, 6 H)<br>Exact Mass (calc.): 396.18 LC-MS (ESI+) m/e (M + 1)+: 397 |

TABLE 24-continued

| | | |
|---|---|---|
| 194 | 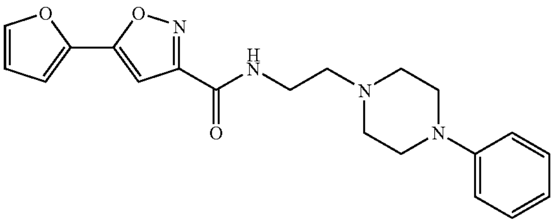 | $^1$H-NMR($CDCl_3$, 200 MHz), ppm(δ):<br>7.59(s, 1 H), 7.25~7.33(m, 4 H), 6.93~6.97(m, 4 H),<br>6.88(s, 1 H), 6.57(q, 1 H), 3.61(q, 2 H), 3.25(t, 4 H),<br>2.65~2.51(m, 6 H)<br>Exact Mass (calc.): 366.17 LC-MS (ESI+) m/e<br>(M + 1)+: 367 |
| 195 | 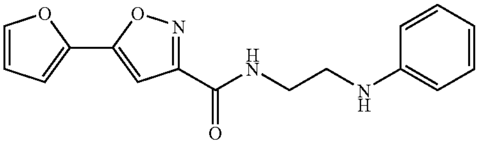 | $^1$H-NMR($CDCl_3$, 200 MHz), ppm(δ): 7.59(t, 1 H),<br>7.17~7.28(m, 3 H), 6.96(d, 1 H), 6.88(s, 1 H), 6.75(t,<br>1 H), 6.69(dd, 1 H), 6.58(dd, 1 H), 4.04(bs, 1 H),<br>3.73(q, 2 H), 3.43(t, 2 H)<br>Exact Mass (calc.): 297.11 LC-MS (ESI+) m/e<br>(M + 1)+: 298 |
| 196 | 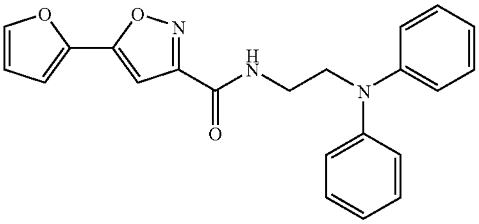 | $^1$H-NMR($CDCl_3$, 200 MHz), ppm(δ): 7.57(d, 1 H),<br>7.39(bs, 1 H), 7.21~7.36(m, 9 H), 6.92(d, 1 H), 6.86(d,<br>2 H), 6.55(q, 1 H), 4.14(q, 2 H), 3.92(t, 2 H)<br>Exact Mass (calc.): 373.14 LC-MS (ESI+) m/e<br>(M + 1)+: 374 |

TABLE 25

| | | |
|---|---|---|
| 197 | 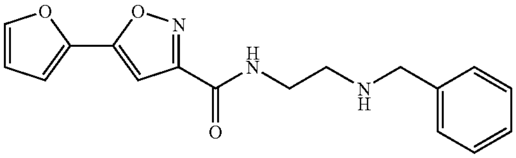 | $^1$H-NMR($CDCl_3$, 500 MHz), ppm(δ): 7.58(d, 1 H),<br>7.31~7.34(m, 5 H), 7.25(s, 1 H), 6.96(d, 1 H), 6.86(s,<br>1 H), 6.56(q, 1 H), 3.83(s, 2 H), 3.68(q, 2 H), 2.89(t,<br>2 H)<br>Exact Mass (calc.): 311.13 LC-MS (ESI+) m/e<br>(M + 1)+: 312 |
| 198 | 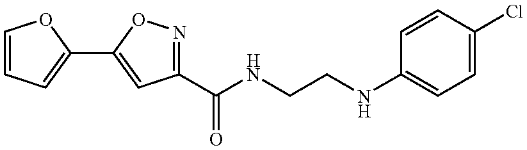 | $^1$H-NMR($CDCl_3$, 500 MHz), ppm(δ): 7.58(s, 1 H),<br>7.11~7.14(m, 3 H), 6.96(d, 1 H), 6.86(s, 1 H),<br>6.56~6.58(m, 3 H), 4.07(bs, 1 H), 3.70(q, 2 H), 3.38(t,<br>2 H)<br>Exact Mass (calc.): 331.07 LC-MS (ESI+) m/e<br>(M + 1)+: 332 |
| 199 | 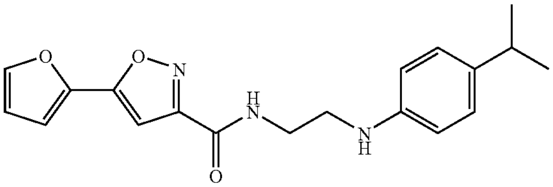 | $^1$H-NMR($CDCl_3$, 500 MHz), ppm(δ): 7.58(d, 1 H),<br>7.11(bs, 1 H), 7.06(d, 2 H), 6.95(d, 1 H), 6.86(s, 1 H),<br>6.62(d, 2 H), 6.56(q, 1 H), 3.70(q, 2 H), 3.40(t, 2 H),<br>2.81(dt, 1 H), 2.26(d, 6 H)<br>Exact Mass (calc.): 339.16 LC-MS (ESI+) m/e<br>(M + 1)+: 340 |
| 200 | 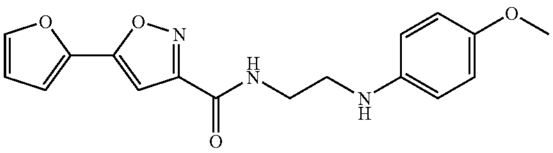 | $^1$H-NMR($CDCl_3$, 500 MHz), ppm(δ): 7.58(s, 1 H),<br>7.12(bs, 1 H), 6.95(s, 1 H), 6.86(s, 1 H), 6.78~6.81(m,<br>2 H), 6.65(q, 1 H), 6.62(d, 1 H), 6.55(d, 1 H), 3.89(s,<br>3 H), 3.71(q, 2 H), 3.37(t, 2 H)<br>Exact Mass (calc.): 327.12 LC-MS (ESI+) m/e<br>(M + 1)+: 328 |
| 201 | 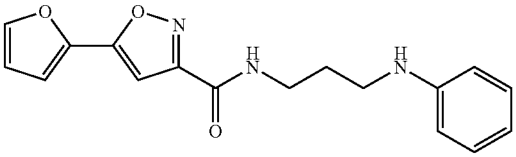 | $^1$H-NMR($CDCl_3$, 500 MHz), ppm(δ): 7.58(s, 1 H),<br>7.19(q, 2 H), 7.02(bs, 1 H), 6.95(d, 1 H), 6.86(s, 1 H),<br>6.17(dd, 2 H), 6.57(d, 1 H), 6.56(s, 1 H), 3.60(q, 2 H),<br>3.26(t, 2 H), 1.94(dt, 2 H), 1.63(bs, 1 H)<br>Exact Mass (calc.): 311.13 LC-MS (ESI+) m/e<br>(M + 1)+: 312 |

TABLE 25-continued

| | | |
|---|---|---|
| 202 | 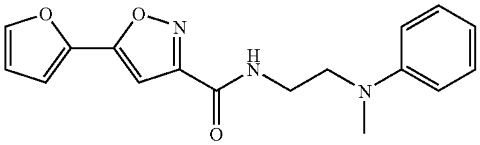 | $^1$H-NMR($CDCl_3$, 500 MHz), ppm(δ): 7.58(s, 1 H), 7.24~7.27(m, 1 H), 7.01(bs, 1 H), 6.95(d, 1 H), 6.86(s, 1 H), 6.79(d, 2 H), 6.74(t, 1 H), 6.56(d, 1 H), 3.67(t, 2 H), 3.59(t, 2 H), 3.00(s, 3 H) Exact Mass (calc.): 311.13 LC-MS (ESI+) m/e (M + 1)+: 312 |

TABLE 26

| | | |
|---|---|---|
| 203 | 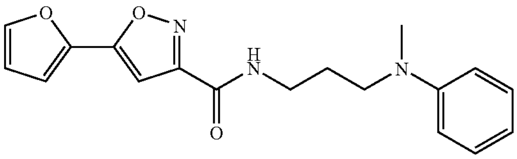 | $^1$H-NMR($CDCl_3$, 200 MHz), ppm(δ): 7.60(s, 1 H), 7.26(t, 2 H), 7.05(bs, 1 H), 6.97(d, 1 H), 6.88(s, 1 H), 6.71~6.79(m, 3 H), 6.58(q, 1 H), 3.50(dt, 4 H), 2.97(s, 3 H), 2.05(dt, 2 H) Exact Mass (calc.): 325.14 LC-MS (ESI+) m/e (M + 1)+: 326 |
| 204 | 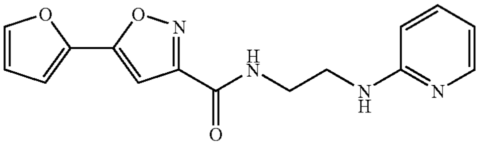 | $^1$H-NMR(Acetone-$d_6$, 500 MHz), ppm(δ): 8.35(bs, 1 H), 8.01(d, 2 H), 7.81(s, 1 H), 7.21(bs, 1 H), 7.13(d, 1 H), 6.86~6.91(m, 2 H), 6.69(s, 1 H), 3.67(dd, 2 H), 3.15(bs, 1 H), 2.05(d, 2 H) Exact Mass (calc.): 298.11 LC-MS (ESI+) m/e (M + 1)+: 299 |
| 205 | 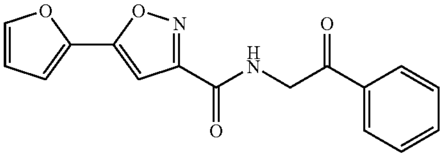 | $^1$H-NMR(DMSO-$d_6$, 200 MHz), ppm(δ): 9.09(t, J = 5.80, 1 H), 8.15~7.99(m, 3 H), 7.78~7.52(m, 3 H), 7.38~7.25(m, 1 H), 7.13(s, 1 H), 6.85~6.76(m, 1 H), 4.82(d, J = 6.00, 2 H) Exact Mass (calc.): 296.28 LC-MS (ESI+) m/e (M + 1)+: 297 |
| 206 | 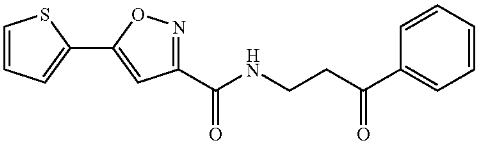 | $^1$H-NMR($CDCl_3$, 200 MHz), ppm(δ): 7.98~7.95(m, 2 H), 7.60~7.44(m, 6 H), 7.13~7.11(m, 1 H), 6.79(s, 1 H), 3.92~3.85(m, 2 H), 3.35(t, J = 5.85, 2 H) Exact Mass (calc.): 326.37 LC-MS (ESI+) m/e (M + 1)+: 327 |
| 207 | 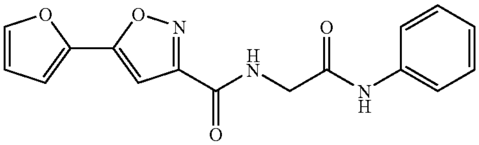 | $^1$H-NMR(DMSO-$d_6$, 200 MHz), ppm(δ): 10.08(s, 1 H), 9.19~8.99(m, 1 H), 8.01(s, 1 H), 7.62~6.99(m, 7 H), 6.83~6.75(m, 1 H), 4.08(d, J = 6.40, 2 H) Exact Mass (calc.): 311.30 LC-MS (ESI+) m/e (M + 1)+: 312 |
| 208 | 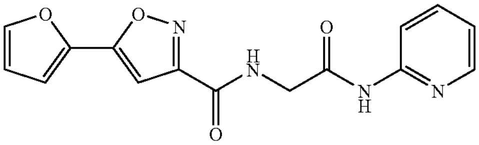 | $^1$H-NMR(DMSO-$d_6$, 200 MHz), ppm(δ): 10.66(s, 1 H), 9.07(t, 1 H), 8.33(d, 1 H), 8.07(s, 1 H), 8.02(d, 1 H), 7.79(t, 1 H), 7.27(d, 1 H), 7.11(t, 2 H), 6.77(t, 1 H), 3.36(s, 2 H |
| 209 | 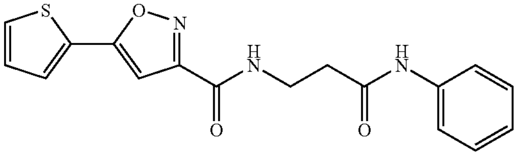 | $^1$H-NMR(DMSO-$d_6$, 200 MHz), ppm(δ): 9.99(s, 1 H), 8.88(t, J = 5.65, 1 H), 7.89~7.86(m, 1 H), 7.81~7.78(m, 1 H), 7.60(d, J = 7.65, 2 H), 7.32~7.25(m, 3 H), 7.20(s, 1 H), 7.06~7.01(m, 1 H), 3.59~3.53(m, 2 H), 2.65(t, J = 7.10, 2 H) Exact Mass (calc.): 341.39 LC-MS (ESI+) m/e (M + 1)+: 342 |

TABLE 27

| | | |
|---|---|---|
| 210 | 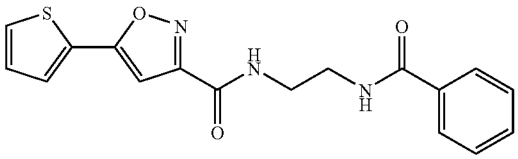 | $^1$H-NMR(DMSO-$d_6$, 200 MHz), ppm(δ): 8.96~8.90(m, 1 H), 8.63~8.56(m, 1 H), 7.89~7.79(m, 4 H), 7.55~7.43(m, 3 H), 7.30~7.25(m, 1 H), 7.20(s, 1 H), 3.52~3.42(m, 4 H) Exact Mass (calc.): 341.39 LC-MS (ESI+) m/e (M + 1)+: 342 |
| 211 | 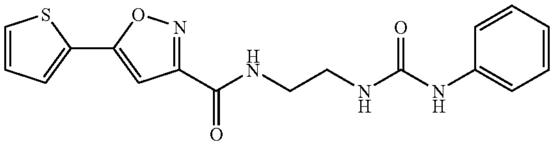 | $^1$H-NMR(DMSO-$d_6$, 200 MHz), ppm(δ): 8.87(t, J = 5.40, 1 H), 8.54(s, 1 H), 7.89~7.86(m, 1 H), 7.81~7.78(m, 1 H), 7.39(d, J = 7.70, 2 H), 7.29~7.18(m, 4 H), 6.91~6.86(m, 1 H), 6.28(t, J = 5.70, 1 H), 3.39~3.28(m, 4 H) Exact Mass (calc.): 356.40 LC-MS (ESI+) m/e (M + 1)+: 357 |
| 212 | 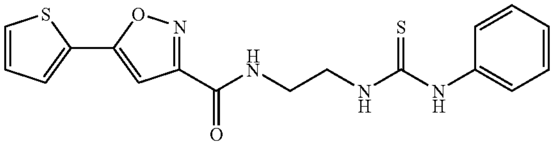 | $^1$H-NMR(DMSO-$d_6$, 200 MHz), ppm(δ): 9.73(s, 1 H), 8.30~8.11(m, 1 H), 7.90~7.78(m, 2 H), 7.36~7.00(m, 6 H), 6.93~6.86(m, 1 H), 6.50~6.35(m, 1 H), 3.40~3.25(m, 4 H) Exact Mass (calc.): 372.07 LC-MS (ESI+) m/e (M + 1)+: 373 |
| 213 | 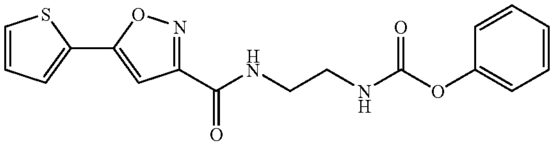 | $^1$H-NMR(DMSO-$d_6$, 200 MHz), ppm(δ): 8.89~8.84(m, 1 H), 7.88~7.79(m, 2 H), 7.36~7.11(m, 6 H), 6.92~6.86(m, 1 H), 6.30~6.18(m, 1 H), 3.43~3.30(m, 4 H) Exact Mass (calc.): 357.08 LC-MS (ESI+) m/e (M + 1)+: 358 |
| 214 | 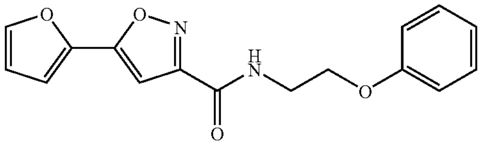 | $^1$H-NMR($CDCl_3$, 500 MHz), ppm(δ): 8.36(s, 1 H), 7.80(q, 1 H), 7.63~7.65(m, 2 H), 7.51(d, 2 H), 7.18~7.22(m, 3 H), 6.93(q, 1 H), 6.71(d, 1 H), 1.99(d, 4 H) Exact Mass (calc.): 298.10 LC-MS (ESI+) m/e (M + 1)+: 299 |
| 215 | 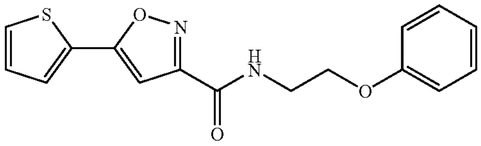 | $^1$H-NMR($CDCl_3$, 500 MHz), ppm(δ): 7.54(s, 1 H), 7.48(d, 1 H), 7.28~7.31(m, 3 H), 7.14(t, 1 H), 6.92(d, 1 H), 6.93~6.99(m, 2 H), 6.82(s, 1 H), 4.15(t, 2 H), 3.88(q, 2 H) Exact Mass (calc.): 314.07 LC-MS (ESI+) m/e (M + 1)+: 315 |
| 216 | 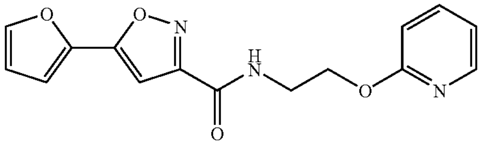 | $^1$H-NMR($CDCl_3$, 500 MHz), ppm(δ): 8.18(dd, 1 H), 7.76(bs, 1 H), 7.59(t, 1 H), 6.89~6.95(m, 2 H), 6.86(s, 1 H), 6.78(d, 1 H), 6.55(s, 1 H), 4.54(t, 2 H), 3.67(q, 2 H) Exact Mass (calc.): 299.09 LC-MS (ESI+) m/e (M + 1)+: 300 |

TABLE 28

| | | |
|---|---|---|
| 217 | 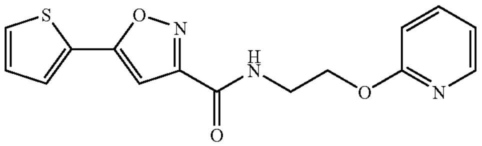 | $^1$H-NMR($CDCl_3$, 500 MHz), ppm(δ): 8.18(d, 1 H), 7.76(bs, 1 H), 7.60(t, 1 H), 7.54(s, 1 H), 7.48(d, 1 H), 7.14(t, 1 H), 6.91(t, 1 H), 6.79(t, 1 H), 4.54(t, 2 H), 3.87(q, 2 H) Exact Mass (calc.): 315.07 LC-MS (ESI+) m/e (M + 1)+: 316 |
| 218 | 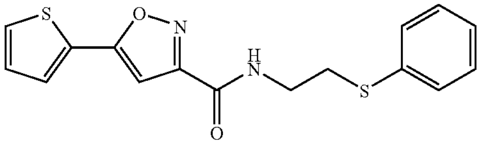 | $^1$H-NMR(DMSO-$d_6$, 500 MHz), ppm(δ): 9.02(m, 1 H), 7.89(m, 1 H), 7.82(m, 1 H), 7.42(m, 2 H), 7.34(m, 2 H), 7.28(m, 2 H), 7.21(m, 2 H), 3.47(m, 2 H), 3.15(m, 2 H) Exact Mass (calc.): 330.05 LC-MS (ESI+) m/e (M + 1)+: 331 |

TABLE 28-continued

| | | |
|---|---|---|
| 219 | 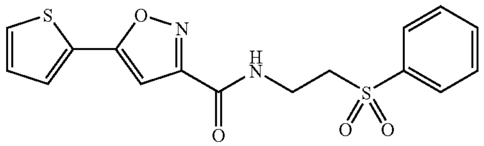 | $^1$H-NMR(DMSO-$d_6$, 500 MHz), ppm(δ): 8.79(m, 1 H), 7.91(m, 1 H), 7.86(m, 1 H), 7.78(m, 1 H), 7.71(m, 1 H), 7.64(m, 2 H), 7.25(m, 1 H), 7.11(s, 1 H), 3.60(m, 2 H), 3.55(m, 2 H)<br>Exact Mass (calc.): 362.04 LC-MS (ESI+) m/e (M + 1)+: 363 |
| 220 | 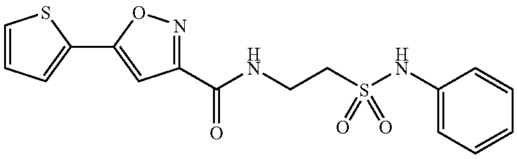 | $^1$H-NMR(DMSO-$d_6$, 500 MHz), ppm(δ): 9.89(s,. 1 H), 8.80(m, 1 H), 7.88(m, 1 H), 7.80(m, 1 H), 7.33(t, 2 H), 7.28(t, 1 H), 7.23(m, 2 H), 7.16(s, 1 H), 7.12(t, 2 H), 3.65(m, 2 H), 3.36(m, 2 H)<br>Exact Mass (calc.): 377.05 LC-MS (ESI+) m/e (M + 1)+: 378 |
| 221 | 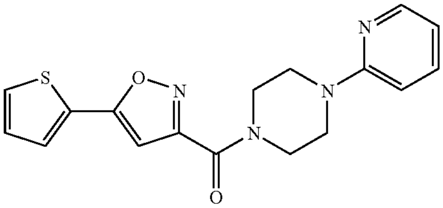 | $^1$H-NMR(acetone-$d_6$, 200 MHz), ppm(δ): 8.24~8.16(m, 1 H), 7.86~7.74(m, 2 H), 7.64~7.54(m, 1 H), 7.34~7.26(m, 1 H), 6.97(s, 1 H), 6.92~6.85(m, 1 H), 6.74~6.66(m, 1 H), 3.99~3.62(m, 8 H)<br>Exact Mass (calc.): 340.41 LC-MS (ESI+) m/e (M + 1)+: 341 |
| 222 | 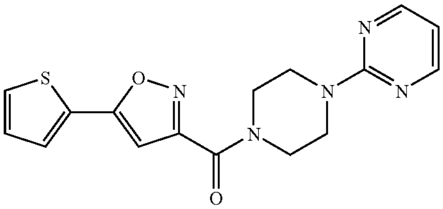 | $^1$H-NMR(acetone-$d_6$, 200 MHz), ppm(δ): 8.46~8.35(m, 2 H), 7.86~7.74(m, 2 H), 7.34~7.26(m, 1 H), 6.98(s, 1 H), 6.70~6.63(m, 1 H), 3.99~3.81(m, 8 H)<br>Exact Mass (calc.): 341.39 LC-MS (ESI+) m/e (M + 1)+: 342 |
| 223 | 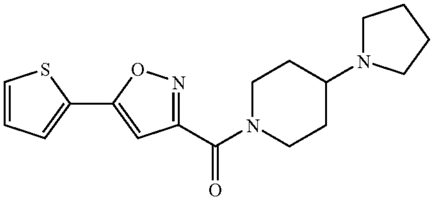 | $^1$H-NMR(acetone-$d_6$, 200 MHz), ppm(δ): 7.84~7.73(m, 2 H), 7.32~7.25(m, 1 H), 6.91(s, 1 H), 3.45~3.07(m, 2 H), 2.65~2.52(m, 5 H), 2.46~2.29(m, 1 H), 2.12~1.88(m, 2 H), 1.81~1.68(m, 5 H), 1.65~1.44(m, 2 H)<br>Exact Mass (calc.): 331.44 LC-MS (ESI+) m/e (M + 1)+: 332 |

TABLE 29

| | | |
|---|---|---|
| 224 | 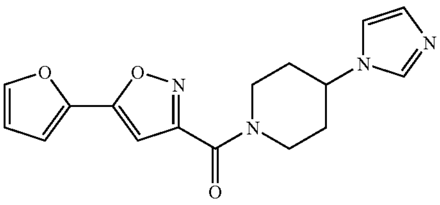 | Exact Mass (calc.): 312.12 LC-MS (ESI+) m/e (M + 1)$^+$: 313 |

Preparation Example 2

Preparation of N-(5-furan-2-yl-isoxazol-3-yl)-3-pyridin-2-yl-acryl amide (Derivative (225))

The isoxazole derivative was prepared via the reaction routes of the following Reaction Formula 4.

Reaction Formula 4

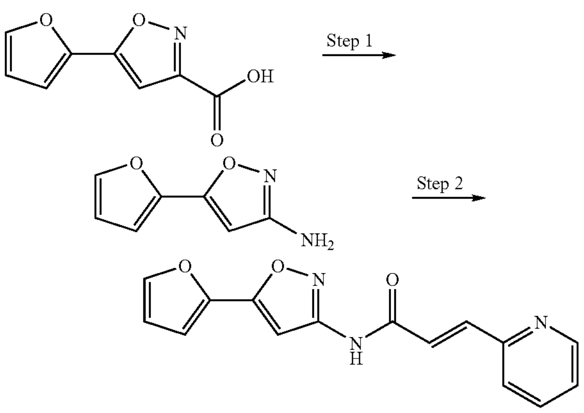

1) Step 1: Preparation of 5-furan-2-yl-isoxazol-3-ylamine

To a solution of 2.0 g of 5-furan-2-yl-isoxazole-3-carboxylic acid and 6.2 mL of TEA in benzene was added 3.61 mL of DPPA at room temperature. After refluxing for 1.5 hrs, 30 mL of distilled water was added and then the resulting solution was refluxed for an additional 30 min. The reaction solution was concentrated under reduced pressure, and the concentrate was purified by column chromatography on silica gel to obtain 0.6 g of 5-furan-2-yl-isoxazol-3-ylamine (Yield: 40%).

NMR (acetone-$d_6$, 200 MHz), ppm(δ): 7.75~7.73 (m, 1H), 6.91~6.88 (m, 1H), 6.66~6.61 (m, 1H), 6.15 (s, 1H), 5.18 (br s, 2H)

2) Step 2: Preparation of N-(5-furan-2-yl-isoxazol-3-yl)-3-pyridin-2-yl-acrylamide To a solution of 6 mg of 3-pyridin-2-yl-acrylic acid and 6 mg of 5-furan-2-yl-isoxazol-3-ylamine in DMF were added 8 mg of HOBt, 9 mg of EDC and 0.014 mL of TEA. The reaction solution was stirred for 18 hrs at room temperature, followed by concentration under reduced pressure. The concentrate was purified by preparative HPLC to provide 4 mg of N-(5-furan-2-yl-isoxazol-3-yl)-3-pyridin-2-yl-acrylamide. (Yield: 36%).

NMR (acetone-$d_6$, 200 MHz), ppm(δ): 8.71~8.63 (m, 1H), 7.94~7.61 (m, 4H), 7.46~7.36 (m, 1H), 7.20~6.88 (m, 3H), 6.66~6.61 (m, 1H), 6.16 (s, 1H); Exact Mass (calc.): 281.08 LC-MS (ESI+) m/e (M+1)+: 282.

From suitable starting materials, the following Derivatives (226)~(232) were prepared in processes similar to those for the isoxazole derivative (225), and the results are given in Table 30, below.

TABLE 30

| Cpd. No. | Structure | Results |
|---|---|---|
| 226 | 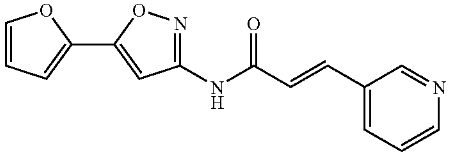 | Exact Mass (calc.): 281.08 LC-MS ($ESI^+$) m/e $(M + 1)^+$: 282 |
| 227 | 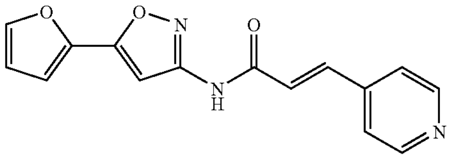 | Exact Mass (calc.): 281.08 LC-MS ($ESI^+$) m/e $(M + 1)^+$: 282 |
| 228 | 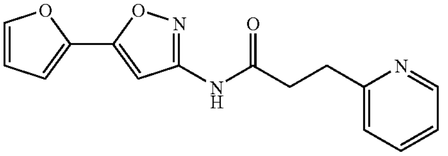 | Exact Mass (calc.): 283.10 LC-MS ($ESI^+$) m/e $(M + 1)^+$: 284 |
| 229 | 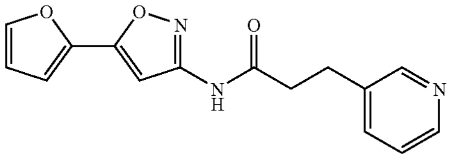 | Exact Mass (calc.): 283.10 LC-MS ($ESI^+$) m/e $(M + 1)^+$: 284 |

TABLE 30-continued

| Cpd. No. | Structure | Results |
|---|---|---|
| 230 | 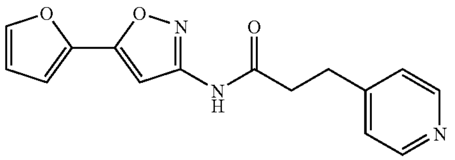 | Exact Mass (calc.): 283.10 LC-MS (ESI$^+$) m/e (M + 1)$^+$: 284 |
| 231 | 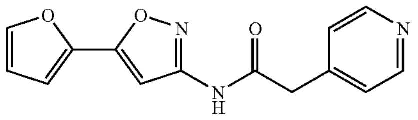 | Exact Mass (calc.): 269.08 LC-MS (ESI$^+$) m/e (M + 1)$^+$: 270 |
| 232 | 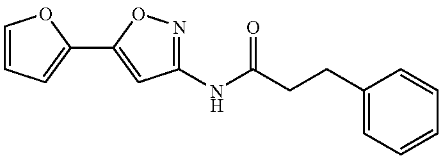 | Exact Mass (calc.): 282.10 LC-MS (ESI$^+$) m/e (M + 1)$^+$: 283 |

Preparation Example 3

Preparation of N-(5-furan-2-yl-isoxazol-3-ylmethyl)-2-phenyl-acetamide (Derivative (233))

The isoxazole derivative was prepared via the reaction routes of the following Reaction Formula 5.

Reaction Formula 5

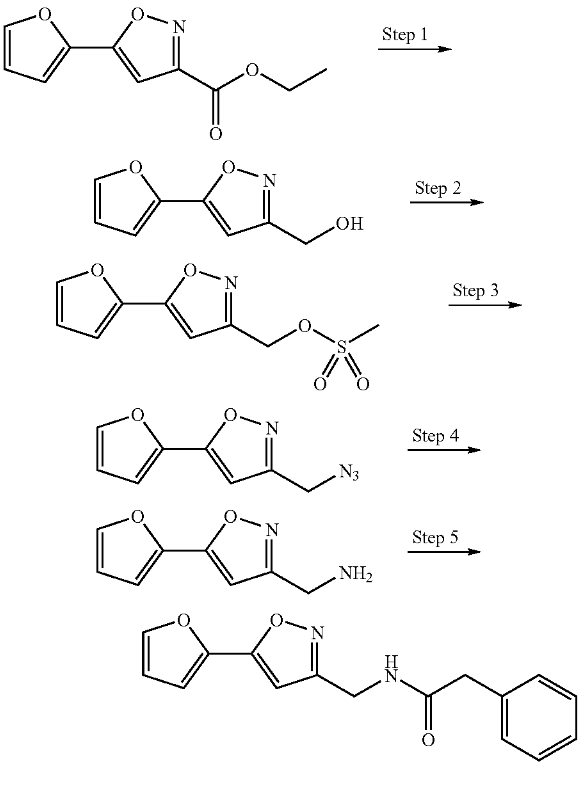

1) Step 1: Preparation of (5-furan-2-yl-isoxazol-3-yl)-methanol

To a solution of 2.00 g of 5-furan-2-yl-isoxazole-3-carboxylic acid ethyl ester in absolute ethanol was slowly added 548 mg of sodiumborohydride at 0° C. After stirring at room temperature for 4 hrs, the reaction was quenched by addition of distilled water. The reaction solution was concentrated under reduced pressure and extracted with methylene chloride. The organic layer was dried over anhydrous sodium sulfate, filtered and concentrated in vacuo to produce 1.41 g of (5-furan-2-yl-isoxazol-3-yl)-methanol. (Yield 88%). This concentrate was used in the next step without further purification.

NMR (acetone-$d_6$, 200 MHz), ppm(δ): 7.82~7.78 (m, 1H), 7.05~7.00 (m, 1H), 6.71~6.63 (m, 2H), 4.71 (s, 2H)

2) Preparation 2: Preparation of methanesulfonic acid 5-furan-2-yl-isoxazol-3-ylmethyl ester To a solution of 1.41 g of (5-furan-2-yl-isoxazol-3-yl)-methanol and 1.77 mL of TEA in 45 mL of methylene chloride was slowly added 0.73 mL of methanesulfonyl chloride at 0° C. After stirring for 1 hr, the reaction solution was washed with water and 1N HCl, dried over anhydrous sodium sulfate, filtered and concentrated in vacuo to provide 10.0 g of methanesulfonic acid 5-furan-2-yl-isoxazol-3-ylmethyl ester. This concentrate was used for the next step without further purification.

NMR (acetone-d, 200 MHz), ppm(δ): 7.86~7.84 (m, 1H), 7.15~7.19 (m, 1H), 6.85 (s, 1H), 6.74~6.71 (m, 1H), 5.43 (s, 2H), 3.26 (s, 3H)

3) Step 3: Preparation of 3-azidomethyl-5-furan-2-yl-isoxazole

To a solution of 2.21 g of methane sulfonic acid 5-furan-2-yl-isoxazol-3-ylmethyl ester in 45 mL of DMF was added 0.61 g of sodium azide. After stirring for 15 hrs, the reaction mixture was concentrated under reduced pressure. The residue was dissolved in methylene chloride and distilled water, and the organic layer was separated. The organic layer was dried over anhydrous sodium sulfate, filtered and concentrated in vacuo to afford 1.50 g of 3-azidomethyl-5-furan-2-yl-isoxazole. This concentrate was used in the next step without further purification.

NMR (acetone-$d_6$, 200 MHz), ppm(δ): 7.85~7.83 (m, 1H), 7.12~7.08 (m, 1H), 6.77 (s, 1H), 6.74~6.70 (m, 1H), 4.62 (s, 2H)

4) Step 4: Preparation of C-(5-furan-2-yl-isoxazol-3-yl)-methylamine

A solution of 1.50 g of 3-azidomethyl-5-furan-2-yl-isoxazole and 600 mg of 5% palladium in 50 ml of methanol was stirred for 15 hrs under hydrogen atmosphere and then filtered. The filtrate was concentrated in vacuo to provide 821 mg of C-(5-furan-2-yl-isoxazol-3-yl)-methylamine (Step 3 Yield 59%). This concentrate was used in the next step without further purification.

NMR ($CD_3OD$, 200 MHz), ppm(δ): 7.84~7.81 (m, 1H), 7.12~7.08 (m, 1H), 6.75 (s, 1H), 6.72~6.70 (m, 1H), 4.91 (s, 2H)

5) Step 5: Preparation of N-(5-furan-2-yl-isoxazol-3-ylmethyl)-2-phenyl-acetamide To a solution of 7 mg of phenylacetic acid and 5 mg of C-(5-furan-2-yl-isoxazol-3-yl)-methylamine in DMF were added 8 mg of HOBt, 9 mg of EDC and 0.02 mL of TEA. After stirring at room temperature for 18 hrs, the reaction mixture was concentrated in vacuo. The concentrate was purified by preparative HPLC to produce 4 mg of the isoxazole derivative (Yield: 35%).

NMR (acetone-$d_6$, 200 MHz), ppm(δ): 7.83~7.79 (m, 1H), 7.20~6.80 (m, 7H), 6.74 (s, 1H), 6.71~6.68 (m, 1H), 4.51 (s, 2H), 3.62 (s, 2H); Exact Mass (calc.): 282.10 LC-MS (ESI+) m/e (M+1)+: 283.

From suitable starting materials, the following Derivatives (234)~(240) were prepared in processes similar to those for the isoxazole derivative (233), and the results are given in Table 31, below.

TABLE 31

| Cpd. No. | Structure | Results |
|---|---|---|
| 234 | 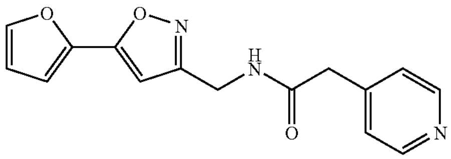 | Exact Mass (calc.): 283.10 LC-MS ($ESI^+$) m/e $(M + 1)^+$: 284 |
| 235 | 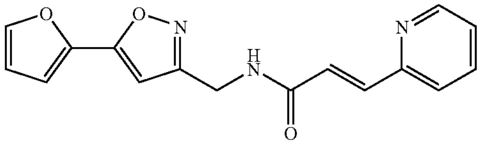 | Exact Mass (calc.): 295.10 LC-MS ($ESI^+$) m/e $(M + 1)^+$: 296 |
| 236 | 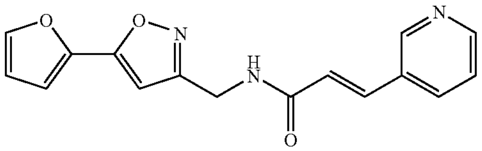 | Exact Mass (calc.): 295.10 LC-MS ($ESI^+$) m/e $(M + 1)^+$: 296 |
| 237 | 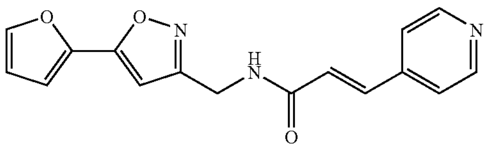 | Exact Mass (calc.): 295.10 LC-MS ($ESI^+$) m/e $(M + 1)^+$: 296 |
| 238 | 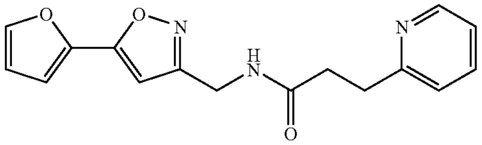 | Exact Mass (calc.): 297.11 LC-MS ($ESI^+$) m/e $(M + 1)^+$: 298 |
| 239 | 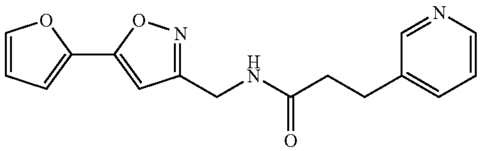 | Exact Mass (calc.): 297.11 LC-MS ($ESI^+$) m/e $(M + 1)^+$: 298 |

TABLE 31-continued

| Cpd. No. | Structure | Results |
|---|---|---|
| 240 | 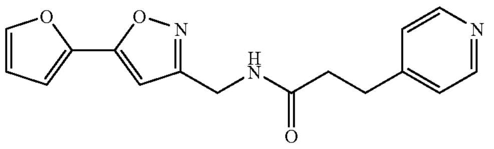 | Exact Mass (calc.): 297.11 LC-MS ($ESI^+$) m/e $(M + 1)^+$: 298 |

Preparation Example 4

Preparation of 1-benzyl-3-(5-furan-2-yl-isoxazol-3-yl)-urea (Derivative (241))

The isoxazole derivative was prepared via the reaction routes of the following Reaction Formula 6.

Reaction Formula 6

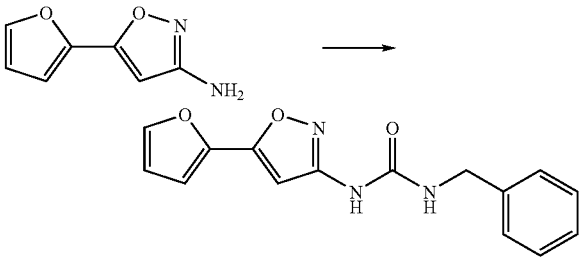

To a solution of 9 mg of 5-furan-2-yl-isoxazol-3-ylamine in 0.5 mL of methylene chloride were added 10 mg of CDI and 0.008 mL of TEA. After stirring at room temperature for 4 hrs, 6 mg of benzylamine was added. The resulting solution was then refluxed for 18 hrs. The reaction mixture was washed with 1N HCl and water, dried over anhydrous sodium sulfate, filtered, and concentrated under reduced pressure. The concentrate was purified by preparative HPLC to provide 8 mg of the title compound. (Yield: 45%).

1H-NMR (acetone $d_6$, 200 MHz), ppm(δ): 8.47 (bs, 1H), 7.79~7.70 (m, 1H), 7.50~6.60 (m, 7H), 6.15 (s, 1H), 5.80~5.71 (m, 2H), 4.62 (d, 2); Exact Mass (calc.): 283.10 LC-MS ($ESI^{30}$) m/e (M+1)+: 284.

From suitable starting materials, the following Derivatives (242)~(250) were prepared in processes similar to those for the isoxazole derivative (241), and the results are given in Table 32, below.

TABLE 32

| Cpd. No. | Structure | Results |
|---|---|---|
| 242 | 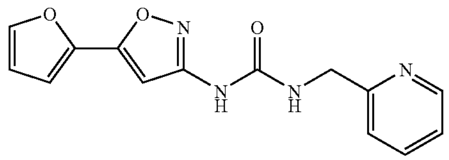 | Exact Mass (calc.): 284.09 LC-MS ($ESI^+$) m/e $(M + 1)^+$: 285 |
| 243 | 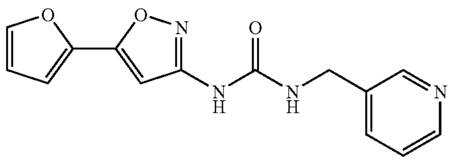 | Exact Mass (calc.): 284.09 LC-MS ($ESI^+$) m/e $(M + 1)^+$: 285 |
| 244 | 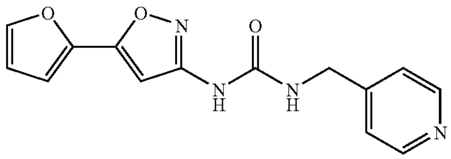 | Exact Mass (calc.): 284.09 LC-MS ($ESI^+$) m/e $(M + 1)^+$: 285 |
| 245 | 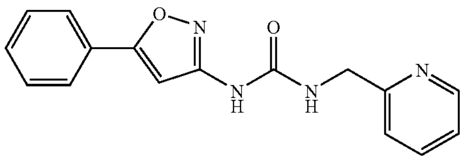 | Exact Mass (calc.): 294.11 LC-MS ($ESI^+$) m/e $(M + 1)^+$: 295 |

TABLE 32-continued

| Cpd. No. | Structure | Results |
|---|---|---|
| 246 | 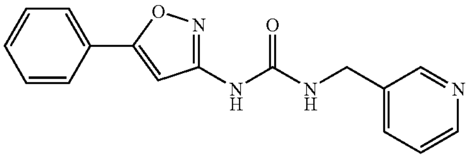 | Exact Mass (calc.): 294.11 LC-MS ($ESI^+$) m/e $(M + 1)^+$: 295 |
| 247 | 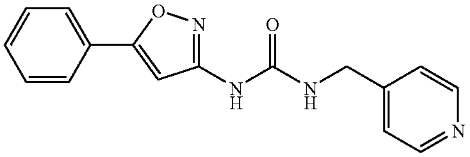 | Exact Mass (calc.): 294.11 LC-MS ($ESI^+$) m/e $(M + 1)^+$: 295 |
| 248 | 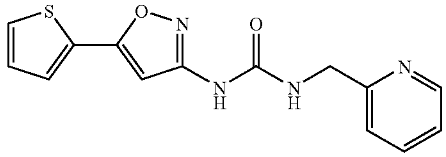 | Exact Mass (calc.): 300.07 LC-MS ($ESI^+$) m/e $(M + 1)^+$: 301 |
| 249 | 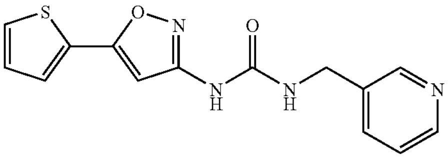 | Exact Mass (calc.): 300.07 LC-MS ($ESI^+$) m/e $(M + 1)^+$: 301 |
| 250 | 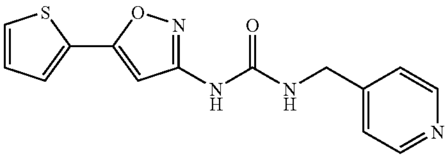 | Exact Mass (calc.): 300.07 LC-MS ($ESI^+$) m/e $(M + 1)^+$: 301 |

Preparation 5

Preparation of imidazole-1-carboxylic acid 5-furan-2-yl-isoxazol-3-ylmethyl ester (Derivative (251)) and 4-acetyl-piperazine-1-carboxylic acid 5-furan-2-yl-isoxazol-3-ylmethyl ester (Derivative (252))

The isoxazole derivative was prepared via the reaction routes of the following Reaction Formula 7.

Reaction Formula 7

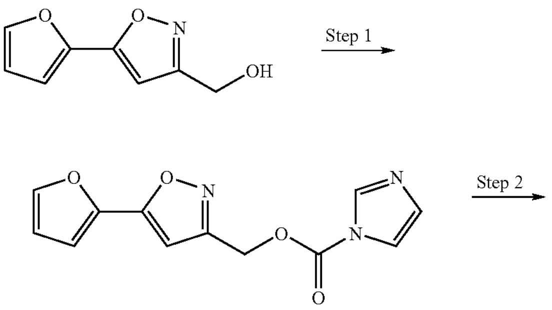

-continued

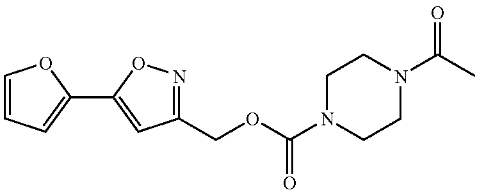

1) Step 1: Preparation of imidazole-1-carboxylic acid 5-furan-2-yl-isoxazol-3-ylmethyl ester (Derivative (251))

To a solution 200 mg of (5-furan-2-yl-isoxazol-3-yl)-methanol in 6 mL of methylene chloride was added 216 mg of CDI. After stirring at room temperature for 4 hrs, the reaction mixture was concentrated under reduced pressure. The concentrate was purified by column chromatography to afford 282 mg of the title compound. (Yield: 90%).

1H-NMR ($CDCl_3$, 200 MHz), ppm(δ): 8.19 (s, 1H), 7.58 (s, 1H), 7.47 (s, 1H), 7.11 (s, 1H), 6.97 (d, 1H), 6.56~6.58 (m, 2H), 5.54 (d, 1H); Exact Mass (calc.): 259.06 LC-MS (ESI+) m/e (M+1)+: 260.

2) Step 2: Preparation of 4-acetyl-piperazine-1-carboxylic acid 5-furan-2-yl-isoxazol-3-ylmethyl ester (Derivative (252))

To a solution of 30 mg of imidazole-1-carboxylic acid 5-furan-2-yl-isoxazol-3-ylmethyl ester in 1 mL of methylene chloride was added 16 mg of 1-piperazin-1-yl-ethanone. After stirring at room temperature for 4 hrs, the reaction mixture was concentrated under reduced pressure. The concentrate was purified by column chromatography to afford 30 mg of the title compound. (Yield: 79%).

1H-NMR (CDC3-$d_6$, 200 MHz), ppm(δ): 7.54 (d, 1H), 6.92 (d, 1H), 6.54 (q, 1H), 6.50 (s, 1H), 5.25 (s, 2H), 3.61 (bs, 4H), 3.51 (bs, 4H), 2.12 (s, 3H)); Exact Mass (calc.): 319.12 LC-MS (ESI+) m/e (M+1)+: 320.

From suitable starting materials, the following Derivatives (253)~(254) were prepared in processes similar to those for the isoxazole derivative (252), and the results are given in Table 33, below.

TABLE 33

| Cpd. No. | Structure | Results |
|---|---|---|
| 253 | 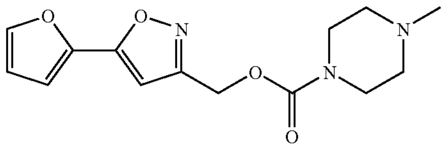 | $^1$H-NMR($CDCl_3$, 200 MHz), ppm(δ): 7.55(s, 1 H), 6.93(d, 1 H), 6.55(q, 1 H), 6.52(s, 1 H), 5.23(d, 2 H), 3.55(t, 4 H), 2.39(bs, 4 H), 2.32(d, 3 H) Exact Mass (calc.): 291.12 LC-MS ($ESI^+$) m/e $(M + 1)^+$: 292 |
| 254 | 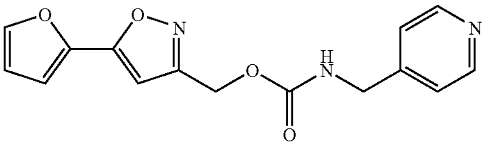 | $^1$H-NMR($CDCl_3$, 200 MHz), ppm(δ): 8.58(dd, 2 H), 7.56(t, 1 H), 7.23(d, 1 H), 6.92(d, 1 H), 6.55(q, 1 H), 6.51(s, 1 H), 5.46(bs, 1 H), 5.26(s, 1 H), 4.44(d, 2 H) Exact Mass (calc.): 299.09 LC-MS ($ESI^+$) m/e $(M + 1)^+$: 300 |

The compounds synthesized in Preparation Examples in accordance with the present invention were assayed for wnt/β-catenin signaling activity.

Experimental Example 1

Assessment of Activator for Wnt/β-Catenin Signaling Using Cell Strain (1) Construction of System for Assessing the Effect of Compound on Wnt/β-Catenin Signaling Using Cell Line In order to measure the in vitro activity of compounds of the present invention, two human cancer cell lines, HEK293 and SW480, which have intact Wnt signaling and show APC gene mutation in the Wnt signaling pathway, respectively, were used.

Figure 2:
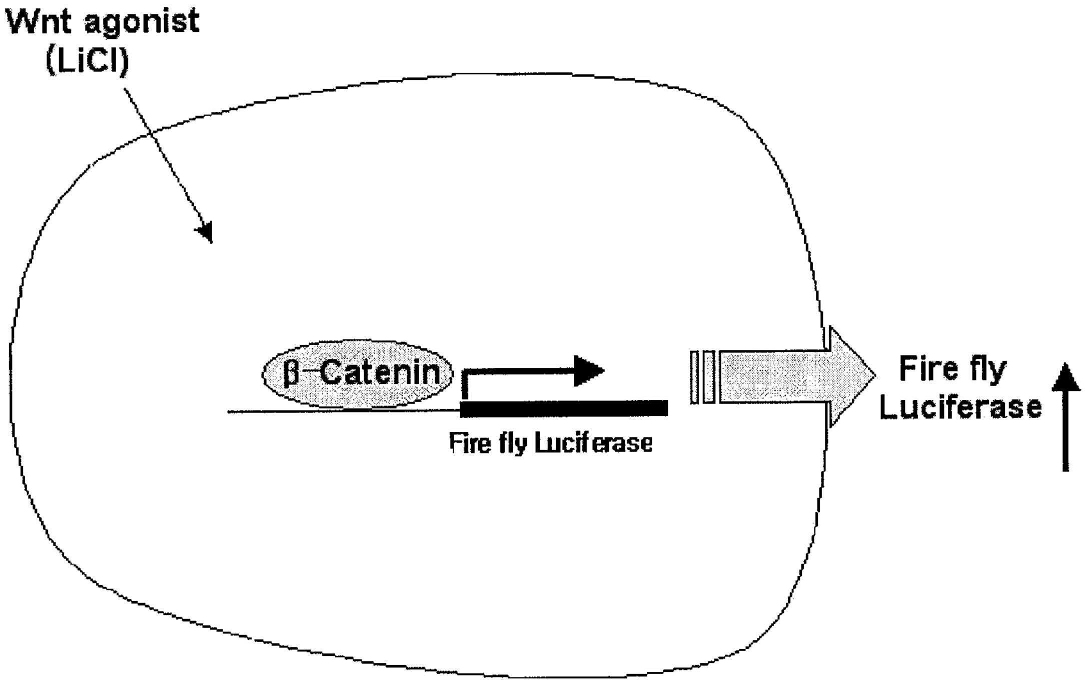
FIG. 2 is a conceptual diagram illustrating a cell-based screening system adapted to determine the effect of transcriptional activity of β-catenin.
Figure 3:
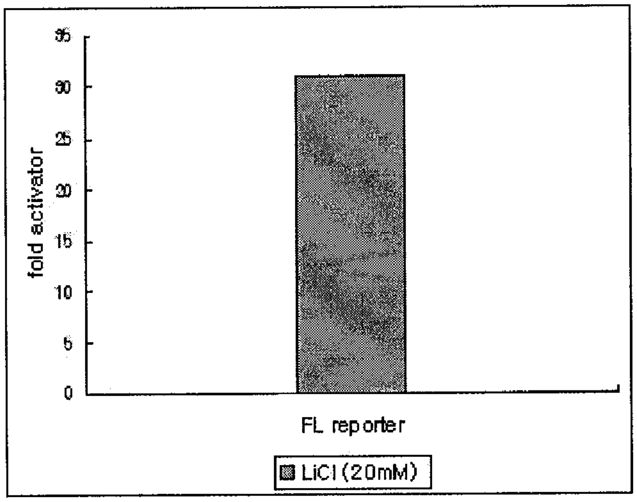
FIG. 3 is a bar graph showing a result of effect for the screening system of FIG. 2 obtained by applying lithium chloride, a well-known agonist of Wnt/β-catenin signaling.

For evaluating the activity of wnt/β-catenin signaling in the cancer cell lines, gene as illustrated in FIG. 1 having β-catenin-binding sites of the Tcf/Lef transcriptional control protein (5 sites of TCF, 5X TCF) and having a fire fly luficerase as a marker protein ascertainable the activity of 5X TCF was introduced into the cells. Treatment with G418 led monoclones of the cell lines, in which the genes were permanently expressed, so as to construct a cell-based Wnt agonist screening system. Subsequently, as illustrated in FIG. 2, the cell-based screening to indirectly identify β-catenin activity by quantitatively analyzing expressed luciferase using this system was carried out. For comparison with the activity of the isoxazole derivatives as Wnt agonists, lithium chloride (LiCl), acting as a positive control for the cell-based Wnt agonist screening system, was used to determine the expression level of the luciferase, and the results are shown in FIG. 3.

(2) Assay for the Activity of Isoxazole Derivatives in Wnt/β-Catenin Signaling

The cell lines, in which a cell-based Wnt agonist screening system was constructed, were cultured in RPMI 1640 media supplemented with penicillin-streptomycin (100 Units/mL) and heat-inactivated 5% fetal bovine serum under standard culture conditions (5% $CO_2$, 37° C., 100% relative humidity). Treatment with trypsin and dissociation with a pipette resulted in a single-cell suspension. The suspension was diluted with the same medium to adjust the cell count to 8,000~15,000 cells per well and was moved then in a 96-well microtiter plate. After being incubated for 24 hrs, the cells were treated with various concentrations of the isoxazole derivatives synthesized in Preparation Examples. Incubation for an additional 24 hours was followed by the quantitative analysis of luciferase activity using a Luciferase Assay kit (Promega, U.S.A.) according to the protocol described in the manual provided by the manufacturer. Data on the activities of the isoxazole derivatives thus synthesized are given in Tables 34 to 43, and are expressed as percentages relative to the activity of the positive control LiCl (20 mM), a well-known agonist of Wnt signaling.

TABLE 34

<Effect of Cpds. On β-catenin Activity in HEK293 Cell Line>

| | HEK293 (TCF-FL) | |
|---|---|---|
| Compounds | Max. Activity (%) | Conc. (μM) |
| Control (LiCl) | 100 | 20000 |
| Derivative (1) | 70 | 60 |
| Derivative (2) | <20 | 30 |
| Derivative (3) | <20 | 30 |
| Derivative (4) | <20 | 30 |
| Derivative (5) | <20 | 30 |
| Derivative (6) | <20 | 30 |

TABLE 35

| | | |
|---|---|---|
| Derivative (7) | <20 | 30 |
| Derivative (8) | <20 | 30 |
| Derivative (9) | <20 | 30 |

TABLE 35-continued

| | | |
|---|---|---|
| Derivative (10) | 32 | 120 |
| Derivative (11) | 61 | 30 |
| Derivative (12) | 109 | 60 |
| Derivative (15) | <20 | 30 |
| Derivative (16) | <20 | 30 |
| Derivative (17) | <20 | 30 |
| Derivative (18) | <20 | 30 |
| Derivative (20) | <20 | 30 |
| Derivative (21) | 23 | 30 |
| Derivative (22) | <20 | 30 |
| Derivative (23) | <20 | 30 |
| Derivative (25) | <20 | 30 |
| Derivative (26) | <20 | 30 |
| Derivative (27) | <20 | 30 |
| Derivative (28) | <20 | 30 |
| Derivative (29) | <20 | 30 |
| Derivative (32) | 52 | 120 |
| Derivative (33) | 37 | 15 |
| Derivative (34) | 44 | 120 |
| Derivative (35) | 35 | 120 |
| Derivative (36) | 71 | 120 |
| Derivative (37) | 44 | 120 |
| Derivative (49) | <20 | 30 |
| Derivative (53) | <20 | 30 |
| Derivative (56) | 58 | 15 |
| Derivative (58) | <20 | 30 |
| Derivative (59) | <20 | 30 |
| Derivative (60) | <20 | 30 |
| Derivative (65) | <20 | 30 |
| Derivative (66) | <20 | 30 |
| Derivative (67) | <20 | 30 |
| Derivative (68) | 47 | 30 |
| Derivative (69) | <20 | 30 |
| Derivative (70) | 51 | 60 |
| Derivative (75) | <20 | 30 |

TABLE 36

| | | |
|---|---|---|
| Derivative (76) | <20 | 30 |
| Derivative (77) | <20 | 30 |
| Derivative (85) | <20 | 30 |
| Derivative (86) | <20 | 30 |
| Derivative (87) | <20 | 30 |
| Derivative (56) | <20 | 30 |
| Derivative (57) | <20 | 30 |
| Derivative (104) | 35 | 30 |
| Derivative (106) | 29 | 7.5 |
| Derivative (107) | 28 | 30 |
| Derivative (108) | <20 | 30 |
| Derivative (110) | <20 | 30 |
| Derivative (119) | <20 | 30 |
| Derivative (120) | 31 | 120 |
| Derivative (75) | <20 | 30 |
| Derivative (76) | <20 | 30 |
| Derivative (77) | <20 | 30 |
| Derivative (78) | 42 | 120 |
| Derivative (79) | 48 | 10 |
| Derivative (80) | 58 | 120 |
| Derivative (81) | 869 | 120 |
| Derivative (82) | 67 | 120 |
| Derivative (83) | 1049 | 120 |
| Derivative (84) | 907 | 30 |
| Derivative (85) | <20 | 30 |
| Derivative (86) | <20 | 30 |
| Derivative (87) | <20 | 30 |
| Derivative (88) | 600 | 120 |
| Derivative (89) | 132 | 30 |
| Derivative (90) | 92 | 30 |
| Derivative (91) | 103 | 30 |
| Derivative (96) | 80 | 120 |
| Derivative (97) | 53 | 10 |
| Derivative (98) | 54 | 120 |
| Derivative (99) | 37 | 120 |
| Derivative (100) | 59 | 120 |

TABLE 36-continued

| | | |
|---|---|---|
| Derivative (101) | 205 | 120 |
| Derivative (102) | 73 | 120 |

TABLE 37

| | | |
|---|---|---|
| Derivative (103) | 42 | 10 |
| Derivative (104) | 884 | 60 |
| Derivative (106) | 277 | 30 |
| Derivative (107) | 584 | 60 |
| Derivative (108) | 600 | 15 |
| Derivative (110) | <20 | 30 |
| Derivative (112) | 51 | 120 |
| Derivative (113) | 46 | 120 |
| Derivative (114) | 31 | 1 |
| Derivative (119) | 43 | 120 |
| Derivative (120) | 246 | 120 |

TABLE 38

<Effects of Compounds on β-Catenin Activity in SW480 Cell Line>

| | SW480 (TCF-FL) | |
|---|---|---|
| Compounds | Max. Activity (%) | Con. (μM) |
| Control (LiCl) | 100 | 20000 |
| Derivative (1) | 957 | 120 |
| Derivative (2) | <20 | 30 |
| Derivative (3) | 331 | 40 |
| Derivative (4) | <20 | 30 |
| Derivative (5) | 148 | 30 |
| Derivative (6) | 322 | 60 |
| Derivative (7) | <20 | 30 |
| Derivative (8) | <20 | 30 |
| Derivative (9) | <20 | 30 |
| Derivative (10) | 1079 | 120 |
| Derivative (11) | 625 | 60 |
| Derivative (12) | 1696 | 60 |
| Derivative (15) | <20 | 30 |
| Derivative (16) | 327 | 30 |
| Derivative (17) | 200 | 60 |
| Derivative (18) | 149 | 15 |
| Derivative (20) | 528 | 60 |
| Derivative (21) | 287 | 30 |

TABLE 39

| | | |
|---|---|---|
| Derivative (22) | 1226 | 30 |
| Derivative (23) | <20 | 30 |
| Derivative (25) | 223 | 120 |
| Derivative (26) | <20 | 30 |
| Derivative (27) | <20 | 30 |
| Derivative (28) | <20 | 30 |
| Derivative (29) | <20 | 30 |
| Derivative (32) | 789 | 120 |
| Derivative (33) | 580 | 120 |
| Derivative (34) | 120 | 120 |
| Derivative (35) | 130 | 120 |
| Derivative (36) | 283 | 120 |
| Derivative (37) | 296 | 120 |
| Derivative (38) | 551 | 10 |
| Derivative (39) | 344 | 30 |
| Derivative (40) | 896 | 30 |
| Derivative (41) | 676 | 30 |
| Derivative (42) | 1192 | 120 |
| Derivative (43) | 357 | 120 |
| Derivative (44) | 657 | 120 |
| Derivative (48) | 1047 | 30 |
| Derivative (49) | <20 | 30 |
| Derivative (50) | 1016 | 120 |

TABLE 39-continued

| | | |
|---|---|---|
| Derivative (51) | 1146 | 120 |
| Derivative (52) | 1030 | 30 |
| Derivative (53) | <20 | 30 |
| Derivative (56) | 650 | 600 |
| Derivative (57) | <20 | 30 |
| Derivative (58) | 270 | 30 |
| Derivative (59) | 592 | 60 |
| Derivative (60) | 196 | 30 |
| Derivative (61) | 56 | 120 |
| Derivative (65) | <20 | 30 |
| Derivative (66) | <20 | 30 |
| Derivative (67) | <20 | 30 |
| Derivative (68) | 486 | 60 |
| Derivative (69) | <20 | 30 |
| Derivative (70) | 789 | 120 |

TABLE 40

| | | |
|---|---|---|
| Derivative (71) | 919 | 30 |
| Derivative (72) | 1321 | 120 |
| Derivative (73) | 853 | 30 |
| Derivative (75) | <20 | 30 |
| Derivative (76) | <20 | 30 |
| Derivative (77) | <20 | 30 |
| Derivative (78) | 42 | 120 |
| Derivative (79) | 48 | 10 |
| Derivative (80) | 58 | 120 |
| Derivative (81) | 869 | 120 |
| Derivative (82) | 67 | 120 |
| Derivative (83) | 1049 | 120 |
| Derivative (84) | 907 | 30 |
| Derivative (85) | <20 | 30 |
| Derivative (86) | <20 | 30 |
| Derivative (87) | <20 | 30 |
| Derivative (88) | 600 | 120 |
| Derivative (89) | 132 | 30 |
| Derivative (90) | 92 | 30 |
| Derivative (91) | 103 | 30 |
| Derivative (96) | 80 | 120 |
| Derivative (97) | 53 | 10 |
| Derivative (98) | 54 | 120 |
| Derivative (99) | 37 | 120 |
| Derivative (100) | 59 | 120 |
| Derivative (101) | 205 | 120 |
| Derivative (102) | 73 | 120 |
| Derivative (103) | 42 | 10 |
| Derivative (104) | 884 | 60 |
| Derivative (106) | 277 | 30 |
| Derivative (107) | 584 | 60 |
| Derivative (108) | 600 | 15 |
| Derivative (110) | <20 | 30 |
| Derivative (112) | 51 | 120 |
| Derivative (113) | 46 | 120 |
| Derivative (114) | 31 | 1 |
| Derivative (119) | 43 | 120 |
| Derivative (120) | 246 | 120 |

TABLE 41

| | | |
|---|---|---|
| Derivative (131) | 1168 | 120 |
| Derivative (132) | 1490 | 120 |
| Derivative (133) | 1136 | 30 |
| Derivative (134) | 1493 | 10 |
| Derivative (135) | 945 | 120 |
| Derivative (136) | 837 | 1 |
| Derivative (137) | 1139 | 30 |
| Derivative (139) | 922 | 30 |
| Derivative (140) | 1091 | 30 |
| Derivative (141) | 519 | 120 |
| Derivative (143) | 93 | 120 |
| Derivative (149) | 70 | 30 |
| Derivative (150) | 78 | 30 |
| Derivative (151) | 41 | 30 |

TABLE 41-continued

| | | |
|---|---|---|
| Derivative (152) | 374 | 120 |
| Derivative (153) | 304 | 10 |
| Derivative (154) | 113 | 120 |
| Derivative (155) | 1060 | 30 |
| Derivative (156) | 1287 | 120 |
| Derivative (157) | 871 | 30 |
| Derivative (158) | 414 | 120 |
| Derivative (159) | 128 | 30 |
| Derivative (160) | 146 | 120 |
| Derivative (161) | 33 | 120 |
| Derivative (162) | 30 | 10 |
| Derivative (163) | 34 | 120 |
| Derivative (164) | 55 | 120 |
| Derivative (165) | 45 | 30 |
| Derivative (166) | 61 | 30 |
| Derivative (167) | 37 | 120 |
| Derivative (168) | 40 | 10 |
| Derivative (169) | 43 | 1 |
| Derivative (170) | 46 | 30 |
| Derivative (171) | 43 | 120 |
| Derivative (174) | 79 | 120 |
| Derivative (175) | 383 | 1 |
| Derivative (176) | 93 | 30 |
| Derivative (177) | 582 | 30 |

TABLE 42

| | | |
|---|---|---|
| Derivative (178) | 301 | 120 |
| Derivative (179) | 73 | 10 |
| Derivative (180) | 45 | 120 |
| Derivative (181) | 73 | 1 |
| Derivative (182) | 413 | 30 |
| Derivative (183) | 114 | 120 |
| Derivative (184) | 70 | 30 |
| Derivative (185) | 810 | 30 |
| Derivative (186) | 553 | 30 |
| Derivative (187) | 179 | 120 |
| Derivative (188) | 200 | 1 |
| Derivative (189) | 238 | 30 |
| Derivative (190) | 372 | 120 |
| Derivative (191) | 91 | 30 |
| Derivative (192) | 137 | 30 |
| Derivative (193) | 382 | 30 |
| Derivative (195) | 84 | 1 |
| Derivative (196) | 35 | 30 |
| Derivative (197) | 84 | 120 |
| Derivative (198) | 50 | 30 |
| Derivative (199) | 45 | 30 |
| Derivative (200) | 106 | 30 |
| Derivative (201) | 545 | 1 |
| Derivative (202) | 185 | 30 |
| Derivative (203) | 851 | 30 |
| Derivative (204) | 369 | 120 |
| Derivative (205) | 59 | 10 |
| Derivative (206) | 584 | 120 |
| Derivative (207) | 34 | 120 |
| Derivative (208) | 110 | 30 |
| Derivative (209) | 246 | 30 |
| Derivative (210) | 475 | 1 |
| Derivative (211) | 158 | 30 |
| Derivative (214) | 161 | 1 |
| Derivative (215) | 90 | 30 |
| Derivative (216) | 1086 | 10 |
| Derivative (217) | 1753 | 120 |
| Derivative (218) | 55 | 30 |

TABLE 43

| | | |
|---|---|---|
| Derivative (219) | 113 | 30 |
| Derivative (220) | 182 | 120 |
| Derivative (221) | 51 | 30 |
| Derivative (222) | 57 | 30 |
| Derivative (223) | 50 | 30 |

TABLE 43-continued

| | | |
|---|---|---|
| Derivative (251) | 35 | 120 |
| Derivative (252) | 49 | 120 |
| Derivative (253) | 66 | 10 |
| Derivative (254) | 37 | 120 |

Experimental Example 2

In vitro Assay for the Effect of Isoxazole Derivatives in Wnt/β-Catenin Signaling Activity using the Measurement of β-Catenin Level The HEK293 cell line was cultured in a DMEM supplemented with penicillin-streptomycin (100 Units/mL) and heat-inactivated 5% fetal bovine serum under standard conditions (5% $CO_2$, 37° C., 100% Relative humidity). Test compounds were dissolved in dimethylsulfoxide (DMSO) to concentrations of 30 and 60 μM. Cells ($3\times10^7$) were incubated for 24 hrs in the absence and the presence of the test compounds, respectively. For selectively obtaining cytoplasms, the cells were lysed with a high concentration of salt and the cell lysate suspension was centrifuged at 200 g for 10 min to recover the supernatant.

Figure 4:
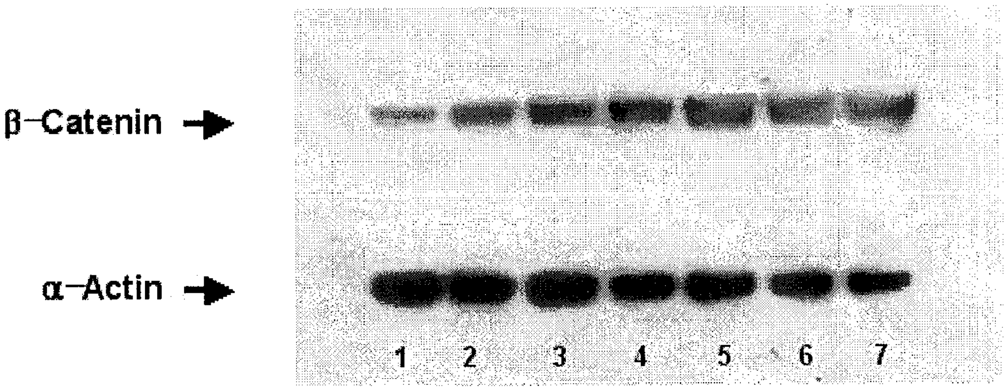
FIG. 4 shows the result of Western blots test using a human anti-β-catenin antibody for accumulation of the β-catenin in the cell, in the condition of treating various concentrations of the isoxazole derivatives of the present invention to HEK293 cells.

The cytoplasmic solution thus obtained was subjected to electrophoresis on 10% PAGE gel and probed with an anti-β-catenin antibody (Upstate Biotechnology Inc). Probing was performed with a chemoluminescence system (ECL, Amersham). For comparison, an actin protein was used as a control, and the results are given in FIG. 4. When the cells were treated with the compounds, as shown in the Western blots of FIG. 4, β-catenin was deposited in a dose-dependent pattern within cells.

Lithium chloride, serving as a positive control, widely used as a medication for manic-depressive psychosis, thereby suggested that Derivative (1) can be a cure for manic-depressive psychosis.

Experimental Example 3

Figure 5:
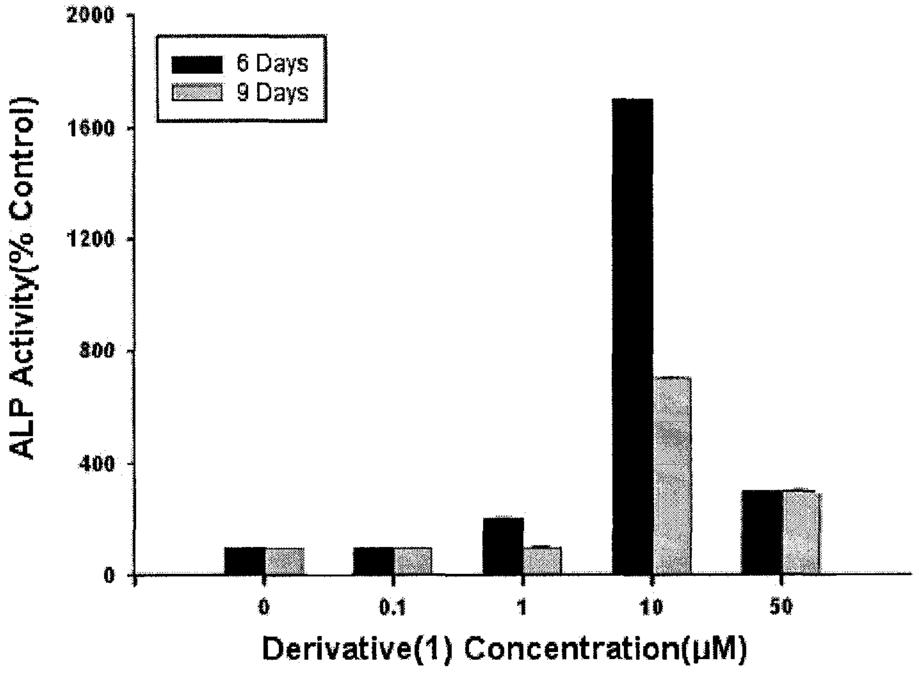
FIG. 5 is a bar graph showing activities of alkaline phosphatase (ALP), which is the indicator reflecting the rate of differentiation of the cell into osteoblast, comparing to the non-treated group with isoxazole derivatives, in the condition of various concentrations of isoxazole derivatives of the present invention to the osteoblast stem cell ST-2.

In vitro Assay of Isoxazole Derivatives for Prevention and Treatment of Osteoporosis The derivatives synthesized according to the present invention were assayed for their ability to differentiate stem cells into osteoblasts. In this regard, ST-2, a murine bone marrow stromal T cell, was used to measure the activity of bone-specific alkaline phosphatase, a marker of early-stage osteoblast differentiation. In detail, the cell line was cultured in an MEM supplemented with penicillin-streptomycin (100 Units/mL) and heat-inactivated 5% fetal bovine serum under standard culture conditions (5% $CO_2$, 37° C., 100% relative humidity). Treatment with trypsin and dissociation with a pipette resulted in a single cell suspension. The suspension was diluted with the same medium to adjust the cell count to 5,000~10,000 cells per well, and was moved in a 96-well microtiter, subsequently. After being incubated for 24 hrs, the cells were treated in a medium containing 50 μg/ml of ascorbic acid and 5 mM of β-glycerolphosphate with various concentrations of the isoxazole derivatives synthesized in Preparation Examples. During incubation for one to nine days, the Alkaline phosphatase activity was analyzed using a Luciferase Assay kit (Promega, U.S.A.) according to the protocol described in the manual provided by the manufacturer. The activities were measured in cells which had been incubated at 11 μM of each of the compounds for 4 days. Data on the activities of the isoxazole derivatives synthesized are given in Tables 44 to 47 and are expressed as percentages of ALP relative to that measured in the control, which was treated only with ascorbic acid and β-glycerolphosphate. ALP activities according to the concentrations of Derivative (1) are depicted in FIG. 5.

TABLE 44

<Effect of Derivatives on Differentiation of ST2 Cell Line into Osteoblasts>

| Compounds | ALP Activity (% Control) |
|---|---|
| Control (—) | 100 |
| Derivative (1) | 2915 |
| Derivative (5) | 3783 |
| Derivative (6) | 2132 |
| Derivative (10) | 7571 |
| Derivative (11) | 2807 |
| Derivative (12) | 4759 |
| Derivative (15) | 278 |
| Derivative (16) | 3063 |
| Derivative (17) | 3947 |
| Derivative (18) | 3671 |
| Derivative (20) | 2060 |
| Derivative (21) | 334 |
| Derivative (22) | 1334 |
| Derivative (23) | 4158 |
| Derivative (26) | 2587 |
| Derivative (28) | 436 |
| Derivative (30) | 3139 |
| Derivative (33) | 2232 |
| Derivative (34) | 2414 |
| Derivative (35) | 686 |
| Derivative (36) | 396 |
| Derivative (37) | 1093 |
| Derivative (38) | 2617 |
| Derivative (39) | 190 |
| Derivative (40) | 2139 |

TABLE 45

| | |
|---|---|
| Derivative (41) | 1850 |
| Derivative (42) | 2939 |
| Derivative (43) | 455 |
| Derivative (44) | 997 |
| Derivative (48) | 2817 |
| Derivative (49) | 2917 |
| Derivative (50) | 1122 |
| Derivative (51) | 1684 |
| Derivative (52) | 438 |
| Derivative (53) | 1069 |
| Derivative (56) | 1340 |
| Derivative (68) | 4885 |
| Derivative (69) | 2491 |
| Derivative (71) | 7087 |
| Derivative (72) | 5968 |
| Derivative (73) | 1522 |
| Derivative (81) | 2294 |
| Derivative (83) | 2848 |
| Derivative (84) | 4249 |
| Derivative (85) | 640 |
| Derivative (86) | 546 |
| Derivative (87) | 428 |
| Derivative (88) | 1259 |
| Derivative (89) | 2836 |
| Derivative (90) | 1258 |
| Derivative (91) | 1085 |
| Derivative (96) | 97 |
| Derivative (97) | 91 |
| Derivative (98) | 90 |
| Derivative (101) | 592 |
| Derivative (102) | 148 |

TABLE 45-continued

| | |
|---|---|
| Derivative (103) | 103 |
| Derivative (104) | 103 |
| Derivative (114) | 339 |
| Derivative (131) | 3810 |
| Derivative (132) | 20691 |
| Derivative (133) | 3143 |
| Derivative (134) | 1984 |

TABLE 46

| | |
|---|---|
| Derivative (135) | 1999 |
| Derivative (136) | 2254 |
| Derivative (137) | 2595 |
| Derivative (139) | 8191 |
| Derivative (140) | 5632 |
| Derivative (141) | 790 |
| Derivative (149) | 275 |
| Derivative (150) | 328 |
| Derivative (151) | 151 |
| Derivative (152) | 2061 |
| Derivative (153) | 1935 |
| Derivative (154) | 310 |
| Derivative (155) | 1481 |
| Derivative (156) | 4185 |
| Derivative (157) | 809 |
| Derivative (158) | 3629 |
| Derivative (159) | 130 |
| Derivative (160) | 158 |
| Derivative (161) | 89 |
| Derivative (162) | 60 |
| Derivative (163) | 166 |
| Derivative (164) | 241 |
| Derivative (165) | 92 |
| Derivative (166) | 64 |
| Derivative (167) | 276 |
| Derivative (168) | 97 |
| Derivative (169) | 83 |
| Derivative (170) | 74 |
| Derivative (171) | 74 |
| Derivative (175) | 767 |
| Derivative (176) | 179 |
| Derivative (177) | 1934 |
| Derivative (178) | 475 |
| Derivative (179) | 356 |
| Derivative (180) | 181 |
| Derivative (181) | 681 |
| Derivative (182) | 887 |
| Derivative (183) | 127 |

TABLE 47

| | |
|---|---|
| Derivative (184) | 126 |
| Derivative (185) | 714 |
| Derivative (186) | 272 |
| Derivative (187) | 99 |
| Derivative (188) | 151 |
| Derivative (189) | 220 |
| Derivative (190) | 269 |
| Derivative (191) | 309 |
| Derivative (192) | 398 |
| Derivative (193) | 173 |
| Derivative (194) | 2554 |
| Derivative (195) | 1070 |
| Derivative (196) | 77 |
| Derivative (197) | 118 |
| Derivative (198) | 100 |
| Derivative (199) | 63 |
| Derivative (200) | 162 |
| Derivative (201) | 859 |
| Derivative (202) | 109 |
| Derivative (203) | 260 |
| Derivative (204) | 150 |
| Derivative (205) | 58 |

TABLE 47-continued

| | |
|---|---|
| Derivative (206) | 772 |
| Derivative (207) | 47 |
| Derivative (208) | 57 |
| Derivative (209) | 1376 |
| Derivative (210) | 202 |
| Derivative (211) | 204 |
| Derivative (214) | 2143 |
| Derivative (215) | 162 |
| Derivative (218) | 128 |
| Derivative (219) | 1187 |
| Derivative (220) | 187 |

Experimental Example 4

Effect of Isoxazole Derivatives on In Vitro Calcium Deposition

The derivatives synthesized according to the present invention were assayed for their ability to differentiate stem cells into osteoblasts. In this regard, ST-2 cell, the murine bone marrow stromal T cell, was used to measure $Ca^{++}$ deposits, an indicator of late-stage osteoblast differentiation. In detail, the cell line was cultured in an MEM supplemented with penicillin-streptomycin (100 Units/mL) and heat-inactivated 10% fetal bovine serum under standard culture conditions (5% $CO_2$, 37° C., 100% relative humidity). Treatment with trypsin and dissociation with a pipette resulted in a single cell suspension. In a 24-well microtiter plate, subsequently, the suspension was diluted with the same medium to adjust the cell count to 5,000~10,000 cells per well.

Figure 6:
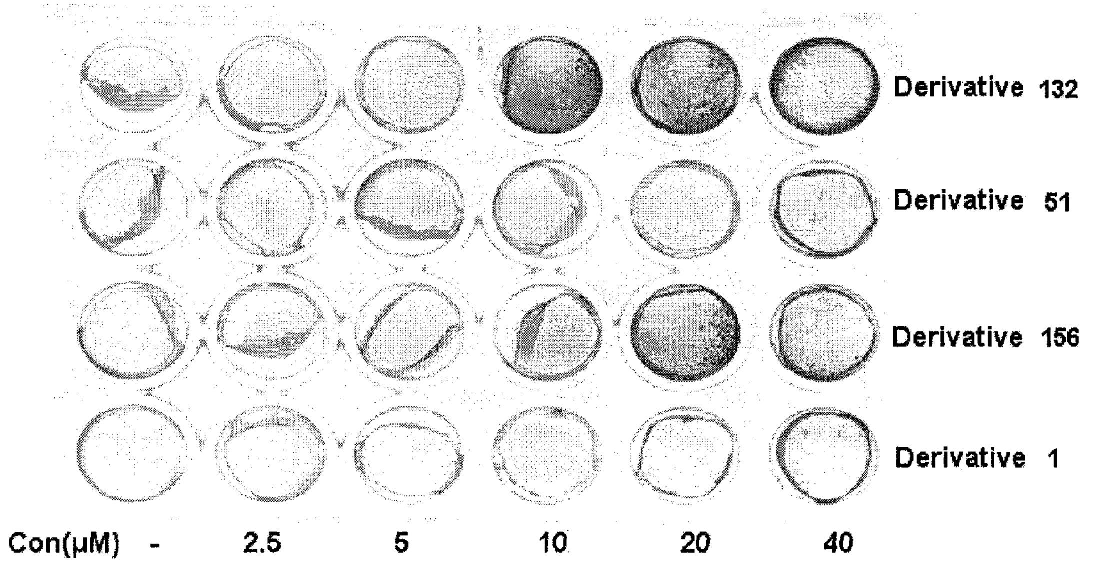
FIG. 6 shows the levels of $Ca^{++}$ deposit, which is the resulting indicator reflecting the rate of differentiation of the cell into osteoblast, comparing to the non-treated group with isoxazole derivatives, in the condition of various concentrations of isoxazole derivatives of the present invention to the osteoblast stem cell ST-2.

After being incubated for 24 hrs, the cells were treated for two days in a medium containing of 50 μg/ml of ascorbic acid and 5 mM of β-glycerolphosphate with various concentrations of the isoxazole derivatives synthesized in Preparation Examples. During incubation for 14 days in the absence of any derivative, the level of $Ca^{++}$ deposition was measured using an Alizarin Red S staining technique in order to analyze the ability to differentiate the stem cells into osteoblasts. Assays were performed according to the manual provided by the manufacturer, and the activities measured in the cells cultured for 14 days are shown in FIG. 6.

Experimental Example 5

In Vivo Assay of Isoxazole Derivatives for Prevention of Osteoporosis (1) Experimental Animals: ICR Mice (Female, 7 Weeks Old)

Experimental animals were female ICR mice having body weights of 24-28 g which were about 7 weeks old. In each cage, measuring 40×25×17 cm, 2-3 mice were reared at 22° C., RH 50%.

(2) Ovariectomy

Ovariectomy is known as one of the most widely used techniques for inducing osteoporosis. As in postmenopause case, the ovariectomy-operation induce estrogen insufficient, result in decrease of osteogenesis and increase of bone resorption, lead to osteoporosis. Anaesthetized 7-week-old female ICR mice underwent ovariectomies and, immediately after the removal of both ovaries, they were administered with test compounds to determine the preventive and therapeutic effects thereof on osteoporosis.

(3) Administration

1) Preparation of test material: Predetermined amounts of Derivative (1) were suspended in 0.5% CMC to prepare test materials to be administered. As for the control drug alendronate, 0.17% citric acid was added thereto as a pharmacopoeia to aid in the uptake of the drug.

2) Administration period: four weeks

3) Administration route and method: test materials were administered in a volume of 10 ml/kg of body weight, measured on the administration day, into seven groups: ① intact control (ICR mice bred with typical diet, control); ② ovariectomy control (the abdomen opened and closed without removal of the ovary, Sham); ③ ovariectomy group (ovaries removed, OVX); ④ alendronate-treated group (a dose of 5 mg/kg/day); ⑤ Derivative (1) 30 mg/kg/day treated group (OVX+Derivative (1) 30 mpk); ⑥ Derivative (1) 90 mg/kg/day treated group (OVX+Derivative (1) 90 mpk); and ⑦ Derivative (1) 90 mg/kg/week treated group (OVX+Derivative (1) 30 mpkW). Groups ①~⑥ were orally treated five day a week for four weeks while group ⑦ was treated once a week for four weeks.

(4) End Point

After administration for four weeks, the spine (L3-L6) was analyzed for bone mineral density (BMD) through dual-energy X-ray absorptiometry (DEXA) using a Lunar Pixi #5 instrument. Micro-computed tomography (Micro-CT) was performed to determine the effects of the test materials on bone mass and bone strength and on the tertiary bone mass of the spine (L3-L6).

(5) Test Result

1) Effect of Derivative (1) on BMD

Figure 7:
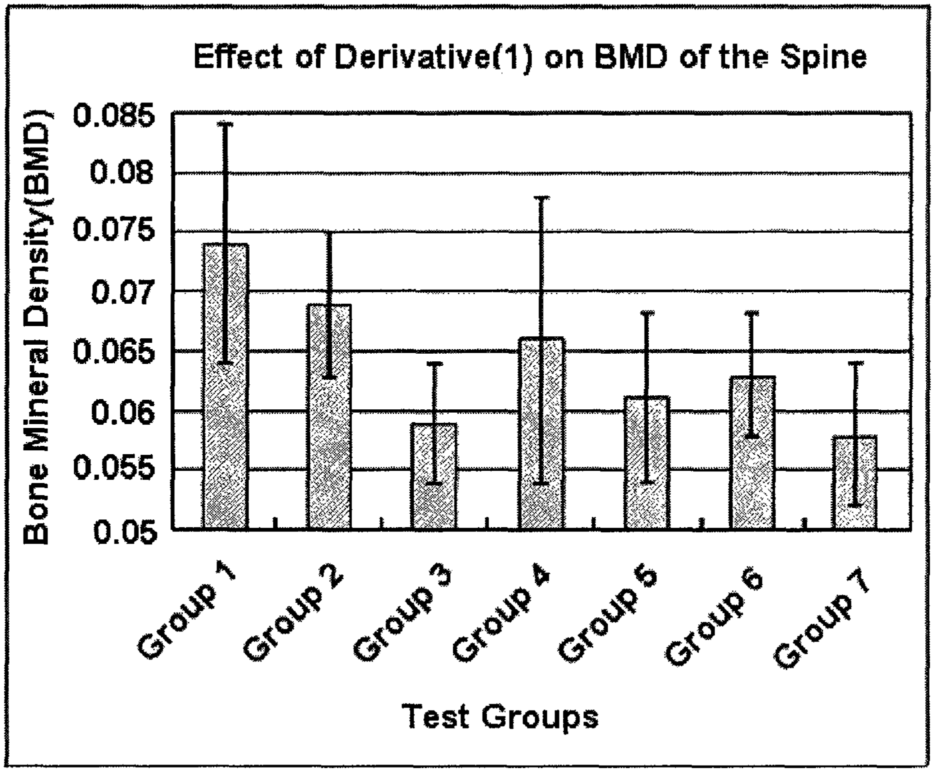
FIG. 7 is a bar graph to confirm the preventive effect on osteoporosis of the present invention showing the analysed result through dual-energy X-ray absorptiometry (DEXA) which appears to be not vanished away the bone mineral density (BMD) in the test group applying mice with ovariectomy, then feeded the isoxazole derivative (1) of the present invention for two weeks comparing to the contrasting group.

The effects of Derivative (1) on BMD are shown in FIG. 7 and Table 48. The OVX group decreased in bone mineral density by 14.5% on average, while the groups administered with Derivative (1) were found to decrease in bone mineral density to lesser extents compared to the OVX group. Therefore, the isoxazole compounds of the present invention were proven to be effective in the prevention of osteoporosis.

2) Effect of Derivative (1) on Bone Mass (BV/TV)

Figure 8:
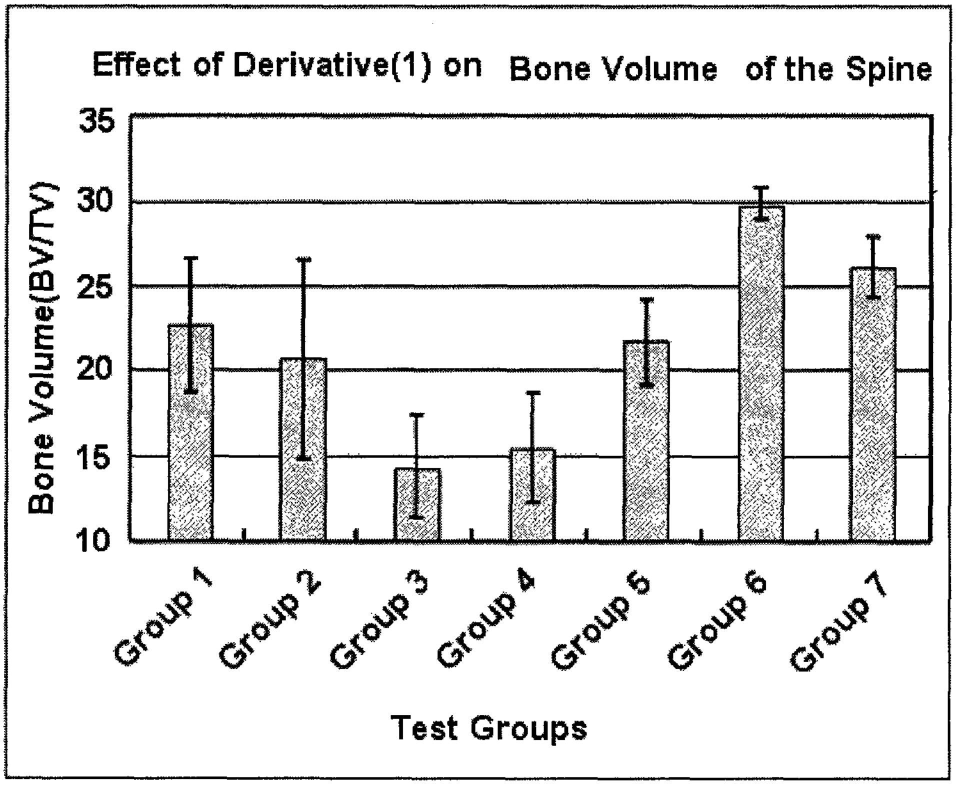
FIG. 8 is a bar graph to confirm the treatment effect on osteoporosis of the present invention showing the analysed result through micro-CT which appears to be increasing the bone volume (BV/TV) in the test group applying mice with ovariectomy, then feeded with the isoxazole derivative (1) of the present invention as solid feedstuff for 4 weeks to induce osteoporosis therein and then feeded the derivative (1) for additionally 4 weeks comparing to the contrasting group treating with no derivative (1).

The effects of Derivative (1) on bone mass (BV/TV) are shown in FIG. 8 and Table 48.

Four weeks after ovariectomy, the OVX group suffered from acute osteoporosis, as they decreased in bone mass by 30.4% on average. The administration of Derivative (1) for the same period was found not only to restrain the decrease of bone mass, but also to increase the bone density to a higher level than before ovariectomy. This therapeutic effect was identified to exceed that of alendronate, which is currently used as a preventive and curative of osteoporosis.

Capable of increasing bone mass in comparison to that of the Sham group and the intact group, the Derivatives of the present invention are expected to show a therapeutic effect on patients suffering from osteoporosis.

TABLE 48

<Therapeutic Effect of Derivative (1) on Osteoporosis in Comparison to Alendronate>

| | BMD ($g/cm^2$) | | Trabeculae volume($mm^2$) | |
|---|---|---|---|---|
| Test Groups | Avg. ± SD | Change (%) | Avg. ± SD | Change (%) |
| Group 1 (Intact) | 0.074 ± 0.010 | 7.2 | 22.7 ± 3.86 | 9.7 |
| Group 2 (Sham) | 0.069 ± 0.006 | 0.0 | 20.7 ± 5.87 | 0.0 |
| Group 3 (OVX) | 0.059 ± 0.005 | −14.5 | 14.4 ± 3.09 | −30.4 |

TABLE 48-continued

<Therapeutic Effect of Derivative (1) on Osteoporosis in Comparison to Alendronate>

| | BMD ($g/cm^2$) | | Trabeculae volume($mm^2$) | |
|---|---|---|---|---|
| Test Groups | Avg. ± SD | Change (%) | Avg. ± SD | Change (%) |
| Group 4 (OVX + AD) | 0.066 ± 0.012 | −4.3 | 15.5 ± 3.27 | −25.1 |
| Group 5 (OVX + D30) | 0.061 ± 0.007 | −11.6 | 21.7 ± 2.43 | 4.8 |
| Group 6 (OVX + D90) | 0.063 ± 0.005 | −8.7 | 29.9 ± 0.83 | 44.4 |
| Group 7 (OVX + W30) | 0.058 ± 0.006 | −15.9 | 26.1 ± 1.87 | 26.1 |

Experimental Example 6

In Vivo Pre-Toxicity Assay of Isoxazole Derivative

The isoxazole derivative was assayed for in vivo acute toxicity by conducting Rotarod neurotoxicity experiments in ICR-BG mice (N=8). 1 hr after being trained twice at 7 rpm for 10 min, 8 mice were administered intraperitoneally with Derivative (1) in a dose of 300 mg/g. 30 min, 1 hr, 2 hr and 4 hr after the administration, the mice were monitored for numbers of falls and reactions indicative of death or pain. The number of falls was counted whenever mice fell off the rod three times or more during 1 min. The results are given in Table 49, below.

TABLE 49

<Test Results of Rotarod Neurotoxicity of Derivative (1)>

| No. | Body Weight(g) | 0.5 hr | 1 hr | 2 hr | 4 hr |
|---|---|---|---|---|---|
| Derivative (1) 300 mg/kg | 25~27 (Avg. 26) | (0)/8 | (0)/8 | (0)/8 | (0)/8 |
| | | | (No. of falling off)/ No. of Test Animals | | |

As shown in Table 49, the number of mice that fell off the rod after the intraperidominal administration of the compound of the present invention at a dose of 300 mg/kg was zero, and no reactions relevant to death or pain were observed.

Taken together, the data obtained in Experimental Examples 1 to 6 demonstrate that the isoxazole derivatives of the present invention can act as agonists of Wnt/β-catenin signaling and effectively activate signal transduction even at a low concentration, with the concomitant effects of accumulating β-catenin within cells, promoting differentiation into osteoblasts, and preventing and treating osteoporosis. Serving as an activator of Wnt/β-catenin signaling, therefore, the compounds of the present invention can be used as drugs that are effective in the treatment and prevention of osteoporosis and bone diseases.

INDUSTRIAL APPLICABILITY

As described hitherto, the isoxazole derivatives according to the present invention, activate Wnt/β-catenin signaling very effectively, and thus can be used as active ingredients effective in the prevention and treatment of various diseases, including bone diseases, such as osteoporosis, metabolic diseases, such as obesity and diabetes mellitus, and brain injury and nerve cell abnormality-related diseases, such as Parkinson's disease, strokes, ischemic cerebral diseases, epilepsy, Alzheimers disease, depression, bipolar disorder, and schizophrenia. In addition, the isoxazole derivatives of the present invention act to promote the differentiation and growth of stem cells, finding applications in the medicinal industry, including hair regrowth, haematopoiesis, and tissue regeneration.

The invention claimed is:

1. An isoxazole derivative of the following Chemical Formula 1, or a pharmaceutically acceptable salt thereof:

[Chemical Formula 1]

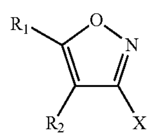

wherein, $R_1$ is an aryl group selected from the group consisting of thienyl, furanyl and phenyl that may be unsubstituted or substituted with one or more substituents selected from the group consisting of acyl, amino, carboalkoxy, carboxy, carboxyamino, —O-carbamoyl, cyano, halo, hydroxy, nitro, thio, alkyl, cycloalkyl, aryl, alkoxy, aryloxy, sulfoxy and guanido;

$R_2$ is hydrogen; and

X is a substituent of the following Chemical Formula 2;

[Chemical Formula 2]

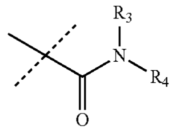

wherein $R_3$ is hydrogen,

R4 is an alkyl group substituted with an aryl group selected from the group consisting of phenyl, imidazolyl, triazolyl, and pyridyl, wherein the alkyl group is further unsubstituted and said phenyl, imidazolyl, triazolyl, and pyridyl may be unsubstituted or substituted with one or more substituents selected from the group consisting of amino, carboalkoxy, carboxy, halo, hydroxy, nitro, alkyl, and alkoxy wherein, when R4 is an alkyl group substituted with an aryl group and R1 is substituted or unsubstituted phenyl, said aryl group is imidazolyl or triazolyl.

2. An isoxazole derivative or the pharmaceutically acceptable salt thereof as set forth in claim 1, wherein the isoxazole derivative is selected from a group consisting of the following compounds:

(1) 5-furan-2-yl-isoxazole-3-carboxylic acid (3-imidazol-1-yl-propyl)-amide, (10): 5-furan-2-yl-isoxazole-3-carboxylic acid (2-pyridin-2-yl-ethyl)-amide, (11): 5-furan-2-yl-isoxazole-3-carboxylic acid (2-pyridin-3-yl-ethyl)-amide, (12): 5-furan-2-yl-isoxazole-3-carboxylic acid (2-pyridin-4-yl-ethyl)-amide, (33): 5-furan-2-yl-isoxazole-3-carboxylic acid (2-imidazol-1-yl-ethyl)-amide, (35): 5-furan-2-yl-isoxazole-3-carboxylic acid [2-(2-methyl-imidazol-1-yl)-ethyl]-amide, (36): 5-furan-2-yl-isoxazole-3-carboxylic acid [2-(5-methyl-imidazol-1-yl)-ethyl]-amide, (37): 5-furan-2-yl-isoxazole-3-carboxylic acid [2-(4-methyl-imidazol-1-yl)-ethyl]-amide, (38): 5-furan-2-yl-isoxazole-3-carboxylic acid (2-[1,2,4]triazol-1-yl-ethyl)-amide, (40): 5-furan-2-yl-isoxazole-3-carboxylic acid (2-[1,2,3]triazol-2-yl-ethyl)-amide, (41): 5-furan-2-yl-isoxazole-3-carboxylic acid (2-[1,2,3]triazol-1-yl-ethyl)-amide, (44): 5-furan-2-yl-isoxazole-3-carboxylic acid [3-(2-methyl-imidazol-1-yl)-propyl]-amide, (49): 5-furan-2-yl-isoxazole-3-carboxylic acid (3-[1,2,3]triazol-1-yl-propyl)-amide, (50): 5-furan-2-yl-isoxazole-3-carboxylic acid (3-[1,2,3]triazol-2-yl-propyl)-amide, (51): 5-furan-2-yl-isoxazole-3-carboxylic acid (3-[1,2,4]triazol-1-yl-propyl)-amide, (56): 5-furan-2-yl-isoxazole-3-carboxylic acid [3-(4-methyl-imidazol-1-yl)-propyl]-amide, (68): 5-phenyl-isoxazole-3-carboxylic acid (3-imidazol-1-yl-propyl)-amide, (69): 5-phenyl-isoxazole-3-carboxylic acid (2-imidazol-1-yl-ethyl)-amide, (78): 5-o-tolyl-isoxazole-3-carboxylic acid (3-imidazol-1-yl-propyl)-amide, (79): 5-m-tolyl-isoxazole-3-carboxylic acid (3-imidazol-1-yl-propyl)-amide, (80): 5-p-tolyl-isoxazole-3-carboxylic acid (3-imidazol-1-yl-propyl)-amide, (81): 5-(2-fluoro-phenyl)-isoxazole-3-carboxylic acid (3-imidazol-1-yl-propyl)-amide, (82): 5-(3-fluoro-phenyl)-isoxazole-3-carboxylic acid (3-imidazol-1-yl-propyl)-amide, (83): 5-(4-fluoro-phenyl)-isoxazole-3-carboxylic acid (3-imidazol-1-yl-propyl)-amide, (84): 5-(4-fluoro-phenyl)-isoxazole-3-carboxylic acid (3-[1,2,4]triazol-1-yl-propyl)-amide, (85): 5-(2-fluoro-phenyl)-isoxazole-3-carboxylic acid (2-imidazol-1-yl-ethyl)-amide, (86): 5-(4-fluoro-phenyl)-isoxazole-3-carboxylic acid (2-imidazol-1-yl-ethyl)-amide, (88): 5-(4-fluoro-phenyl)-isoxazole-3-carboxylic acid (2-[1,2,4]triazol-1-yl-ethyl)-amide, (89): 5-(4-fluoro-phenyl)-isoxazole-3-carboxylic acid (2-[1,2,3]triazol-2-yl-ethyl)-amide, (90): 5-(4-fluoro-phenyl)-isoxazole-3-carboxylic acid (2-[1,2,3]triazol-1-yl-ethyl)-amide, (96): 5-(4-chloro-phenyl)-isoxazole-3-carboxylic acid (3-[1,2,4]triazol-1-yl-propyl)-amide, (97): 5-(4-chloro-phenyl)-isoxazole-3-carboxylic acid (2-[1,2,4]triazol-1-yl-ethyl)-amide, (98): 5-(4-chloro-phenyl)-isoxazole-3-carboxylic acid (3-imidazol-1-yl-propyl)-amide, (99): 5-(2-methoxy-phenyl)-isoxazole-3-carboxylic acid (3-imidazol-1-yl-propyl)-amide, (100): 5-(3-methoxy-phenyl)-isoxazole-3-carboxylic acid (3-imidazol-1-yl-propyl)-amide, (101): 5-(4-methoxy-phenyl)-isoxazole-3-carboxylic acid (3-imidazol-1-yl-propyl)-amide, (113): 5-(3-nitro-phenyl)-isoxazole-3-carboxylic acid (3-imidazol-1-yl-propyl)-amide, (114): 5-(4-nitro-phenyl)-isoxazole-3-carboxylic acid (3-imidazol-1-yl-propyl)-amide, (119): 5-(3-amino-phenyl)-isoxazole-3-carboxylic acid (3-imidazol-1-yl-propyl)-amide, (120): 5-(4-amino-phenyl)-isoxazole-3-carboxylic acid (3-imidazol-1-yl-propyl)-amide, (131): 5-thiophen-2-yl-isoxazole-3-carboxylic acid (3-imidazol-1-yl-propyl)-amide, (132): 5-thiophen-2-yl-isoxazole-3-carboxylic acid-(3-[1,2,4]-triazol-1-yl-propyl)-amide, (133): 5-thiophen-2-yl-isoxazole-3-carboxylic acid (2-imidazol-1-yl-ethyl)-amide, (135): 5-thiophen-2-yl-isoxazole-3-carboxylic acid (2-[1,2,4]triazol-1-yl-ethyl)-amide, (136): 5-thiophen-2-yl-isoxazole-3-carboxylic acid (2-[1,2,3]triazol-2-yl-ethyl)-amide, (137): 5-thiophen-2-yl-isoxazole-3-carboxylic acid (2-[1,2,3]triazol-1-yl-ethyl)-amide, (139): 5-thiophen-2-yl-isoxazole-3-carboxylic acid (2-pyridin-3-yl-ethyl)-amide, (140): 5-thiophen-2-yl-isoxazole-3-carboxylic acid (2-pyridin-4-yl-ethyl)-amide, (143): 5-(5-bromo-thiophen-2-yl)-isoxazole-3-carboxylic acid (3-imidazol-1-yl-propyl)-amide, (152): 5-furan-3-yl-isoxazole-3-carboxylic acid (3-imidazol-1-yl-propyl)-amide, (153): 5-furan-3-yl-isoxazole-3-carboxylic acid (3-[1,2,4]-triazol-1-yl-propyl)-amide, (154): 5-furan-3-yl-isoxazole-3-carboxylic acid (2-[1,2,4]-triazol-1-yl-ethyl)-amide, (155): 5-thiophen-3-yl-isoxazole-3-carboxylic acid (3-[1,2,4]-triazol-1-yl-propyl)-amide, (156): 5-thiophen-3-yl-isoxazole-3-carboxylic acid (3-imidazol-1-yl-propyl)-amide, (157): 5-thiophen-3-yl-isoxazole-3-carboxylic acid (2-imidazol-1-yl-ethyl)-amide, and (158): 5-thiophen-3-yl-isoxazole-3-carboxylic acid (2-[1,2,4]-triazol-1-yl-ethyl)-amide.

3. A pharmaceutical composition comprising an isoxazole derivative in accordance with claim 2 selected from the group consisting of:

(1) 5-furan-2-yl-isoxazole-3-carboxylic acid (3-imidazol-1-yl-propyl)-amide, (10): 5-furan-2-yl-isoxazole-3-carboxylic acid (2-pyridin-2-yl-ethyl)-amide, (12): 5-furan-2-yl-isoxazole-3-carboxylic acid (2-pyridin-4-yl-ethyl)-amide, (49): 5-furan-2-yl-isoxazole-3-carboxylic acid (3-[1,2,3]triazol-1-yl-propyl)-amide, (68): 5-phenyl-isoxazole-3-carboxylic acid (3-imidazol-1-yl-propyl)-amide, (84): 5-(4-fluoro-phenyl)-isoxazole-3-carboxylic acid (3-[1,2,4]triazol-1-yl-propyl)-amide, (131): 5-thiophen-2-yl-isoxazole-3-carboxylic acid (3-imidazol-1-yl-propyl)-amide, (132): 5-thiophen-2-yl-isoxazole-3-carboxylic acid-(3-[1,2,4]-triazol-1-yl-propyl)-amide, (133): 5-thiophen-2-yl-isoxazole-3-carboxylic acid (2-imidazol-1-yl-ethyl)-amide, (156): 5-thiophen-3-yl-isoxazole-3-carboxylic acid (3-imidazol-1-yl-propyl)-amide, and (158): 5-thiophen-3-yl-isoxazole-3-carboxylic acid (2-[1,2,4]-triazol-1-yl-ethyl)-amide in a therapeutically effective amount to treat postmenopausal osteoporosis and osteoarthropathy and a pharmaceutically acceptable carrier suitable for formulating the composition into oral, parenteral, or transdermal preparations.

* * * * *